(12) United States Patent
Peters et al.

(10) Patent No.: US 8,404,934 B2
(45) Date of Patent: Mar. 26, 2013

(54) GENES ENCODING NEMATODE TOXINS

(75) Inventors: Cheryl L. Peters, Raleigh, NC (US); Brian Vande Berg, Durham, NC (US); Brian Carr, Raleigh, NC (US); Julia T. Daum, Apex, NC (US); Vadim Beilinson, Cary, NC (US); Sandra Volrath, Durham, NC (US); Candace Poutre, Moncure, NC (US); Kimberly Sampson, Durham, NC (US)

(73) Assignee: Athenix Corporation, Morrisville, NC (US)

( * ) Notice: Subject to any disclaimer, the term of this patent is extended or adjusted under 35 U.S.C. 154(b) by 306 days.

(21) Appl. No.: 12/638,591

(22) Filed: Dec. 15, 2009

(65) Prior Publication Data

US 2010/0166723 A1 Jul. 1, 2010

Related U.S. Application Data

(60) Provisional application No. 61/122,674, filed on Dec. 15, 2008, provisional application No. 61/224,811, filed on Jul. 10, 2009.

(51) Int. Cl.
| | | |
|---|---|---|
| *C12N 1/21* | (2006.01) | |
| *C12N 15/32* | (2006.01) | |
| *C12N 15/82* | (2006.01) | |
| *A01N 37/18* | (2006.01) | |
| *C07K 14/325* | (2006.01) | |

(52) U.S. Cl. .................. 800/302; 536/23.71; 435/320.1; 435/252.3; 435/418; 514/4.6; 800/279

(58) Field of Classification Search .......................... None
See application file for complete search history.

(56) References Cited

U.S. PATENT DOCUMENTS 6,222,097 B1 * 4/2001 McBride et al. .............. 800/282

FOREIGN PATENT DOCUMENTS

| JP | 2004016147 | * | 1/2004 |
| WO | 2005/094256 | | 10/2005 |

OTHER PUBLICATIONS

GenBank Accession No. M11582 (1996).*
Li et al (2002, Planta, 215:239-247).*
GenBank Accession No. Q06355.1 (2011).*
Felton et al (1992, J. Insect Physiol. 38:277-285).*
Anita et al (2004, Nematolgia Mediterranea 32:47-51, abstract only).*
Gen Bank Accession No. P06845, 2011.*
Mahanil Siraprapa et al. "Overexpression of Tomato Polyphenol Oxidase Increases Resistance to Common Cutworm", Plant Science (Oxford), vol. 174, No. 4, Apr. 2008, pp. 456-466, XP 002576854.
Li Li et al. "Overexpression of Polyphenol Oxidase in Transgenic Tomato Plants Results in Enhanced Bacterial Disease Resistance", Planta (Berlin), vol. 215, No. 2, Jun. 2002, pp. 239-247, XP002576855.
Wang Jiehua et al. "Polyphenol Oxidase Overexpression in Transgenic Populus Enhances Resistance to herbivory by Forest Tent Caterpillar", Planta (Berlin) vol. 220, No. 1, Nov. 2004, pp. 87-96, XP002576856.
Wuyts N et al. "Extraction and Partial Characterization of Polyphenol Oxidase from Banana (*Musa acuminata* Grande naive) roots", Plant Physiology and Biochemistry, vol. 44, No. 5-6, May 2006, pp. 308-314, XP025103947.
International Search Report, mailed Apr. 22, 2010 (3 pages).
Kimber, Michael J,. et al., "*flp* gene disruption in a parasitic nematode reveals motor dysfunction and unusual neuronal sensitivity to RNA interference," *The FASEB Journal*, 2007, vol. 21, pp. 1233-1243.
Marshall, et al. (2000) "Enzymatic Browing in Fruits, Vegetables and Seafoods," *Food and Agricultural Organization of the United Nations*, http://www.fao.org/ag/Ags/agsi/ENZYMEFINAL/ Enzymatic%20Browning.html.
Mayer, Alfred M., "Polyphenol oxidases in plants and fungi: Going places? A review," *Phytochemistry*, 2006, vol. 67, pp. 2318-2331.
Nansen, Peter, et al., "Interactions between the Predacious Fungus *Arthrobotrys oligospora* and Third-Stage Larvae of a Series of Animal-Parasitic Nematodes," *Veterinary Parasitology*, 1988, vol. 26, pp. 329-337.
Urwin, P.E., et al., "Ingestion of Double-Stranded RNA by Preparasitic Juvenile Cyst Nematodes Leads to RNA Interference," *MPMI*, 2002, pp. 747-752, vol. 15, No. 8.

* cited by examiner

*Primary Examiner* — Anne Kubelik

(57) ABSTRACT

Compositions and methods for conferring nematicidal activity to bacteria, plants, plant cells, tissues and seeds are provided. Compositions including a coding sequence for nematicidal polypeptides are provided. The coding sequences can be used in DNA constructs or expression cassettes for transformation and expression in plants and bacteria. Compositions also include transformed bacteria, plants, plant cells, tissues, and seeds. In particular, isolated nematicidal nucleic acid molecules are provided. Additionally, amino acid sequences corresponding to the polynucleotides are encompassed. In particular, the present invention provides for isolated nucleic acid molecules including nucleotide sequences encoding the amino acid sequence shown in SEQ ID NO:4, 5, 8, 9, 13, 14, 47, 48, or 49, the nucleotide sequence set forth in SEQ ID NO:1, 2, 3, 6, 7, 10, 11, 12, 15, 45, or 46, as well as variants and fragments thereof.

17 Claims, 7 Drawing Sheets

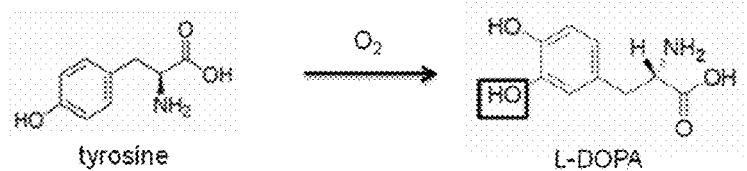
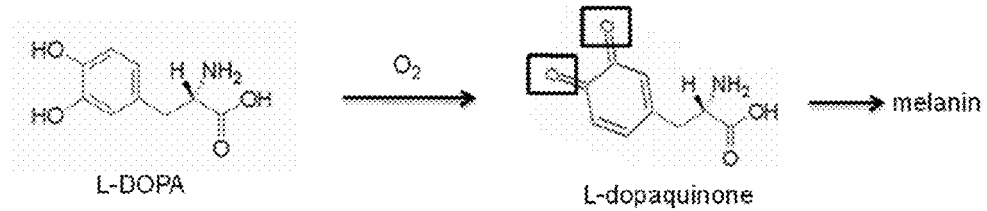
FIG. 1

AXN-1 precursor: 944 aa  MW 103,635

ATG  Arthrobotrys tyrosinase precursor                                                polyA tail Peak 29
       MASAPYAITGIPTTRAPDGALPLRQEIDAWSANPANVDQVNLYLQALAAFQQLPATDKLS
       YFQIAGIHGEPFIPWDENTSFNERSRWRGYCTHASILFPTWHRPYLAVFEQILHSIMQRI
       AAAYPDQELRTRYQTAAEAFRIPYWDSAQLKERGGRRSLNVPYLCTLPTVQVFTPTSAGD
       TIRPFETIDNFLYSYKFVTTQGITSFQKQDGNFFPEANAMGTSRYFPQYNSKDPTVSSQW
       TNGFVDNDSITEALRMLESLGEDVYRSFTTSNYAWYSSTQQSNPPAPNSYQSLESIHHEI   Peak 36
Peak 20 HGITGGGGHMSWNTVSSFDPIFWLHHCNVDRLEAIWQAIYADTGR*YPDAWFHAQSAQLHD*
        *THHTWSLAAGSR*ENADTPLAPFHKDDRGSVYNSNDVPNNTR *FGSSYPELQP*WLPQYR*DST*
        *GEFNATLYR*NDVVAQVTDLYSRVRRRVQNTQVFRNRLFAATQTGTQTFQGS...    Peak 42
Peak 24 QPTTQGPGQQLQFGPPFSGGQQAFAPPFTVQAQAQSQGQPFTPPTTLFTQGQQFTSPFF
        QTAQGGQFPFFPTQQQQFSPPFTHQQQFAPPFTQEHGQAVTSFPAQTQFSPPFTQAFSPF
        PTGDSHGQQFTPQFQQQFTPQFQXQQQKQFAPFQLGPGGHTPQGQHSSFPPKKSGLSGLM
        SSAKLHFGEALTAGREAAQGHQQPVQQHQQPTHTPGHPSSSTALATKFGGIIGGSIHMA
        QERLGSKKQFGQPSTRGIDDEFGQEGELSRGFGGMSLGQQSFGSSESLTTHEYDANIRFE
        RFDLGERPFTVHIFLGDFNPDFATWNSWDKNRVGGIYNFVAGVQRGDGSACSNCETQSQDH
        TIVTGQVSLTNALLDDVEDSANGLNSLIPEEVIPYLQRGHLHWRITDPNGREIFRQSLNTL
        KISVVECSATISNNPGELTQYGDHRVLDIVTEGRPAGKAAGDST

FIG. 2

```
                      *         20         *         40         *         60         *         80         *      1
AXN-1           : ------YAITGIPTTRAPDGALPLRQEIDAWSANPANV--DQVNLYLQALAAFQQLP---ATDKLSYFQIAGIHGEPFIPWDENTS-----PNPRSRW :  82
Neurospora_cra  : MSTDIKFAIT--------GAVPLRRELRDLQQNYP----EQFNLYLLGLRDFQGLD---EAKLDSYYQVAGIHGMPFKPWAGVPSDTDWSQPGSSGF :  82
Pyrenophora_tr  : -MVNDTQAFQQGALSNALTGNVFVRREVRDLQANFP----DQWTLYILALNKLHNAN---QSDAYSFYGIASIHGRPFQTWGDAPG------LPYKQGM :  85
Podospora_anse  : MSTTGNIAITGIPTTAGPDGSFPLRRELRDLQRNYP----DHFNLLVLALKDFQALN---ESVQTSYYQIAGIHGLPYKPWNNVGSNSDWQS--TSGF :  89
Lentinula_edod  : MSRYLVTGATGGSTSG---AAAPNRLEINDFVKQE-----DQFSLYIQALQYIYSSK--SQDDIDSFFQIGGIHGLPYVPWDGAGN----KPVDTDAW :  84
Pycnoporus_san  : MSHFIVTGPVGGQTEG---APAPNRLEINDFVKNE-----EFFSLYVQALDIMYGLK---QEELISFFQIGGIHGLPYVAWSDAG------ADDPAEP :  81
Pholio_nameko   : MSRVVITGVSG-------TVANRLEINDFVKND------KFFSLYIQALQVMSSVP--PQENVRSFFQIGGIHGLPYTPWDGITGD--QPFDPNTQW :  80
Tuber_melanosp  : -MTMKTYPITGVASQAP-----RPRRNINDFAQDP-----LQWNLFLQALINLQSQGED-THSPLGYVQVAGVHGTPYIPWMEKAD-------ADDRA :  79
Asp_fum_tyrosi  : MSSNKPYVIKGIPVDAG--QIIPVRRDIDEWYEDTSRQSRIQLSIFIWALREFQSID---YKDRLSYFQIAGIHHFPLITWDEEEP-------PVDNK :  86

00         *        120         *        140         *        160         *        180         *
AXN-1           : RGYCTHASILFPTWHRPYLAVFEQILHSIMQRIAAAYP-DQELRTRYQTAAEAFRIPYWDSAQLKERGGRRSLNVPYLCTLPTVQVFTFTSAGDTIRP : 179
Neurospora_cra  : GGYCTHSSILFITWHRPYLALYEQALYASVQAVAQKFPVEGGLRAKYVAAAKDFRAPYFDWASQPPKGT---LAFPESLSSRTIQVVDVDGR------ : 171
Pyrenophora_tr  : TGYCTPHGNELFMGWHRPYLALFEQVVSDYVHDIATQAPTD--KVERYLAAANEFRIPYWDWAQGTNSGP-----VPEFFTNPMLTVTNTDCVS---- : 171
Podospora_anse  : GGYCTHSSILFITWHRPYLALFEQALYNSIQKIANQFP--QGPLRTKYVEAAKTFRMPYFDWASQPPSGS---SAFPSAFTAPSLQVVDVDGR----- : 177
Lentinula_edod  : EGYCTHGSVLFPTFHRPYVLLIEQAIQAAAVDIAATYIV---DRARYQDAALNLRQPYWDWARNPVPP-------PEVISLDEVTIVNPSGE------ : 166
Pycnoporus_san  : SGYCTEGSVLFPTWHRPYVALYEQILHKYAGEIADKYTV---DKPRWQKAAADLRQPFWDWAKNTLPP-------PEVISLDKVTITTPDGC------ : 163
Pholio_nameko   : GGYCTHGSVLFPTWHRPYVLLYEQILHKHVQDIAATYTTS--DKAAWVQAAANLRQPYWDWAAANAVPP-------DQVIASRKVTITGSNGH----- : 163
Tuber_melanosp  : GDYCTHGTALFITWHRPYLLLFEQRIVEEALTIARNFSDK--YRAEYEEAALNIRIPYWDWATDSDVP-------QSIRFAETDITLPEVGSDAPPVT : 168
Asp_fum_tyrosi  : PGYCVHNNVTFPTWHRPYMLLFEQRLFEIMETTIKETVPES-HKQEWRDAARQWRLPYWDFAKTSGPHATGPLSLPVLCGLANVVILNPANP----ET : 179

200         *        220         *        240         *        260         *        280         *
AXN-1           : FETIDNPLYSYKFVTTQGITSFQDQD---------GNFFPFANAMGTSRYPPQY---NSRDPTVSSQWTNGFVDND--------------SITEALRN : 251
Neurospora_cra  : TKSINNPLHRFTFHPVNPSP-----G---------DFSAAWSRYPSTVRYPN-----RLTGASRDERIAPILANEL--------------ASLRNNVS : 236
Pyrenophora_tr  : -TPMSNPLYSYQFNPISDR-----------------FDEKWRNINATIRWPNTD---DATAHSQNGMFSDAFAGQS--------------VNIVAQIG : 234
Podospora_anse  : TKSTANPIYRFVFHPVNPSP-----G---------DFPRQWSRFPTTVRYPN-----PRTGQSQDNRVAPILANEL--------------ASLRTNVS : 242
Lentinula_edod  : RISVPNPLRRYTFHPIDPS----------------FPEEPYQSWSTTLRHPLSD---DANASDNVPELKATLRSAG--------------PQLKTKTY : 230
Pycnoporus_san  : RTQVDNPLRRYRFHPIDPS----------------FPPEPYSNWPATLRHPTSD---GSDAKDNVKDLTTTLRADQ--------------PDITTKTY : 227
Pholio_nameko   : RVEVDNPLYHYKFHPIDSS----------------FPPRPYSEWPTTLRQPNSS---RPNATDNVAKLRNVLRASQ--------------ENITSNTY : 227
Tuber_melanosp  : RKGVPNPMYSYKFKTSIRRQR-DFSI---------VGVQEMVAWEETKRCPDEKGISHPEIVDRQLRIPTVNPTAG-------------SSFRDPIY : 242
Asp_fum_tyrosi  : PIELPNPVYKYRAPDLMGNLDKPFHIPPERIDPDKDDYYPWDKCQATTKYGLLKNNPHIQDAGQDVTKSNLALNEHPWYRPNKAGFPPLQTLTYEVHR : 277

300         *        320         *        340         *        360         *        380         *
AXN-1           : LSSLGEDVYRSFTTSNYAWYSSTQQSNPPADNSYQSLESIHNEIHGITGG--------------GGHMSWNTVSSFDPIFWLHHCNVDRLFAIWQAIY : 335
Neurospora_cra  : LLLLSYKDFDAFSYNRWDPNTPGD---------FGSLEDVHNEIHDRTGG--------------NGHMSSLEVSAFDPLFWLHHVNVDRLWSIWQDLN : 312
Pyrenophora_tr  : -VVFRSSTFSRFSTTLEDPHGWIHG--------IIGGGYTADAPYFG------------------HMWPLEYSAFEPLFMLHHANVDRLLALYQAAH : 304
Podospora_anse  : LLLLSYTNFDAFSNRWDPNMTPGE---------FGSLEDVHNEIHDRTGG--------------GGHMSSLDVSSFDPLFWFHHTNVDRLWAIWQDLN : 318
Lentinula_edod  : NLLTRVHTWPAFSNBTPDGGST----------SNSLEGINHDSVHVDVGG--------------NGQMSDPSVAGFDPIFFMHHAQVDRLLSWSALN : 304
Pycnoporus_san  : NLLTRVHTWPAFSNBTPGDGGSS----------SNSLEAIHDHIHDSVGG--------------GGQMSDPSVAGFDPIFFLHHCVDRLLALWSALN : 301
Pholio_nameko   : SMLTRVHTWKAFSNBTVGDGGST----------SNSLEAIHDGIHVDVGG--------------GGHMADPAVAAFDPIFFLHHCNVDRLLSLWAAIN : 301
Tuber_melanosp  : KLLTLVGSYGAFGNTGWQTGRPGPN--------NISLEHYHNIIHTFTGTNYIEENSK------EGHMSEVGVSAFDPIFWLHHCNVDRLYAIWQAIH : 326
Asp_fum_tyrosi  : LLSFKFSSWGAFASTKWCNEEENKPP-ASQQTRDILSLEYIHNNVHNWVGGTDYLGDPSKPDLQGAGHMSSVPVAAFDPIFWLYHHNVDRLTAIWGVLN : 374

400         *        420         *        440         *        460         *        480         *
AXN-1           : ADTGRYPDAWFNAQSAQLRDERGTWSIAAGSRENADTPLAPFHKDDRGSVYNSNDVRNWT---------RFGSSYPELQPWLPQYRDSTGEFNATLYR : 424
Neurospora_cra  : ------PNSFMTPRPA----PYSTFVAQEGESQSKSTPLEPFWDKSAANFWTSEQVKDS---------ITFGYAYPETQKWKYS--------SVKEYQ : 383
Pyrenophora_tr  : ------PDRWMESSNIG---PHGNVYLEDYQEVNGDTSLLPFRKTPGE-FWTPNACRNTT---------VLGYAYPETQRWQYP--------SDDSYQ : 375
Podospora_anse  : ------PDNFLTPRPA----PYSTFNSTEGESQTKDTPLTPFWDKSATKFWTSEEIKDTT---------TTFGYAYPETQEWKYR--------TGSEYQ : 390
Lentinula_edod  : ------PRVWITDGPS----GDGTWTIPPDTVVGKDTDLTPFWNTQSS-YWISANVTDTS--------KMGYTYPEFNNLDMG--------NEVAVR : 374
Pycnoporus_san  : ------PGVWVNSSSS----EDGTYTIPPDSTVDQTTALTPFWDTQST-FWTSFQSAGVS--------P8QFGYSYPEFNGLNLQ---------DQKAVK : 373
Pholio_nameko   : ------PGVWVSPGDS----EDGTFILPPEAPVDVSTPLTPFSNTDT-FWASGGITDTT--------LVGYTYPEFNGLDLG---------NAQAVK : 371
Tuber_melanosp  : ------YEAPFEDQAT-----DYTRMPLTKAIDDAETTLRPFYKDECYDVPWTSSMVQKSSAATGPTVFDYNYHYPELPVDLSG------PGKQKEMA : 407
Asp_fum_tyrosi  : ----------QDHWFD----------EPHPSDAKPDDPLKPFFHVSKDK-YFTSDDARFWR---------KYGYDYDIVKKPGTN----------EDRAP : 433
```

FIG. 3A

```
                  500         *         520         *         540         *         560         *         580
AXN-1         : NDVVAQVTDLYSRVRRRVQNTQVPRNRLFAATQTGTQTFQGSSATAGGSFAAPPTTQGFGQQLQFGPPPSGGQQAFAPPPTVQAQAQSGGQPFTPPTT : 522
Neurospora_cra: AAIRKSVTALYGSN------------------------------------------------------------VFANFVENVADRTPALKKPQA : 418
Pyrenophora_tr: NAVNSVISTLYGG-------------------------------------------------------------------------------- : 388
Podospora_anse: TSIRQAVTTLYGTN------------------------------------------------------------VFANFAA---ANVQARATEHT : 422
Lentinula_edod: SAIAAQVNKLYGG-------------------------------------------------------------PFTKFAAAIQQPSSQTTADAS : 408
Pycnoporus_san: DHIAEVVNELYGHRMRKTS-------------------------------------------------------FFPQLQAVSVAKQGDAVTPSV : 413
Pholio_nameko : AAIGNIVNRPLYGAS-----------------------------------------------------------VFSGFAAATSAIGAGSVASLA : 406
Tuber_melanosp: SHVLRRVHQLYGPP-------------------------------------------------------------------------------- : 421
Asp_fum_tyrosi: EEVKMKINQLYGEP-------------------------------------------------------------------------------- : 447

*         600         *         620         *         640         *         660         *         680
AXN-1         : LPTQGQQFTSPPPGTAQGGQFPPPPTQQQQFSPPPTHQQQFAPPPTQEHGQAVTSPPAQTQFSPPPTQAFSPPTGDSHGGQFTPQPQQQFTPQPQQQ : 620
Neurospora_cra: TGPESRSTVSAAAAHAVEL------SGARRVAEKVHNVFQHAEEKAQKPVVPVKDTKAESSTAAESLKYLAP-----D------------------ : 485
Pyrenophora_tr: ---QTRSQLTSAIETG-----------------------------------------------------SGERLLKNGN---------------- : 411
Podospora_anse: ELIKSLSLAAPPPS---------------------------------APITAEKPLLITQEMKASP--IPEHLQHLAP----N------------ : 466
Lentinula_edod: TIGNVTSDASSHLVDS------------------------KINPTFPN---RSIDDAPQVKIASTLRNNEQ--------------------- : 451
Pycnoporus_san: ATDSVSSSTTPAENPA-----------------------SREDASD----KDTEFTLNVEVAAPGAHLTS------------------------ : 456
Pholio_nameko : ADVPLEKAPAPAPEAA---------------AQSFVPAPAHVEPAVRAVSVHAAAAQPHAEPPVHVSAGGHPSP------------------- : 465
Tuber_melanosp: -TDESLVDTPKVPNALLP------------------------------------------------PSRIVRDG------------------- : 446
Asp_fum_tyrosi: ------------------------------------------------------------------ISRLHEGQP------------------ : 456

*         700         *         720         *         740         *         760         *         780
AXN-1         : QQQQFAPPQQGPGGHTPQGQHSSPPPKKSGLSGLMSSAKLHFGEALTAGREAAQGHCQPVQCHQQPTHTPGNPGSSGTALATKFGGIIGGGIHMAQER : 718
Neurospora_cra: -------------------------------------------------------------------------------------------- : -
Pyrenophora_tr: -------------------------------------------------------------------------------------------- : -
Podospora_anse: -------------------------------------------------------------------------------------------- : -
Lentinula_edod: -------------------------------------------------------------------------------------------- : -
Pycnoporus_san: -------------------------------------------------------------------------------------------- : -
Pholio_nameko : -------------------------------------------------------------------------------------------- : -
Tuber_melanosp: -------------------------------------------------------------------------------------------- : -
Asp_fum_tyrosi: -------------------------------------------------------------------------------------------- : -

*         800         *         820         *         840         *         860         *         880
AXN-1         : LGSKKQPGQPGTRGIDDEPGQEGELSRGFGDMSLGQQSFGSGESLTYHEYDANIRFERFDLGGRPFTVHIFLGDFNP-DPATWMWDKNRVGGIYNEVA : 815
Neurospora_cra: -------------------------------------------GKYTDWIVNVRAQKHGLGQ-SFRVIVFLGEFNP-DPETWDDEFNCVGRY--CGR : 535
Pyrenophora_tr: -----------------------------------SFTDWTINTQAIASKLPSTFIVKFSFVGIFQS-DPSVDAGSWMMLMPDN---- : 459
Podospora_anse: ---------------------------------NKYPEWWVNIRAQKHGLHG-AFRVIVFLGFIDESDPDSWQTEFNTVGRVSVLGR : 519
Lentinula_edod: ---------------------------------KEFWEWTARVQVKKYEIGG-SFKVLFFLGSVPS-DPKEWATDPHFVGAFHGFVN : 503
Pycnoporus_san: ---------------------------------TKYWDWTARIHVRKYEVGG-SFSVLLFLGAIPE-NPADWRTSPNYVGGHHAFVN : 508
Pholio_nameko : ---------------------------------HGFYDWTARIEFKKYEFGS-SFSVLLFLGVPE-DPEQWLVSPNFVGAHHAFVN : 517
Tuber_melanosp: ---------------------------------MFRREWLIPLRVRRYLIPG-NFIIFFFLGEPGD-DPRQWLLSENHVGAVNTFKS : 498
Asp_fum_tyrosi: ---------------------------------VEYDYVINVIYDRYALDGIPYTIVFYLHLRDGSYKCLGGVYTFSTKLSDAQDT : 509

*         900         *         920         *         940         *         960         *         980
AXN-1         : GVQRGDGSACSNCETQSQDHTIVTGQVSLTNALLDDVEDSANGLNSLIPEEVIPYLQRHLHWRITDPNGREIPR-----QSLNTLKISVVECSATISN : 908
Neurospora_cra: RAPEPQA-------------------------------------------------------------------------------------- : 542
Pyrenophora_tr: -KQNMHTLQVRTESEKVLYGTSITAHLIDLVNAGKLNSISS-------DDVVPYLRDTLTWNIFTDNGTRIAQ------PNGALTVQVTSTEAYVPE : 543
Podospora_anse: STQGPTTTKCAKCITDAADELMISGTVPLTSALLQDIVN----------ENTASIACSQRKWCRI---------------------------- : 574
Lentinula_edod: SSAER-CANCRRQQDVVLEGFVHLNEGIANISNLNSFDP----------IVVEPYLKENLHWRVQKVSGEVVNL-----DAATSLEVVVATRDELPP : 585
Pycnoporus_san: SSPQR-CANCRGQGDLVIEGFVHLNEAIARHAHLDSFDP----------TVVRPYLTRELHWGVMKVNGTVVPL-----QDVPSLEVVVLSTPLTLPP : 590
Pholio_nameko : SAAGH-CANCRMQGNVVVEGFVHLTKYISEHAGLRSLNP----------EVVEPYLTNELHWRVLKADGSVG--------QLESLEVSVYGTPMNLPV : 596
Tuber_melanosp: STDICGNCAGQGAADQLFSGGVDITNALYNKLANIGLTLD-D------QDEIEEWLAKNLKWRILKQNDKTELTSHEILENPDSLFIGVKSFVLLYPT : 589
Asp_fum_tyrosi: ERGGCDNCREQKKAGVLASAQIPLTYTLYERQEWHNLGKLLP------VKRETADIIRQHLCWKVVGVNNSILFDS------EQPMRGDPATWRSLDVT : 595

*         1000         *         1020
AXN-1         : NPGELTQYGDHRVLDIVTEGRPAGKAAGDGY---------- : 939
Neurospora_cra: ----------------------------------------- : -
Pyrenophora_tr: DRSAPIQYSENITEHPEITANRFGGTSSTSPAMMFL----- : 579
Podospora_anse: ----------------------------------------- : -
Lentinula_edod: GE-IFPVPAETHHHHHITHGRPGGSHHSVASSSS------- : 618
Pycnoporus_san: GE-PFPVPGTPVNHHDITHGRPGGSHHTH------------ : 618
Pholio_nameko : GA-MFPVPGNRRHFHGITHGRVGGSRHAIV----------- : 625
Tuber_melanosp: SRLPIDGGEFLSAPKIINEKIHFGATEPHKNRGGLGAQDPY : 630
Asp_fum_tyrosi: AAYSDIHYPVDRNYKYIDRGLPAYHNYLPIHLSPT------ : 630
```

FIG. 3B

```
                              *        20         *        40         *        60         *        80         *       100         *       120
AXN8       : ------------------------------------------------------------------------------------------------------------------------------------ :   -
TYR_AGABI  : ---------MSLIATVGFTGGVKNRLNIVDFVKNE-RFFTLYVRSLELLQAKEQHDYSSEFQLAGIHGLPFTEWAKERPSMNLYKAG---------YCTHGQVLFFTWHRTYLSVLEQILQGAAI : 106
TYR_NEUCR  : ------MSLIRTVGFTGGVKNRLNIVDFVKNE-RFFTLYVRSLELLQAKEQHDYSSEFQLAGIHGLPFTEWAKERPSMNLYKAG---------YCTHGQVLFFTWHRTYLSVLEQILQGAAI : 106
TYR_STRCA  : MSTLIKFAITGVFTPPSSNGAVPLRRELRDLQQNYPEQFNLYLIGLRDFQGLDEAKLLSYYQVAGIHGMPKFWAGVPSDTDWSQFGSSGF-------GGYCTHSSILFITWHRPYLALYEQALYASVQ : 122
AXN8       : ------------------------------MTVRKNQATLITADEKRRFVAAVLELKRSGRYDEFVRTHNEFIMSLTS-------GERTGHRSPSFLPWHRRFLLDEEQALQS--- :  76

*       140         *       160         *       180         *       200         *       220         *       240
AXN8       : ELITG-------------DEWALPIWNYLDS-------------------------SNPQALYIPDAFVAKTLPDGKPNPLN----------------------KYPRRP-------GIKAIKPVRGFSLEAMDENDFIV : 178
TYR_AGABI  : EVARKFTSN----QTLWVCAAQLLRQPYWDWG------FELMPPEVIKNEEVNITNYDGKKISVKNPLLRYHFHPILCFS-FKPYGLEATWRTIVRNPDRN----RREDIPGLIKKMRLEEGQIREKTY : 220
TYR_NEUCR  : AVAQKFPVEGGLRAKYVAAAKDFRAPYEDWASQPPKGTLAFPESLSSRTIQVVDVDGKTKSINNPLRRFTEHFVNPSFGDFSAAWSRYPSTVRYPNRLIGASRDERIAPILANELASLRNNVSLLL : 248
TYR_STRCA  : ---------V-------D------SSVI-LPYWDWS---------ADRTVRASLWAPDFLGGTGRSTDGRWMDGPFAAFTGN--------------WPINVRDSRT---YLRRSLGGSVAELFTR---AEVESVL : 160

*       260         *       280         *       300         *       320         *       340         *       360
AXN8       : GNGTIGFGGGITGNFVQFIDGVAGELETNFHNTVHGLVGG------YMGNALLAGLDPIFWLHHCNIDRIWEANMNTPGKTMVRDFLWLNGPADRSFIMFVPGDNAPGVTFTSKDTILKGGKFYRTYDD : 299
TYR_AGABI  : NMLKFNDAWERFSNHGISDDQHANSLESVHDDIHVMVGYKIEGHMDBHPFFAADFPIFWLHHIHTNVDRLLSLNKAIN---------PDVWVTSGRNRDGMGLAPNACINSETPLEPFYQS-GDRVWTS : 338
TYR_NEUCR  : LSYKDFCAFSYNRRWDPNTNPGDFGSLEDVHNEITHDRTGG------NGHMSSLEVSAFDPLFWLHHVNVDRLWSIWQDLN-----------PNSFMTRPAPYSTFVAQEESQSKSTPLEPFWDRSAANFWTS : 364
TYR_STRCA  : AISAYDLPYNSASEGFRNHLEGWRGVNLHNRVHVWVGG------QMATGVSENDPVWLHHAYVDKIWAEWQRRH------------PLSAYPIGGIPVVDLNETMKPWNTVRPADLLDHTAYYTFLA : 273

*       380         *       400         *       420         *       440         *       460         *       480         *       500
AXN8       : LIIGTGVTFGVHAVARVNMGSPSKCTVQFIGANAAVVKIGG-------------APVGTIHDLEPTAAANSMAIMGATSPFGKEVARLYLSLESLLLH---------------- : 383
TYR_AGABI  : ASLADTARLGYSYPDFDKIVGGIFRELIRDIAIDDLIDERYGS-------K-P-------S---SGARNTAFDLLALEKGITKEH---------- : 403
TYR_NEUCR  : EQVKDSIIFGYAIPETQKRWKYSSVKEYCAAIRKSVTALIYGSNVFANFVENVALCRTIPALLKKFCAIGEESRSTVSAAAAAHAVELSGARKVAERKVENVFQHAEEKAQKFVVFVKDTKAELSTAAGMNIG : 490
TYR_STRCA  : ------------------------------------------------------------------------------------------------------------------------------------ :   -

*       520         *       540         *       560         *       580         *       600         *       620
AXN8       : ------------------------------------------------------------------------------------------------------------------------------------ :   -
TYR_AGABI  : ----------KEDLKMYDWTIHVAEKKFELKESFSLLFYASDGGD----YDQENCFVGSINAFRGTAPETCANCQDN---ENLIQEGFIHLNHYLAR------DLESFEPQVHK : 496
TYR_NEUCR  : LSIKRPSKIITASPGPIPESLKYIAPDGKRYTDWIYNVRAQKHGLGQSFRVIVFLGEFNPDPEIWLDEFNCVGRYSVLGRSAEITQCGKCRKDNANGLIVSGTVPLTSALLQDIVGGELQSLRPEDVIP : 616
TYR_STRCA  : ------------------------------------------------------------------------------------------------------------------------------------ :   -

*       640         *       660         *       680         *       700
AXN8       : ------------------------------------------------------------------------------- :   -
TYR_AGABI  : FLKE-------RGLSYRLYSRGDKPLTLSLSVRIEGRPLHLPEG--EHRPKYDHTQARVFDDVAVHVIN : 556
TYR_NEUCR  : HLRANLKWKVALFNGDEYNLEEVPDLKVSVASTEVTIDEEGLPHYSRQYTVYPEITEGKPCGHGPEDHI : 685
TYR_STRCA  : ------------------------------------------------------------------------------- :   -
```

FIG. 4

```
                  *        20         *        40         *
AXN-9 : MNTIRQDVATLGSGWDNKVLLNYALAMRELDKLPITNRNSWKFLGAIHGF :  50
AXN-8 : MSTSRQDVAKLGPGWN-KVLLNYALAMQALDEQPIADRNSWKFLGAMHGF :  49

60         *        80         *        100
AXN-9 : DRQLWVEVNVLGDSDPVPKDLTNFTYGSQCQHGSWYFLSWHRGYLAAFEA : 100
AXN-8 : HPQLWINERLIKSGAPIPADLTNHTYGNQCQHGSWYFLSWHRAYLFAFEA :  99

*        120        *        140        *
AXN-9 : IVAAKVKELTGDDWALPYWNYLNSKNPDARRAPEAFLADTLPDGSPNPLK : 150
AXN-8 : IVAAKVKELTGDDWALPYWNYLDSSNPQALYLPDAFVAKTLPDGKPNPLN : 149

160        *        180        *        200
AXN-9 : KYPRRQGFTTLRPNSLDAFSLAAMQENDFQVGNDGSIGFGGGVTGNFAQF : 200
AXN-8 : KYPRRPGIKAIKP--VRGFSLEAMDENDFIVGN-GTLGFGGGITGNFVQF : 196

*        220        *        240        *
AXN-9 : ARWTGDLENNPHNTVHRLIGGGEGFMADPYLAALDPIFWLHHCNVDRLWE : 250
AXN-8 : DGVAGELETNPHNTVHGLVG---GYMGNALLAGLDPIFWLHHCNIDRLWE : 243

260        *        280        *        300
AXN-9 : AWMNTPGKTMVRDPRWLDGPADRRFIMPTVGGSDPGMKFTGRDTLKDGKL : 300
AXN-8 : AWMNTPGKTMVRDPLWLNGPADRSFIMPVPGDNAPGVTFTSKDTLKGGKF : 293

*        320        *        340        *
AXN-9 : HPRYADLSIGTGVKPGVEAVTRVKMGAPEQQNIEPIGANRSVVTVGGAPV : 350
AXN-8 : YRTYDDLIIGTGVTPGVHAVARVNMGSPSKQTVQPIGANAAVVKIGGAPV : 343

360        *        380        *        400
AXN-9 : RTQVDLDRQATSTGIAAMGATDLGQPVTRLYLALESVRGSAPSPQLTVYI : 400
AXN-8 : GTHIDLEPTAAANSMATMGATSPGKEVARLYLSLESVRGSAPSPLLDVYV : 393

*        420        *        440        *
AXN-9 : NLPKDSDPQQHPECHAGSLTLFGLNVASRPDGGHGGHGLGYTIDITDLAQ : 450
AXN-8 : NLPEGADPALSPDRYAGSLTLFGLNVASQTDGPHAGSGLGYTIDITDLAQ : 443

460        *        480        *
AXN-9 : RLTDAGDFDPDYLRVTLVPGEQVSADKPVTVERISVLKRSGIVS : 494
AXN-8 : RLADAGDFDPNHLRVTLVPGEQITDEEPITVERISVLKRSGIVS : 487
```

FIG. 5

SEQUENCE LISTING

<160> NUMBER OF SEQ ID NOS: 48

<210> SEQ ID NO 1
<211> LENGTH: 3769
<212> TYPE: DNA
<213> ORGANISM: Arthrobotrys oligospora

<400> SEQUENCE: 1

```
tccgacgacg ttgcagtttc caacatggca tcagcaccat acgctatcac gggcattcca      60
actaccagag ccctgatgg agccctcccg cttcgtcaag agattgatgc ttggtctgcg     120
aacccagcca atgttgacca ggtgaactta tatctccagg cgcttgctgc tttccaacag     180
ttgcctgcga cagataagct ctcttacttc cagattgctg gttagtccga tcaaccgtta     240
cttctcttat ccattgagat tccttggcta attgcgattt tttgttgttg tagggattca     300
tggtatgaat ggtatcaata ttggtatctt ggatagatat actaatttat cttaaaaaaa     360
ggggagcctt ttatcccgtg ggatgagaat accagtccta atccaagatc taggtggaga     420
ggtcagtata ttggtcctat tactctatat gtttttatat tccaataaac taaccaagtt     480
attgaataca ggatattgta cacatgcatc aatcctcttc ccgtaagcat aaaaacccag     540
ggccgaattt cttgtcgcgg accggatatt agtctaactt aagatacaat agaacatggc     600
atcggccgta tctcgctgtc ttcgaggtat ataatttcta cctaaaggaa aaatctttcg     660
tagatagtta acgcttgatt tcgatattta tagcaaatcc ttcattcgat tatgcagcga     720
attgcggcag catatccaga ccaagagctt cgaacccgat atcagactgc cgcagaagca     780
```

-continued

```
ttccgtattc catactggga cagtgcacaa cttaaggaac gtgggggcag aagatccttg    840
aacgttcctt acctttgcac cttgcctact gttcaagtct tcactcctac ttccgctgga    900
gatactatca ggccttttga aactattgat aatcccttgt acagctacaa atttgtcacc    960
acacaaggaa ttactagttt ccaagaccag gatggaaatt tctttccagt aatagaaaca   1020
tccattctcc aggattcact acgtggattg tcactaataa gcattcgatt ggtagttcgc   1080
aaacgcgatg ggaacttccc gctatccacc acaatacaat tctcgcgacc ccaccgtttc   1140
ttctcagtgg accaatggat tcgttgataa cgactcgatc acggaggcac tacggaatct   1200
gagttctctt ggtgaggacg tttaccgatc attcacgacc agcaattatg cctggtactc   1260
tagcacccaa caatcaaatc ccccagcgcc aacaggtat gaaacttgaa atgtaaatat    1320
actagtaaat accagtctca ctggctaatc ttatccaaca cttagctacc aatctctcga   1380
atcgattcac aatgaaatcc acggcatcac aggaggggt ggacatatga gctggaatac    1440
gtaagtcgta tgaacctgac attaaaatta aaaatctacg ttagctaata tacctaactt   1500
cgcacactca gagtttcatc ttttggtatg gattctacca attcattgat gcttttttat   1560
acttgctaac ttgtattcct cagatcctat tttctggctc caccactgca acgtggatcg   1620
tctgtttgcc atctggcaag ctatctacgc tgataccggc cgatatcctg atgcttggtt   1680
taatgcacaa tcagcacaac ttcgagacga acgaggaact tggtcgattg ctgcaggttc   1740
tcgcgaaaat gctgacactc cactagctcc attccataag gacgacagag gcagcgtcta   1800
caattccaat gacgtccgca attggactag gtttggctct tcgtaccctg aattgcaacc   1860
atggcttcct caataccgag attccactgg tgaatttaac gcaacgctat atcgtaacga   1920
tgttgttgca caggtcaccg acttgtattc gcgagtcaga aggcgtgtcc agaacactca   1980
agttccacga aatcgccttt ttgctgccac ccagaccggc acccagacat tccaaggcag   2040
ttccgctact gcaggcgggt cgtttgcggc cccaccgaca acacaagggc ccggtcagca   2100
gttgcaattt ggtcccccte cttccggcgg gcaacaggcc ttcgcccctc caccaacagt   2160
ccaagcccaa gccagtctc aaggacaacc attcaccccg ccaacgacgc tgcccactca    2220
gggacagcaa tttacctctc ctcctcctca aactgctcag ggccaacagt tcccacccc    2280
gccgactcag cagcaacagt tctcgccgcc gccgactcat cagcagcaat tcgcccctcc   2340
tcctacgcag gagcacggac aggcggttac gtcaccacct gcacagacac aattctcccc   2400
tccgccaact caggcattct cgccgccacc gactggtgat tcccacggac agcagtttac   2460
tccacagccg caacagcaat tcactccaca accgcaacag caacagcaac agcaatttgc   2520
gcctccccag caaggaccag gcggccatac cccacaggga cagcatagct ctccaccacc   2580
caagaaaagc ggcctcagtg gccttatgtc tctctgctaaa ctgcactttg gtgaagccct   2640
tactgcaggc cgtgaagccg ctcaaggcca ccagcagcct gtacaacagc atcaacagcc   2700
cactcacact ccaggaaacc ctggcagcag tggtactgct cttgctacta aatttggtgg   2760
tattattgga ggcggtattc atatggccca agaacgtctt ggttctaaga agcagccggg   2820
ccaacctgga acccgtggta ttgatgacga acctggtcaa gaaggagaat tgagccgtgg   2880
attcggtgat atgagcttgg gccaacaaag tttcggctca ggagagtcgc ttacttacca   2940
cgaatacgat gcaaacatcc gatttgagag gtaaactgcg taacaaccaa agaaccccca   3000
agtatcaagc cgctaacctt agaaatatag attcgacctc ggtggtcgtc cattcacagt   3060
ccacatcttc cttggagact tcaacccgga cccagcaact tggatgtggg acaagaatcg   3120
tgtcggtgga atctataact ttgtcgccgg tgttcagcgt ggagacggaa gcgcttgctc   3180
```

```
caactgcgaa actcaatccc aggaccacac tatcgttacg ggtcaggtgt ctctcactaa    3240
cgcccttctt gacgacgttg aagactcagc aaatggcttg aatagcctga ttcccgagga    3300
ggttatcccg tatttgcaac gacatctgca ctggcgtatc actgacgtat gttgatccct    3360
cccaaagttc actttatatt gttctcaatt gttaactaac acgtggggaa attagccgaa    3420
tggaagggag atcccacgcc agagcctcaa taccttaaag atctctgttg ttgaatgttc    3480
cgccaccatt tcaaacaacc ccggcgagct cacccaatat ggggatcaca gagtcttgga    3540
catagttact gaaggtcgtc cggctggcaa agcggctggc gatggttact aaaaaaaatc    3600
tagtgaaccc tttcagcata ttgcacgcag attgctgttt tgtttgtttt atgtaggtca    3660
ttcgaattcg acgaccctga aatttgcttc acgagcatta aatcagagag ggaaatagtg    3720
aatattaacc gctgggcgag cgtcttttca tgtttatgta cttaggcag                3769
```

<210> SEQ ID NO 2
<211> LENGTH: 3094
<212> TYPE: DNA
<213> ORGANISM: Arthrobotrys oligospora

<400> SEQUENCE: 2

```
tccgacgacg ttgcagtttc aacatggca tcagcaccat acgctatcac gggcattcca     60
actaccagag cccctgatgg agccctcccg cttcgtcaag agattgatgc ttggtctgcg    120
aacccagcca atgttgacca ggtgaactta tatctccagg cgcttgctgc tttccaacag    180
ttgcctgcga cagataagct ctcttacttc cagattgctg ggattcatgg ggagcctttt    240
atcccgtggg atgagaatac cagtcctaat ccaagatcta ggtggagagg atattgtaca    300
catgcatcaa tcctcttccc aacatggcat cggccgtatc tcgctgtctt cgagcaaatc    360
cttcattcga ttatgcagcg aattgcggca gcatatccag accaagagct tcgaacccga    420
tatcagactg ccgcagaagc attccgtatt ccatactggg acagtgcaca acttaaggaa    480
cgtgggggca gaagatcctt gaacgttcct tacctttgca ccttgcctac tgttcaagtc    540
ttcactccta cttccgctgg agatactatc aggccttttg aaactattga taatcccttg    600
tacagctaca aatttgtcac cacacaagga attactagtt tccaagacca ggatggaaat    660
ttctttccat tcgcaaacgc gatgggaact tcccgctatc caccacaata caattctcgc    720
gaccccaccg tttcttctca gtggaccaat ggattcgttg ataacgactc gatcacggag    780
gcactacgga atctgagttc tcttggtgag gacgtttacc gatcattcac gaccagcaat    840
tatgcctggt actctagcac ccaacaatca aatccccag cgcccaacag ctaccaatct    900
ctcgaatcga ttcacaatga aatccacggc atcacaggag ggggtggaca tatgagctgg    960
aatacagttt catcttttga tcctatttc tggctccacc actgcaacgt ggatcgtctg   1020
tttgccatct ggcaagctat ctacgctgat accggccgat atcctgatgc ttggtttaat   1080
gcacaatcag cacaacttcg agacgaacga ggaacttggt cgattgctgc aggttctcgc   1140
gaaaatgctg acactccact agctccattc cataaggacg acagaggcag cgtctacaat   1200
tccaatgacg tccgcaattg gactaggttt ggctcttcgt accctgaatt gcaaccatgg   1260
cttcctcaat accgagattc cactggtgaa tttaacgcaa cgctatatcg taacgatgtt   1320
gttgcacagg tcaccgactt gtattcgcga gtcagaaggc gtgtccagaa cactcaagtt   1380
ccacgaaatc gccttttttgc tgccacccag accggcaccc agacattcca aggcagttcc   1440
gctactgcag gcgggtcgtt tgcggcccca ccgacaacac aagggcccgg tcagcagttg   1500
caatttggtc cccctccttc cggcgggcaa caggccttcg cccctccacc aacagtccaa   1560
```

-continued

```
gcccaagccc agtctcaagg acaaccattc accccgccaa cgacgctgcc cactcaggga    1620
cagcaattta cctctcctcc tcctcaaact gctcagggcc aacagttccc accccgccg     1680 actcagcagc aacagttctc gccgccgccg actcatcagc agcaattcgc cctcctcct     1740 acgcaggagc acggacaggc ggttacgtca ccacctgcac agacacaatt ctcccctccg    1800
ccaactcagg cattctcgcc gccaccgact ggtgattccc acggacagca gtttactcca    1860
cagccgcaac agcaattcac tccacaaccg caacagcaac agcaacagca atttgcgcct    1920
ccccagcaag gaccaggcgg ccatacccca cagggacagc atagctctcc accacccaag    1980
aaaagcggcc tcagtggcct tatgtcctct gctaaactgc actttggtga agcccttact    2040
gcaggccgtg aagccgctca aggccaccag cagcctgtac aacagcatca acagcccact    2100
cacactccag aaaccctggc agcagtggt actgctcttg ctactaaatt tggtggtatt     2160
attggaggcg gtattcatat ggcccaagaa cgtcttggtt ctaagaagca gccgggccaa    2220
cctggaaccc gtggtattga tgacgaacct ggtcaagaag gagaattgag ccgtggattc    2280
ggtgatatga gcttgggcca acaaagtttc ggctcaggag agtcgcttac ttaccacgaa    2340
tacgatgcaa acatccgatt tgagagattc gacctcggtg gtcgtccatt cacagtccac    2400
atcttccttg agacttcaa cccggaccca gcaacttgga tgtgggacaa gaatcgtgtc     2460
ggtggaatct ataactttgt cgccggtgtt cagcgtggac acgaagcgc ttgctccaac     2520 tgcgaaactc aatcccagga ccacactatc gttacgggtc aggtgtctct cactaacgcc    2580
cttcttgacg acgttgaaga ctcagcaaat ggcttgaata gcctgattcc cgaggaggtt    2640
atcccgtatt tgcaacgaca tctgcactgg cgtatcactg accgaatgg aagggagatc     2700 ccacgccaga gcctcaatac cttaaagatc tctgttgttg aatgttccgc caccatttca    2760
aacaaccccg gcgagctcac ccaatatggg gatcacagag tcttggacat agttactgaa    2820
ggtcgtccgg ctggcaaagc ggctggcgat ggttactaaa aaaaatctag tgaacccttt    2880
cagcatattg cacgcagatt gctgttttgt ttgttttatg tagggcattc gaattcgacg    2940
accctgaaat ttgcttcacg agcattaaat cagagaggga aatagtgaat attaaccgct    3000
gggcgagcgt ctttcatgt ttatgtactt aggcagttgc ctgtttttgc tggaatatat     3060
tttaattgag tcccaaaaaa aaaaaaaaaa aaaa                                3094
```

<210> SEQ ID NO 3
<211> LENGTH: 2835
<212> TYPE: DNA
<213> ORGANISM: Arthrobotrys oligospora
<220> FEATURE:
<221> NAME/KEY: CDS
<222> LOCATION: (1)...(2835)

<400> SEQUENCE: 3

```
atg gca tca gca cca tac gct atc acg ggc att cca act acc aga gcc         48
Met Ala Ser Ala Pro Tyr Ala Ile Thr Gly Ile Pro Thr Thr Arg Ala
1               5                   10                  15 cct gat gga gcc ctc ccg ctt cgt caa gag att gat gct tgg tct gcg         96
Pro Asp Gly Ala Leu Pro Leu Arg Gln Glu Ile Asp Ala Trp Ser Ala
            20                  25                  30 aac cca gcc aat gtt gac cag gtg aac tta tat ctc cag gcg ctt gct        144
Asn Pro Ala Asn Val Asp Gln Val Asn Leu Tyr Leu Gln Ala Leu Ala
        35                  40                  45 gct ttc caa cag ttg cct gcg aca gat aag ctc tct tac ttc cag att        192
Ala Phe Gln Gln Leu Pro Ala Thr Asp Lys Leu Ser Tyr Phe Gln Ile
    50                  55                  60
```

```
gct ggg att cat ggg gag cct ttt atc ccg tgg gat gag aat acc agt      240
Ala Gly Ile His Gly Glu Pro Phe Ile Pro Trp Asp Glu Asn Thr Ser
65                  70                  75                  80 cct aat cca aga tct agg tgg aga gga tat tgt aca cat gca tca atc      288
Pro Asn Pro Arg Ser Arg Trp Arg Gly Tyr Cys Thr His Ala Ser Ile
                85                  90                  95 ctc ttc cca aca tgg cat cgg ccg tat ctc gct gtc ttc gag caa atc      336
Leu Phe Pro Thr Trp His Arg Pro Tyr Leu Ala Val Phe Glu Gln Ile
            100                 105                 110 ctt cat tcg att atg cag cga att gcg gca gca tat cca gac caa gag      384
Leu His Ser Ile Met Gln Arg Ile Ala Ala Ala Tyr Pro Asp Gln Glu
        115                 120                 125 ctt cga acc cga tat cag act gcc gca gaa gca ttc cgt att cca tac      432
Leu Arg Thr Arg Tyr Gln Thr Ala Ala Glu Ala Phe Arg Ile Pro Tyr
    130                 135                 140 tgg gac agt gca caa ctt aag gaa cgt ggg ggc aga aga tcc ttg aac      480
Trp Asp Ser Ala Gln Leu Lys Glu Arg Gly Gly Arg Arg Ser Leu Asn
145                 150                 155                 160 gtt cct tac ctt tgc acc ttg cct act gtt caa gtc ttc act cct act      528
Val Pro Tyr Leu Cys Thr Leu Pro Thr Val Gln Val Phe Thr Pro Thr
                165                 170                 175 tcc gct gga gat act atc agg cct ttt gaa act att gat aat ccc ttg      576
Ser Ala Gly Asp Thr Ile Arg Pro Phe Glu Thr Ile Asp Asn Pro Leu
            180                 185                 190 tac agc tac aaa ttt gtc acc aca caa gga att act agt ttc caa gac      624
Tyr Ser Tyr Lys Phe Val Thr Thr Gln Gly Ile Thr Ser Phe Gln Asp
        195                 200                 205 cag gat gga aat ttc ttt cca ttc gca aac gcg atg gga act tcc cgc      672
Gln Asp Gly Asn Phe Phe Pro Phe Ala Asn Ala Met Gly Thr Ser Arg
    210                 215                 220 tat cca cca caa tac aat tct cgc gac ccc acc gtt tct tct cag tgg      720
Tyr Pro Pro Gln Tyr Asn Ser Arg Asp Pro Thr Val Ser Ser Gln Trp
225                 230                 235                 240 acc aat gga ttc gtt gat aac gac tcg atc acg gag gca cta cgg aat      768
Thr Asn Gly Phe Val Asp Asn Asp Ser Ile Thr Glu Ala Leu Arg Asn
                245                 250                 255 ctg agt tct ctt ggt gag gac gtt tac cga tca ttc acg acc agc aat      816
Leu Ser Ser Leu Gly Glu Asp Val Tyr Arg Ser Phe Thr Thr Ser Asn
            260                 265                 270 tat gcc tgg tac tct agc acc caa caa tca aat ccc cca gcg ccc aac      864
Tyr Ala Trp Tyr Ser Ser Thr Gln Gln Ser Asn Pro Pro Ala Pro Asn
        275                 280                 285 agc tac caa tct ctc gaa tcg att cac aat gaa atc cac ggc atc aca      912
Ser Tyr Gln Ser Leu Glu Ser Ile His Asn Glu Ile His Gly Ile Thr
    290                 295                 300 gga ggg ggt gga cat atg agc tgg aat aca gtt tca tct ttt gat cct      960
Gly Gly Gly Gly His Met Ser Trp Asn Thr Val Ser Ser Phe Asp Pro
305                 310                 315                 320 att ttc tgg ctc cac cac tgc aac gtg gat cgt ctg ttt gcc atc tgg     1008
Ile Phe Trp Leu His His Cys Asn Val Asp Arg Leu Phe Ala Ile Trp
                325                 330                 335 caa gct atc tac gct gat acc ggc cga tat cct gat gct tgg ttt aat     1056
Gln Ala Ile Tyr Ala Asp Thr Gly Arg Tyr Pro Asp Ala Trp Phe Asn
            340                 345                 350 gca caa tca gca caa ctt cga gac gaa cga gga act tgg tcg att gct     1104
Ala Gln Ser Ala Gln Leu Arg Asp Glu Arg Gly Thr Trp Ser Ile Ala
        355                 360                 365 gca ggt tct cgc gaa aat gct gac act cca cta gct cca ttc cat aag     1152
Ala Gly Ser Arg Glu Asn Ala Asp Thr Pro Leu Ala Pro Phe His Lys
    370                 375                 380
```

```
gac gac aga ggc agc gtc tac aat tcc aat gac gtc cgc aat tgg act       1200
Asp Asp Arg Gly Ser Val Tyr Asn Ser Asn Asp Val Arg Asn Trp Thr
385                 390                 395                 400 agg ttt ggc tct tcg tac cct gaa ttg caa cca tgg ctt cct caa tac       1248
Arg Phe Gly Ser Ser Tyr Pro Glu Leu Gln Pro Trp Leu Pro Gln Tyr
                405                 410                 415 cga gat tcc act ggt gaa ttt aac gca acg cta tat cgt aac gat gtt       1296
Arg Asp Ser Thr Gly Glu Phe Asn Ala Thr Leu Tyr Arg Asn Asp Val
            420                 425                 430 gtt gca cag gtc acc gac ttg tat tcg cga gtc aga agg cgt gtc cag       1344
Val Ala Gln Val Thr Asp Leu Tyr Ser Arg Val Arg Arg Arg Val Gln
        435                 440                 445 aac act caa gtt cca cga aat cgc ctt ttt gct gcc acc cag acc ggc       1392
Asn Thr Gln Val Pro Arg Asn Arg Leu Phe Ala Ala Thr Gln Thr Gly
    450                 455                 460 acc cag aca ttc caa ggc agt tcc gct act gca ggg ggg tcg ttt gcg       1440
Thr Gln Thr Phe Gln Gly Ser Ser Ala Thr Ala Gly Gly Ser Phe Ala
465                 470                 475                 480 gcc cca ccg aca aca caa ggg ccc ggt cag cag ttg caa ttt ggt ccc       1488
Ala Pro Pro Thr Thr Gln Gly Pro Gly Gln Gln Leu Gln Phe Gly Pro
                485                 490                 495 cct cct tcc ggc ggg caa cag gcc ttc gcc cct cca cca aca gtc caa       1536
Pro Pro Ser Gly Gly Gln Gln Ala Phe Ala Pro Pro Pro Thr Val Gln
            500                 505                 510 gcc caa gcc cag tct caa gga caa cca ttc acc ccg cca acg acg ctg       1584
Ala Gln Ala Gln Ser Gln Gly Gln Pro Phe Thr Pro Pro Thr Thr Leu
        515                 520                 525 ccc act cag gga cag caa ttt acc tct cct cct cct caa act gct cag       1632
Pro Thr Gln Gly Gln Gln Phe Thr Ser Pro Pro Pro Gln Thr Ala Gln
    530                 535                 540 ggc caa cag ttc cca ccc ccg act cag cag caa cag ttc tcg ccg           1680
Gly Gln Gln Phe Pro Pro Pro Thr Gln Gln Gln Gln Phe Ser Pro
545                 550                 555                 560 ccg ccg act cat cag cag caa ttc gcc cct cct cct acg cag gag cac       1728
Pro Pro Thr His Gln Gln Gln Phe Ala Pro Pro Pro Thr Gln Glu His
                565                 570                 575 gga cag gcg gtt acg tca cca cct gca cag aca caa ttc tcc cct ccg       1776
Gly Gln Ala Val Thr Ser Pro Pro Ala Gln Thr Gln Phe Ser Pro Pro
            580                 585                 590 cca act cag gca ttc tcg ccg cca ccg act ggt gat tcc cac gga cag       1824
Pro Thr Gln Ala Phe Ser Pro Pro Thr Gly Asp Ser His Gly Gln
        595                 600                 605 cag ttt act cca cag ccg caa cag caa ttc act cca caa ccg caa cag       1872
Gln Phe Thr Pro Gln Pro Gln Gln Gln Phe Thr Pro Gln Pro Gln Gln
    610                 615                 620 caa cag caa cag caa ttt gcg cct ccc cag caa gga cca ggc ggc cat       1920
Gln Gln Gln Gln Gln Phe Ala Pro Pro Gln Gln Gly Pro Gly Gly His
625                 630                 635                 640 acc cca cag gga cag cat agc tct cca cca ccc aag aaa agc ggc ctc       1968
Thr Pro Gln Gly Gln His Ser Ser Pro Pro Lys Lys Ser Gly Leu
                645                 650                 655 agt ggc ctt atg tcc tct gct aaa ctg cac ttt ggt gaa gcc ctt act       2016
Ser Gly Leu Met Ser Ser Ala Lys Leu His Phe Gly Glu Ala Leu Thr
            660                 665                 670 gca ggc cgt gaa gcc gct caa ggc cac cag cag cct gta caa cag cat       2064
Ala Gly Arg Glu Ala Ala Gln Gly His Gln Gln Pro Val Gln Gln His
        675                 680                 685 caa cag ccc act cac act cca gga aac cct ggc agc agt ggt act gct       2112
Gln Gln Pro Thr His Thr Pro Gly Asn Pro Gly Ser Ser Gly Thr Ala
    690                 695                 700
```

```
ctt gct act aaa ttt ggt ggt att att gga ggc ggt att cat atg gcc    2160
Leu Ala Thr Lys Phe Gly Gly Ile Ile Gly Gly Gly Ile His Met Ala
705                 710                 715                 720 caa gaa cgt ctt ggt tct aag aag cag ccg ggc caa cct gga acc cgt    2208
Gln Glu Arg Leu Gly Ser Lys Lys Gln Pro Gly Gln Pro Gly Thr Arg
            725                 730                 735 ggt att gat gac gaa cct ggt caa gaa gga gaa ttg agc cgt gga ttc    2256
Gly Ile Asp Asp Glu Pro Gly Gln Glu Gly Glu Leu Ser Arg Gly Phe
        740                 745                 750 ggt gat atg agc ttg ggc caa caa agt ttc ggc tca gga gag tcg ctt    2304
Gly Asp Met Ser Leu Gly Gln Gln Ser Phe Gly Ser Gly Glu Ser Leu
    755                 760                 765 act tac cac gaa tac gat gca aac atc cga ttt gag aga ttc gac ctc    2352
Thr Tyr His Glu Tyr Asp Ala Asn Ile Arg Phe Glu Arg Phe Asp Leu
770                 775                 780 ggt ggt cgt cca ttc aca gtc cac atc ttc ctt gga gac ttc aac ccg    2400
Gly Gly Arg Pro Phe Thr Val His Ile Phe Leu Gly Asp Phe Asn Pro
785                 790                 795                 800 gac cca gca act tgg atg tgg gac aag aat cgt gtc ggt gga atc tat    2448
Asp Pro Ala Thr Trp Met Trp Asp Lys Asn Arg Val Gly Gly Ile Tyr
            805                 810                 815 aac ttt gtc gcc ggt gtt cag cgt gga gac gga agc gct tgc tcc aac    2496
Asn Phe Val Ala Gly Val Gln Arg Gly Asp Gly Ser Ala Cys Ser Asn
        820                 825                 830 tgc gaa act caa tcc cag gac cac act atc gtt acg ggt cag gtg tct    2544
Cys Glu Thr Gln Ser Gln Asp His Thr Ile Val Thr Gly Gln Val Ser
    835                 840                 845 ctc act aac gcc ctt ctt gac gac gtt gaa gac tca gca aat ggc ttg    2592
Leu Thr Asn Ala Leu Leu Asp Asp Val Glu Asp Ser Ala Asn Gly Leu
850                 855                 860 aat agc ctg att ccc gag gag gtt atc ccg tat ttg caa cga cat ctg    2640
Asn Ser Leu Ile Pro Glu Glu Val Ile Pro Tyr Leu Gln Arg His Leu
865                 870                 875                 880 cac tgg cgt atc act gac ccg aat gga agg gag atc cca cgc cag agc    2688
His Trp Arg Ile Thr Asp Pro Asn Gly Arg Glu Ile Pro Arg Gln Ser
            885                 890                 895 ctc aat acc tta aag atc tct gtt gtt gaa tgt tcc gcc acc att tca    2736
Leu Asn Thr Leu Lys Ile Ser Val Val Glu Cys Ser Ala Thr Ile Ser
        900                 905                 910 aac aac ccc ggc gag ctc acc caa tat ggg gat cac aga gtc ttg gac    2784
Asn Asn Pro Gly Glu Leu Thr Gln Tyr Gly Asp His Arg Val Leu Asp
    915                 920                 925 ata gtt act gaa ggt cgt ccg gct ggc aaa gcg gct ggc gat ggt tac    2832
Ile Val Thr Glu Gly Arg Pro Ala Gly Lys Ala Ala Gly Asp Gly Tyr
930                 935                 940 taa                                                                 2835

<210> SEQ ID NO 4
<211> LENGTH: 944
<212> TYPE: PRT
<213> ORGANISM: Arthrobotrys oligospora

<400> SEQUENCE: 4

Met Ala Ser Ala Pro Tyr Ala Ile Thr Gly Ile Pro Thr Thr Arg Ala
1               5                   10                  15

Pro Asp Gly Ala Leu Pro Leu Arg Gln Glu Ile Asp Ala Trp Ser Ala
            20                  25                  30

Asn Pro Ala Asn Val Asp Gln Val Asn Leu Tyr Leu Gln Ala Leu Ala
        35                  40                  45

Ala Phe Gln Gln Leu Pro Ala Thr Asp Lys Leu Ser Tyr Phe Gln Ile
```

```
              50                  55                  60
Ala Gly Ile His Gly Glu Pro Phe Ile Pro Trp Asp Glu Asn Thr Ser
 65                  70                  75                  80

Pro Asn Pro Arg Ser Arg Trp Arg Gly Tyr Cys Thr His Ala Ser Ile
                 85                  90                  95

Leu Phe Pro Thr Trp His Arg Pro Tyr Leu Ala Val Phe Glu Gln Ile
                100                 105                 110

Leu His Ser Ile Met Gln Arg Ile Ala Ala Tyr Pro Asp Gln Glu
            115                 120                 125

Leu Arg Thr Arg Tyr Gln Thr Ala Ala Glu Ala Phe Arg Ile Pro Tyr
            130                 135                 140

Trp Asp Ser Ala Gln Leu Lys Glu Arg Gly Arg Arg Ser Leu Asn
145                 150                 155                 160

Val Pro Tyr Leu Cys Thr Leu Pro Thr Val Gln Val Phe Thr Pro Thr
                165                 170                 175

Ser Ala Gly Asp Thr Ile Arg Pro Phe Glu Thr Ile Asp Asn Pro Leu
                180                 185                 190

Tyr Ser Tyr Lys Phe Val Thr Thr Gln Gly Ile Thr Ser Phe Gln Asp
            195                 200                 205

Gln Asp Gly Asn Phe Phe Pro Phe Ala Asn Ala Met Gly Thr Ser Arg
    210                 215                 220

Tyr Pro Pro Gln Tyr Asn Ser Arg Asp Pro Thr Val Ser Ser Gln Trp
225                 230                 235                 240

Thr Asn Gly Phe Val Asp Asn Asp Ser Ile Thr Glu Ala Leu Arg Asn
                245                 250                 255

Leu Ser Ser Leu Gly Glu Asp Val Tyr Arg Ser Phe Thr Thr Ser Asn
            260                 265                 270

Tyr Ala Trp Tyr Ser Ser Thr Gln Gln Ser Asn Pro Pro Ala Pro Asn
            275                 280                 285

Ser Tyr Gln Ser Leu Glu Ser Ile His Asn Glu Ile His Gly Ile Thr
    290                 295                 300

Gly Gly Gly Gly His Met Ser Trp Asn Thr Val Ser Ser Phe Asp Pro
305                 310                 315                 320

Ile Phe Trp Leu His His Cys Asn Val Asp Arg Leu Phe Ala Ile Trp
                325                 330                 335

Gln Ala Ile Tyr Ala Asp Thr Gly Arg Tyr Pro Asp Ala Trp Phe Asn
            340                 345                 350

Ala Gln Ser Ala Gln Leu Arg Asp Glu Arg Gly Thr Trp Ser Ile Ala
            355                 360                 365

Ala Gly Ser Arg Glu Asn Ala Asp Thr Pro Leu Ala Pro Phe His Lys
370                 375                 380

Asp Asp Arg Gly Ser Val Tyr Asn Ser Asn Asp Val Arg Asn Trp Thr
385                 390                 395                 400

Arg Phe Gly Ser Ser Tyr Pro Glu Leu Gln Pro Trp Leu Pro Gln Tyr
                405                 410                 415

Arg Asp Ser Thr Gly Glu Phe Asn Ala Thr Leu Tyr Arg Asn Asp Val
            420                 425                 430

Val Ala Gln Val Thr Asp Leu Tyr Ser Arg Val Arg Arg Val Gln
            435                 440                 445

Asn Thr Gln Val Pro Arg Asn Arg Leu Phe Ala Ala Thr Gln Thr Gly
    450                 455                 460

Thr Gln Thr Phe Gln Gly Ser Ser Ala Thr Ala Gly Gly Ser Phe Ala
465                 470                 475                 480
```

```
Ala Pro Pro Thr Thr Gln Gly Pro Gly Gln Gln Leu Gln Phe Gly Pro
                485                 490                 495

Pro Pro Ser Gly Gly Gln Gln Ala Phe Ala Pro Pro Thr Val Gln
        500                 505                 510

Ala Gln Ala Gln Ser Gln Gly Gln Pro Phe Thr Pro Pro Thr Thr Leu
            515                 520                 525

Pro Thr Gln Gly Gln Gln Phe Thr Ser Pro Pro Gln Thr Ala Gln
        530                 535                 540

Gly Gln Gln Phe Pro Pro Pro Thr Gln Gln Gln Gln Phe Ser Pro
545                 550                 555                 560

Pro Pro Thr His Gln Gln Phe Ala Pro Pro Thr Gln Glu His
                565                 570                 575

Gly Gln Ala Val Thr Ser Pro Pro Ala Gln Thr Gln Phe Ser Pro Pro
            580                 585                 590

Pro Thr Gln Ala Phe Ser Pro Pro Thr Gly Asp Ser His Gly Gln
        595                 600                 605

Gln Phe Thr Pro Gln Pro Gln Gln Phe Thr Pro Gln Pro Gln Gln
        610                 615                 620

Gln Gln Gln Gln Gln Phe Ala Pro Pro Gln Gln Gly Pro Gly Gly His
625                 630                 635                 640

Thr Pro Gln Gly Gln His Ser Ser Pro Pro Lys Lys Ser Gly Leu
                645                 650                 655

Ser Gly Leu Met Ser Ser Ala Lys Leu His Phe Gly Glu Ala Leu Thr
                660                 665                 670

Ala Gly Arg Glu Ala Ala Gln Gly His Gln Gln Pro Val Gln Gln His
            675                 680                 685

Gln Gln Pro Thr His Thr Pro Gly Asn Pro Gly Ser Ser Gly Thr Ala
        690                 695                 700

Leu Ala Thr Lys Phe Gly Gly Ile Ile Gly Gly Ile His Met Ala
705                 710                 715                 720

Gln Glu Arg Leu Gly Ser Lys Lys Gln Pro Gly Gln Pro Gly Thr Arg
                725                 730                 735

Gly Ile Asp Asp Glu Pro Gly Gln Glu Gly Glu Leu Ser Arg Gly Phe
            740                 745                 750

Gly Asp Met Ser Leu Gly Gln Gln Ser Phe Gly Ser Gly Glu Ser Leu
        755                 760                 765

Thr Tyr His Glu Tyr Asp Ala Asn Ile Arg Phe Glu Arg Phe Asp Leu
        770                 775                 780

Gly Gly Arg Pro Phe Thr Val His Ile Phe Leu Gly Asp Phe Asn Pro
785                 790                 795                 800

Asp Pro Ala Thr Trp Met Trp Asp Lys Asn Arg Val Gly Gly Ile Tyr
                805                 810                 815

Asn Phe Val Ala Gly Val Gln Arg Gly Asp Gly Ser Ala Cys Ser Asn
            820                 825                 830

Cys Glu Thr Gln Ser Gln Asp His Thr Ile Val Thr Gly Gln Val Ser
        835                 840                 845

Leu Thr Asn Ala Leu Leu Asp Asp Val Glu Asp Ser Ala Asn Gly Leu
        850                 855                 860

Asn Ser Leu Ile Pro Glu Glu Val Ile Pro Tyr Leu Gln Arg His Leu
865                 870                 875                 880

His Trp Arg Ile Thr Asp Pro Asn Gly Arg Glu Ile Pro Arg Gln Ser
                885                 890                 895

Leu Asn Thr Leu Lys Ile Ser Val Val Glu Cys Ser Ala Thr Ile Ser
                900                 905                 910
```

-continued

```
Asn Asn Pro Gly Glu Leu Thr Gln Tyr Gly Asp His Arg Val Leu Asp
            915                 920                 925

Ile Val Thr Glu Gly Arg Pro Ala Gly Lys Ala Ala Gly Asp Gly Tyr
    930                 935                 940

<210> SEQ ID NO 5
<211> LENGTH: 440
<212> TYPE: PRT
<213> ORGANISM: Arthrobotrys oligospora

<400> SEQUENCE: 5

Met Ala Ser Ala Pro Tyr Ala Ile Thr Gly Ile Pro Thr Thr Arg Ala
 1               5                  10                  15

Pro Asp Gly Ala Leu Pro Leu Arg Gln Glu Ile Asp Ala Trp Ser Ala
            20                  25                  30

Asn Pro Ala Asn Val Asp Gln Val Asn Leu Tyr Leu Gln Ala Leu Ala
        35                  40                  45

Ala Phe Gln Gln Leu Pro Ala Thr Asp Lys Leu Ser Tyr Phe Gln Ile
    50                  55                  60

Ala Gly Ile His Gly Glu Pro Phe Ile Pro Trp Asp Glu Asn Thr Ser
65                  70                  75                  80

Pro Asn Pro Arg Ser Arg Trp Arg Gly Tyr Cys Thr His Ala Ser Ile
                85                  90                  95

Leu Phe Pro Thr Trp His Arg Pro Tyr Leu Ala Val Phe Glu Gln Ile
            100                 105                 110

Leu His Ser Ile Met Gln Arg Ile Ala Ala Ala Tyr Pro Asp Gln Glu
        115                 120                 125

Leu Arg Thr Arg Tyr Gln Thr Ala Ala Glu Ala Phe Arg Ile Pro Tyr
    130                 135                 140

Trp Asp Ser Ala Gln Leu Lys Glu Arg Gly Gly Arg Arg Ser Leu Asn
145                 150                 155                 160

Val Pro Tyr Leu Cys Thr Leu Pro Thr Val Gln Val Phe Thr Pro Thr
                165                 170                 175

Ser Ala Gly Asp Thr Ile Arg Pro Phe Glu Thr Ile Asp Asn Pro Leu
            180                 185                 190

Tyr Ser Tyr Lys Phe Val Thr Thr Gln Gly Ile Thr Ser Phe Gln Asp
        195                 200                 205

Gln Asp Gly Asn Phe Phe Pro Phe Ala Asn Ala Met Gly Thr Ser Arg
    210                 215                 220

Tyr Pro Pro Gln Tyr Asn Ser Arg Asp Pro Thr Val Ser Ser Gln Trp
225                 230                 235                 240

Thr Asn Gly Phe Val Asp Asn Asp Ser Ile Thr Glu Ala Leu Arg Asn
                245                 250                 255

Leu Ser Ser Leu Gly Glu Asp Val Tyr Arg Ser Phe Thr Thr Ser Asn
            260                 265                 270

Tyr Ala Trp Tyr Ser Ser Thr Gln Gln Ser Asn Pro Ala Pro Asn
        275                 280                 285

Ser Tyr Gln Ser Leu Glu Ser Ile His Asn Glu Ile His Gly Ile Thr
    290                 295                 300

Gly Gly Gly Gly His Met Ser Trp Asn Thr Val Ser Ser Phe Asp Pro
305                 310                 315                 320

Ile Phe Trp Leu His His Cys Asn Val Asp Arg Leu Phe Ala Ile Trp
                325                 330                 335

Gln Ala Ile Tyr Ala Asp Thr Gly Arg Tyr Pro Asp Ala Trp Phe Asn
            340                 345                 350
```

```
Ala Gln Ser Ala Gln Leu Arg Asp Glu Arg Gly Thr Trp Ser Ile Ala
        355                 360                 365

Ala Gly Ser Arg Glu Asn Ala Asp Thr Pro Leu Ala Pro Phe His Lys
    370                 375                 380

Asp Asp Arg Gly Ser Val Tyr Asn Ser Asn Asp Val Arg Asn Trp Thr
385                 390                 395                 400

Arg Phe Gly Ser Ser Tyr Pro Glu Leu Gln Pro Trp Leu Pro Gln Tyr
                405                 410                 415

Arg Asp Ser Thr Gly Glu Phe Asn Ala Thr Leu Tyr Arg Asn Asp Val
            420                 425                 430

Val Ala Gln Val Thr Asp Leu Tyr
        435                 440

<210> SEQ ID NO 6
<211> LENGTH: 2835
<212> TYPE: DNA
<213> ORGANISM: Artificial Sequence
<220> FEATURE:
<223> OTHER INFORMATION: Synthetic sequence encoding AXN-1

<400> SEQUENCE: 6
```

| | | | | | |
|---|---|---|---|---|---|
| atggcttctg | ctccatatgc | tattaccggt | attccaacta | ctagggctcc | agatggtgct | 60 |
| ttgccactta | ggcaagagat | tgatgcttgg | agtgctaacc | cagctaacgt | tgatcaggtg | 120 |
| aacctttacc | ttcaagctct | tgctgctttc | caacaacttc | cagctaccga | taagttgtcc | 180 |
| tacttccaga | ttgctggtat | tcatggcgaa | ccattcattc | catgggatga | aacacttcct | 240 |
| ccaaacccaa | gatctaggtg | gagaggatat | tgcacccacg | cttctatttt | gttcccaacc | 300 |
| tggcatagac | ataccttgc | tgtgttcgag | cagattctcc | actctatcat | gcaaagaatc | 360 |
| gctgctgctt | atccagatca | agagcttagg | actagatacc | aaactgctgc | tgaggctttc | 420 |
| aggattccat | attgggattc | cgctcagttg | aaagaaagag | gtggaagaag | atctctcaac | 480 |
| gttccatact | tgtgcactct | tccaactgtt | caagttttca | ccccaacttc | agctggtgat | 540 |
| accattagac | ccttcgagac | tattgataac | ccactctact | cctacaagtt | cgttactacc | 600 |
| cagggaatta | cctcattcca | agatcaggat | ggcaacttct | tcccattcgc | taacgctatg | 660 |
| ggaacttcaa | gatacccacc | acagtacaac | tcaagagatc | caaccgtttc | ttctcaatgg | 720 |
| accaacggat | tcgtggataa | cgattccatt | actgaggctc | ttaggaacct | ttctagcctt | 780 |
| ggagaggatg | tgtacagatc | tttcaccacc | tctaactacg | cttggtactc | ttctactcag | 840 |
| caatctaacc | cacctgctcc | aaaactcttac | cagtctctgg | agtctattca | aacgagatt | 900 |
| cacggaatta | ctggtggagg | tggacatatg | tcttggaaca | ccgtgtcatc | cttcgatcca | 960 |
| attttctggc | ttcatcactg | caacgttgat | aggcttttcg | ctatttggca | agctatctac | 1020 |
| gctgatactg | aagatatcc | agatgcatgg | ttcaacgctc | aatctgctca | acttagagat | 1080 |
| gagagggaa | cttggtctat | tgctgctgga | tcaagagaaa | acgctgatac | tccacttgct | 1140 |
| ccattccata | aggatgatag | gggttctgtg | tacaactcta | acgatgttag | gaactggact | 1200 |
| agattcggat | cttcttaccc | agaacttcaa | ccatggcttc | cacagtatag | ggattctacc | 1260 |
| ggtgagttca | acgctactct | ctacaggaac | gatgttgttg | ctcaggttac | cgatctttac | 1320 |
| tcaagagtga | gaagaagggt | tcaaaacact | caagttccta | ggaacagact | ttcgctgct | 1380 |
| actcaaactg | gaactcaaac | cttccaagga | tcttctgcta | ctgctggcgg | atctttcgct | 1440 |
| gctccaccaa | ctactcaagg | accaggacaa | caacttcaat | tcggaccacc | accatctggt | 1500 |
| ggacaacagg | ctttcgcacc | accacctact | gttcaagctc | aagctcaatc | tcagggacaa | 1560 |

-continued

```
ccattcactc cacctactac tttgccaact caaggacaac aattcacatc tccaccacca    1620
caaactgctc aaggtcaaca gttcccaccc ccacctactc aacaacaaca gttctctcca    1680
cctcctactc atcagcaaca attcgctcct ccacccacac aagaacatgg acaagctgtt    1740
acttctcctc ctgctcaaac tcaattttct ccacctccaa cacaggcttt ctcaccacct    1800
ccaactggtg attctcatgg acagcaattc actcctcaac cacaacagca gtttactcca    1860
cagccacaac aacagcagca acagcaattc gctccacctc aacaaggacc aggtggacat    1920
actccacaag acagcattc ttcaccacca cctaagaagt ctggactttc tggtcttatg    1980
tcctctgcta agttgcattt cggagaggct cttactgctg aagagaagc tgctcaagga    2040 catcaacaac cagttcaaca acatcaacag ccaactcata ctccaggaaa cccaggatct    2100
tctggaactg ctcttgctac taagttcgga ggaattattg gaggtggaat ccatatggct    2160
caagagagac tcggatctaa gaagcaacca ggacaaccag gtactagggg tattgatgat    2220
gaaccaggac aagagggtga actttcaaga ggattcggag atatgtctct tggtcaacag    2280
tctttcggat ctggtgagtc tcttacttac cacgagtacg atgctaacat tagattcgag    2340
agattcgatc ttggaggaag gccattcacc gttcacattt tcttgggaga cttcaaccca    2400
gatccagcta cttggatgtg ggataagaac agagttggag catctataa cttcgttgct    2460 ggtgttcaaa gggagatgg atctgcttgc tctaactgcg agactcagtc tcaagatcat    2520
accattgtga ccggacaagt ttctcttacc aacgctctcc ttgatgatgt tgaggattct    2580
gctaacggac ttaactctct cattcccgag gaagtgattc cataccttca gaggcatctc    2640
cattggagaa ttaccgatcc aaacggaaga gagattccaa ggcagtctct taacacccctt    2700 aagatttctg ttgtggagtg ctctgctacc atttctaaca accctggtga gttgactcaa    2760
tacggtgatc atagggtgtt ggatattgtg actgaaggta gaccagctgg aaaggctgct    2820
ggtgatggct actaa                                                    2835
```

```
<210> SEQ ID NO 7
<211> LENGTH: 1083
<212> TYPE: DNA
<213> ORGANISM: Bacillus thuringiensis
<220> FEATURE:
<221> NAME/KEY: CDS
<222> LOCATION: (1)...(1083)

<400> SEQUENCE: 7
```

```
atg aga att aga agg aac caa tcc act ctg agc cat aat gaa cgc cta      48
Met Arg Ile Arg Arg Asn Gln Ser Thr Leu Ser His Asn Glu Arg Leu
1               5                   10                  15 gcg ttt act aat gcg gta tta gaa tta aaa cgt aga cca agt cgt tta      96
Ala Phe Thr Asn Ala Val Leu Glu Leu Lys Arg Arg Pro Ser Arg Leu
            20                  25                  30 ccg atg tca ttg ggt agt aca agt cgt tat gat gat tat gtt tat tgg    144
Pro Met Ser Leu Gly Ser Thr Ser Arg Tyr Asp Asp Tyr Val Tyr Trp
        35                  40                  45 cat tta cag tca atg gaa aat caa aca tcg act aca cca gga tgg gct    192
His Leu Gln Ser Met Glu Asn Gln Thr Ser Thr Thr Pro Gly Trp Ala
    50                  55                  60 cat aga ggc cca gca ttt tta cct tgg cat cgt tat tat cta aat caa    240
His Arg Gly Pro Ala Phe Leu Pro Trp His Arg Tyr Tyr Leu Asn Gln
65                  70                  75                  80 ttt gaa gaa gat tta caa cga att gat cat aca gtt aca ctt cct tat    288
Phe Glu Glu Asp Leu Gln Arg Ile Asp His Thr Val Thr Leu Pro Tyr
                85                  90                  95
```

| | | | | | | | | | | | | | | | | |
|---|---|---|---|---|---|---|---|---|---|---|---|---|---|---|---|---|
| tgg | gat | tgg | aca | gtt | gat | aac | tca | act | gat | tca | tca | gtt | cca | gga | agt | 336 |
| Trp | Asp | Trp | Thr | Val | Asp | Asn | Ser | Thr | Asp | Ser | Ser | Val | Pro | Gly | Ser | |
| | | | 100 | | | | | 105 | | | | | 110 | | | |
| cct | tgg | act | gat | gat | ttt | atg | ggc | ggt | gat | ggt | gat | cct | acc | caa | gaa | 384 |
| Pro | Trp | Thr | Asp | Asp | Phe | Met | Gly | Gly | Asp | Gly | Asp | Pro | Thr | Gln | Glu | |
| | | 115 | | | | | 120 | | | | | 125 | | | | |
| tat | act | gtc | aca | aca | ggt | ccc | ttt | aca | ggt | gac | aat | tgg | aag | tta | act | 432 |
| Tyr | Thr | Val | Thr | Thr | Gly | Pro | Phe | Thr | Gly | Asp | Asn | Trp | Lys | Leu | Thr | |
| | 130 | | | | | 135 | | | | | 140 | | | | | |
| ctt | ttt | gat | cat | cat | gaa | aac | gag | cct | cat | aat | gct | cga | tta | cgc | cgt | 480 |
| Leu | Phe | Asp | His | His | Glu | Asn | Glu | Pro | His | Asn | Ala | Arg | Leu | Arg | Arg | |
| 145 | | | | | 150 | | | | | 155 | | | | | 160 | |
| cag | tta | gga | act | act | tta | aat | gcc | tct | gga | aat | act | ata | tca | atc | aat | 528 |
| Gln | Leu | Gly | Thr | Thr | Leu | Asn | Ala | Ser | Gly | Asn | Thr | Ile | Ser | Ile | Asn | |
| | | | 165 | | | | | 170 | | | | | 175 | | | |
| ctt | cca | aca | gat | tca | gag | gta | cag | aat | tgt | tta | tta | gaa | act | cca | tat | 576 |
| Leu | Pro | Thr | Asp | Ser | Glu | Val | Gln | Asn | Cys | Leu | Leu | Glu | Thr | Pro | Tyr | |
| | | 180 | | | | | 185 | | | | | 190 | | | | |
| tat | gta | tct | cct | tgg | cgt | gca | ggg | caa | gat | gta | aat | caa | cct | gca | tta | 624 |
| Tyr | Val | Ser | Pro | Trp | Arg | Ala | Gly | Gln | Asp | Val | Asn | Gln | Pro | Ala | Leu | |
| | 195 | | | | | 200 | | | | | 205 | | | | | |
| aat | cca | aca | aaa | cca | agt | ttt | tgt | aat | cgt | ctt | gaa | ggt | tgg | tat | gga | 672 |
| Asn | Pro | Thr | Lys | Pro | Ser | Phe | Cys | Asn | Arg | Leu | Glu | Gly | Trp | Tyr | Gly | |
| 210 | | | | | 215 | | | | | 220 | | | | | | |
| gca | gga | agt | att | cat | aat | aaa | gtt | cat | gta | tgg | gta | gct | ggt | gct | aca | 720 |
| Ala | Gly | Ser | Ile | His | Asn | Lys | Val | His | Val | Trp | Val | Ala | Gly | Ala | Thr | |
| 225 | | | | | 230 | | | | | 235 | | | | | 240 | |
| gag | ggc | tct | atg | att | tgg | atg | agc | tca | cca | aat | gat | cct | gtc | ttt | ttc | 768 |
| Glu | Gly | Ser | Met | Ile | Trp | Met | Ser | Ser | Pro | Asn | Asp | Pro | Val | Phe | Phe | |
| | | | | 245 | | | | | 250 | | | | | 255 | | |
| tta | cat | cat | gca | aat | att | gat | cgc | cta | tgg | gtc | caa | tgg | cag | gcc | aat | 816 |
| Leu | His | His | Ala | Asn | Ile | Asp | Arg | Leu | Trp | Val | Gln | Trp | Gln | Ala | Asn | |
| | | | 260 | | | | | 265 | | | | | 270 | | | |
| aat | cca | aat | gaa | ggg | tat | cat | cct | act | gga | aat | ggt | aat | gaa | gtt | gga | 864 |
| Asn | Pro | Asn | Glu | Gly | Tyr | His | Pro | Thr | Gly | Asn | Gly | Asn | Glu | Val | Gly | |
| | | 275 | | | | | 280 | | | | | 285 | | | | |
| cca | aca | ggt | cat | aat | tta | aat | gat | tca | atg | aat | cct | tgg | ggg | agg | aag | 912 |
| Pro | Thr | Gly | His | Asn | Leu | Asn | Asp | Ser | Met | Asn | Pro | Trp | Gly | Arg | Lys | |
| | 290 | | | | | 295 | | | | | 300 | | | | | |
| gtt | act | cca | aat | aat | gtc | ctt | aat | cat | tat | agt | ctt | ggt | tat | act | tac | 960 |
| Val | Thr | Pro | Asn | Asn | Val | Leu | Asn | His | Tyr | Ser | Leu | Gly | Tyr | Thr | Tyr | |
| 305 | | | | | 310 | | | | | 315 | | | | | 320 | |
| gat | aca | gat | tca | acc | cct | ctt | tct | gaa | atc | ttt | atg | cat | aca | ttt | aat | 1008 |
| Asp | Thr | Asp | Ser | Thr | Pro | Leu | Ser | Glu | Ile | Phe | Met | His | Thr | Phe | Asn | |
| | | | | 325 | | | | | 330 | | | | | 335 | | |
| ctg | aaa | att | cgt | aaa | gaa | aaa | caa | atc | aaa | gat | ggt | cat | ttt | ggt | tta | 1056 |
| Leu | Lys | Ile | Arg | Lys | Glu | Lys | Gln | Ile | Lys | Asp | Gly | His | Phe | Gly | Leu | |
| | | | 340 | | | | | 345 | | | | | 350 | | | |
| agt | caa | gaa | gat | tta | gac | aaa | ttg | taa | | | | | | | | 1083 |
| Ser | Gln | Glu | Asp | Leu | Asp | Lys | Leu | | | | | | | | | |
| | | | 355 | | | | | 360 | | | | | | | | |

<210> SEQ ID NO 8
<211> LENGTH: 360
<212> TYPE: PRT
<213> ORGANISM: Bacillus thuringiensis

<400> SEQUENCE: 8

Met Arg Ile Arg Arg Asn Gln Ser Thr Leu Ser His Asn Glu Arg Leu
1               5                   10                  15

Ala Phe Thr Asn Ala Val Leu Glu Leu Lys Arg Arg Pro Ser Arg Leu

```
                     20                  25                  30
Pro Met Ser Leu Gly Ser Thr Ser Arg Tyr Asp Asp Tyr Val Tyr Trp
            35                  40                  45
His Leu Gln Ser Met Glu Asn Gln Thr Ser Thr Thr Pro Gly Trp Ala
        50                  55                  60
His Arg Gly Pro Ala Phe Leu Pro Trp His Arg Tyr Tyr Leu Asn Gln
 65                  70                  75                  80
Phe Glu Glu Asp Leu Gln Arg Ile Asp His Thr Val Thr Leu Pro Tyr
                85                  90                  95
Trp Asp Trp Thr Val Asp Asn Ser Thr Asp Ser Ser Val Pro Gly Ser
            100                 105                 110
Pro Trp Thr Asp Asp Phe Met Gly Gly Asp Gly Asp Pro Thr Gln Glu
        115                 120                 125
Tyr Thr Val Thr Thr Gly Pro Phe Thr Gly Asp Asn Trp Lys Leu Thr
130                 135                 140
Leu Phe Asp His His Glu Asn Glu Pro His Asn Ala Arg Leu Arg Arg
145                 150                 155                 160
Gln Leu Gly Thr Thr Leu Asn Ala Ser Gly Asn Thr Ile Ser Ile Asn
                165                 170                 175
Leu Pro Thr Asp Ser Glu Val Gln Asn Cys Leu Leu Glu Thr Pro Tyr
            180                 185                 190
Tyr Val Ser Pro Trp Arg Ala Gly Gln Asp Val Asn Gln Pro Ala Leu
        195                 200                 205
Asn Pro Thr Lys Pro Ser Phe Cys Asn Arg Leu Glu Gly Trp Tyr Gly
    210                 215                 220
Ala Gly Ser Ile His Asn Lys Val His Val Trp Val Ala Gly Ala Thr
225                 230                 235                 240
Glu Gly Ser Met Ile Trp Met Ser Ser Pro Asn Asp Pro Val Phe Phe
                245                 250                 255
Leu His His Ala Asn Ile Asp Arg Leu Trp Val Gln Trp Gln Ala Asn
            260                 265                 270
Asn Pro Asn Glu Gly Tyr His Pro Thr Gly Asn Gly Asn Glu Val Gly
        275                 280                 285
Pro Thr Gly His Asn Leu Asn Asp Ser Met Asn Pro Trp Gly Arg Lys
    290                 295                 300
Val Thr Pro Asn Asn Val Leu Asn His Tyr Ser Leu Gly Tyr Thr Tyr
305                 310                 315                 320
Asp Thr Asp Ser Thr Pro Leu Ser Glu Ile Phe Met Thr His Phe Asn
                325                 330                 335
Leu Lys Ile Arg Lys Glu Lys Gln Ile Lys Asp Gly His Phe Gly Leu
            340                 345                 350
Ser Gln Glu Asp Leu Asp Lys Leu
        355                 360

<210> SEQ ID NO 9
<211> LENGTH: 369
<212> TYPE: PRT
<213> ORGANISM: Artificial Sequence
<220> FEATURE:
<223> OTHER INFORMATION: AXN-2 with His tag

<400> SEQUENCE: 9

Met Ala His His His His His His Gly Ser Met Arg Ile Arg Arg Asn
 1               5                   10                  15
Gln Ser Thr Leu Ser His Asn Glu Arg Leu Ala Phe Thr Asn Ala Val
                20                  25                  30
```

Leu Glu Leu Lys Arg Arg Pro Ser Arg Leu Pro Met Ser Leu Gly Ser
        35                  40                  45

Thr Ser Arg Tyr Asp Asp Tyr Val Tyr Trp His Leu Gln Ser Met Glu
 50                  55                  60

Asn Gln Thr Ser Thr Pro Gly Trp Ala His Arg Gly Pro Ala Phe
 65                  70                  75                  80

Leu Pro Trp His Arg Tyr Tyr Leu Asn Gln Phe Glu Glu Asp Leu Gln
                 85                  90                  95

Arg Ile Asp His Thr Val Thr Leu Pro Tyr Trp Asp Trp Thr Val Asp
                100                 105                 110

Asn Ser Thr Asp Ser Ser Val Pro Gly Ser Pro Trp Thr Asp Asp Phe
            115                 120                 125

Met Gly Gly Asp Gly Asp Pro Thr Gln Glu Tyr Thr Val Thr Thr Gly
       130                 135                 140

Pro Phe Thr Gly Asp Asn Trp Lys Leu Thr Leu Phe Asp His His Glu
145                 150                 155                 160

Asn Glu Pro His Asn Ala Arg Leu Arg Arg Gln Leu Gly Thr Thr Leu
                165                 170                 175

Asn Ala Ser Gly Asn Thr Ile Ser Ile Asn Leu Pro Thr Asp Ser Glu
            180                 185                 190

Val Gln Asn Cys Leu Leu Glu Thr Pro Tyr Tyr Val Ser Pro Trp Arg
        195                 200                 205

Ala Gly Gln Asp Val Asn Gln Pro Ala Leu Asn Pro Thr Lys Pro Ser
    210                 215                 220

Phe Cys Asn Arg Leu Glu Gly Trp Tyr Gly Ala Gly Ser Ile His Asn
225                 230                 235                 240

Lys Val His Val Trp Val Ala Gly Ala Thr Glu Gly Ser Met Ile Trp
                245                 250                 255

Met Ser Ser Pro Asn Asp Pro Val Phe Phe Leu His His Ala Asn Ile
            260                 265                 270

Asp Arg Leu Trp Val Gln Trp Gln Ala Asn Asn Pro Asn Glu Gly Tyr
        275                 280                 285

His Pro Thr Gly Asn Gly Asn Glu Val Gly Pro Thr Gly His Asn Leu
    290                 295                 300

Asn Asp Ser Met Asn Pro Trp Gly Arg Lys Val Thr Pro Asn Asn Val
305                 310                 315                 320

Leu Asn His Tyr Ser Leu Gly Tyr Thr Tyr Asp Thr Asp Ser Thr Pro
                325                 330                 335

Leu Ser Glu Ile Phe Met His Thr Phe Asn Leu Lys Ile Arg Lys Glu
            340                 345                 350

Lys Gln Ile Lys Asp Gly His Phe Gly Leu Ser Gln Glu Asp Leu Asp
        355                 360                 365

Lys

<210> SEQ ID NO 10
<211> LENGTH: 1083
<212> TYPE: DNA
<213> ORGANISM: Artificial Sequence
<220> FEATURE:
<223> OTHER INFORMATION: Synthetic sequence encoding AXN-2

<400> SEQUENCE: 10
atgaggatca gaagaaacca gtctaccttg tctcataacg agaggcttgc tttcactaac        60
gctgtgcttg agcttaagag aaggccatct aggcttccaa tgtctcttgg atctacctcc       120

-continued

```
agatacgatg attacgtgta ctggcacctt caatctatgg aaaaccagac ttctactact    180
ccaggatggg ctcatagagg accagctttt ttgccatggc acaggtatta tctcaaccag    240
ttcgaagagg atcttcagag gattgatcat accgttaccc ttccatattg ggattggacc    300
gtggataact ctaccgattc ttctgttcca ggatctccat ggactgatga tttcatggga    360
ggtgatggtg atccaactca agagtacact gttactactg gaccattcac tggtgataac    420
tggaagctca ccctttttcga tcatcatgag aacgaaccac ataacgctag acttagaagg    480
caacttggaa ctacccttaa cgcttccgga aacaccattt ccattaaccct tccaaccgat    540
tctgaggttc agaactgcct tcttgagact ccttactacg tttcaccttg gagagctgga    600
caagatgtta accagccagc tcttaaccca actaagccat ctttctgcaa cagacttgag    660
ggatggtatg gtgctggatc tattcataac aaagtgcatg tttgggtggc aggtgctact    720
gaaggatcta tgatctggat gtcctctcca aacgatccag ttttcttcct tcaccacgct    780
aacattgata ggctttgggt tcaatggcaa gctaacaacc caaacgaggg atatcatcca    840
actgaaaacg gaaacgaagt tggaccaacc ggacataacc ttaacgattc catgaaccca    900
tggggaagaa aggttacccc aaacaacgtt cttaaccact actctctcgg atacacttac    960
gatactgatt ctaccccact ctccgagatt ttcatgcaca ccttcaacct caagatcagg   1020
aaagagaagc agattaagga cggacatttc ggactttctc aagaggatct cgacaagctc   1080
tga                                                                 1083
```

<210> SEQ ID NO 11
<211> LENGTH: 4795
<212> TYPE: DNA
<213> ORGANISM: Pseudomonas
<220> FEATURE:
<221> NAME/KEY: misc_difference
<222> LOCATION: (1635)...(1865)
<223> OTHER INFORMATION: putative transcription regulator
<220> FEATURE:
<221> NAME/KEY: CDS
<222> LOCATION: (1967)...(3430)
<223> OTHER INFORMATION: ORF for axn-8
<220> FEATURE:
<221> NAME/KEY: CDS
<222> LOCATION: (3443)...(4219)
<223> OTHER INFORMATION: ORF for metal binding integral membrane protein

<400> SEQUENCE: 11

```
ggtgctgtct gccggggtga ggccgaactc tacaaaaccg aactgctgca ggtgctggcg     60
gacaagtccg ggctgccccc cgatcaagcc caggaatatc tgcacaacgc aggctatgac    120
ctgaaccgcg ccttgagtgc tctggaacaa gcgcgcttca ccctgacccg gcgcatcctg    180
cgcaaacatc accaggacaa ggcccgggcc ctggacctga tcgcccagtc catcgaaacc    240
gccgaacaat tgccacgcca gtactggctg gccttcgagc ggctggagca actggccccg    300
gcaccgcgct gcttgatggt gctccacgaa tggctggcct tcgaggactg ggaaggcttc    360
gacagtgccc tgcactttca tctgccgcag gccatcgccc agttcaggca cctgcaactg    420
gatgccctgg cggacaccct ggaacaggcc gatcagcgcc agcgacagct acgggcagcc    480
catgccgagc gcgaaagccc catcgagctg gccgtgcagg tcaatcagga tccgttgttc    540
aacgcctgcc gggacagttt cagccaacag cggcttcggc tcgacgagcg cctgtacgaa    600
tgggtggagc gccatataga gcagtttcca gcctgagtgg cgagttcgcg tacgcgcaca    660
aaccgctgct acccacccccc ccgaaactcg ctaaactgcc gccctcaccg aacacggacc    720
tcggatcaag ccctcatgga attgcactac agcatcaccc ccgcccatat ccaggcctgg    780
```

```
atcgccgaac cgctgaagca ggaaatgctc aagcatgatc agcagcaggc ccaggcgatg    840
gccaatgttg cccggtggca acgccgcttg gtcggcccct tgatgttcgc cttgtgcctg    900
gtcggcggca tgctggcgct ctatttcccc gagcgacgct tcaccgcgca gaacgtcatt    960
gccatggtgc tgttcgcgtt gatcttcatc ccgctctggt ggcgtttttc cgggcgctgg   1020
atcaagcacc tgcaagcgcg tattgccgcc aaccacgcca agccccgggc gccgttgcgc   1080
gggctgaatc agcggctgat cgaaaccagg ctgcgggcgc cgctgaaatc cgtcgaaagc   1140
acctattgcc tgagcttcga cgaccagggc tttaccctcg acaaagcccg cagcggcaag   1200
agcaccctcg cctgggaaca gatcgcgcgc ctgcaggaaa caccggactt ctacctcgtg   1260
gcgagcgcgg acatggtgcg ccagggcgtg gcctgtctca ttgccaaaca cagtgacctg   1320
atgccggccg aggaatatca gcaagggctg caagcgtttc tgagccagtg cccagtggcg   1380
ccctcagcaa actgatcaca gtgctagcac tgcagaccga tacgcttcga gcactaccgc   1440
tcagcacctg cccgcaaaaa caccttgcag gtaaaacaac gccgactatg ctgccaaaat   1500
cagccctaat ggccattggc cttgagcggg ccgacctccg gttttgtcgt ccgggcatcg   1560
caacgctgat tagcagaaag ctatacacct gacgacgcaa gcgcgttcgc cgcggtgttt   1620
cccaggaggg aatcatgcct gccgcaggac agtacttgat tgcaatcccg gtctacgacg   1680
gtgtcgacct gctcgacgtc agcgcccct acgaactgtt cagtacaacc cctgcccccc    1740
ccttcttcag tggcgatcct tccgtcgcca aaccgccggt ctacacccca ggcgccggaa   1800
gcacctgcaa ttgcgctctc gccgagagca tcaccaatgt gctcaagcgc acaggccctt   1860
cctgagaggc ctgcaggcag gtgcacacag agtagcgctg tcgccgcgaa atgaagtccg   1920
gcctcacccc ggcagacagc acccaacagg aacggaggga atctcatga gtacttctcg   1980 tcaggatgtc gcaaaactcg gcccagggtg gaacaaggta ttactgaact acgcactggc   2040
catgcaagcg ttggatgaac agccaatagc ggaccgcaat agctggaaat tcctcggggc   2100
catgcatggg tttcatcccc aattatggat caacgagcgc ctgatcaagt caggtgcccc   2160
gattccagcg gatttgacca accataccta cggcaatcag tgtcagcacg gcagttggta   2220
ttttctgtcc tggcaccgtg cgtatctgtt tgcgttcgag gcaatcgtcg ccgctaaagt   2280
gaaggagctg acgggtgacg actgggcact tccctactgg aactacctcg acagcagcaa   2340
cccgcaagcg ctgtacctgc ccgatgcctt tgtcgccaag acattacccg acggaaagcc   2400
aaaccctctg aacaagtacc ctcgccgccc cggaatcaag gcgatcaagc cggtgcgcgg   2460
gttcagcctt gaggcgatgg atgagaatga cttcatcgta ggtaacggga ccctgggatt   2520
tggtgggggg attaccggca atttcgtcca gttcgacggg gttgccggcg agctggagac   2580
caacccgcat aacacggtcc atggcctcgt cggaggatac atgggcaatg ccttgctcgc   2640
aggtcttgat ccgatcttct ggcttcacca ttgcaacatc gatcggctct gggaggcgtg   2700
gatgaacacg ccgggcaaga caatggttcg cgatccgctc tggctcaatg cccggcagga   2760
ccgcagtttc atcatgccag taccccgaga caatgcacct ggagtaacgt tcaccagtaa   2820
ggacacgttg aaaggcggca aatttatcg gacctatgat gatttgatca tcggcacggg   2880
tgtaacgccg ggagtgcatg ctgtggcacg cgtcaatatg ggctcgccca gtaaacaaac   2940
cgttcagcca atcggcgcca atgccgcggt cgtcaagatc ggcggggcgc cggtaggtac   3000
ccatattgac ctcgaaccga cagccgccgc caacagcatg ccacgatgg gcgcgacatc   3060 gccaggcaag gaagtggccc ggctctatct ttccctggag tctgtgcgcg gctccgcacc   3120
ctcgcctctg ctggatgtgt acgtcaactt gcccgaaggc gccgaccgg cacttagccc    3180
```

```
tgaccggtac gccggtagcc ttacgctttt cggtctcaac gttgcctcgc aaacggacgg    3240
cccccatgca ggcagcgggt tgggctatac gatcgcacatc accgatctgg cccagcggct    3300
ggcggacgcc ggggactttg atccgaatca tctgcgggtg accctggtgc ctggagagca    3360
gataaccgat gaagaaccta taaccgttga acgcataagc gtactcaagc gaagcggcat    3420
cgtcagttga gggggcggcc tcatgcggcc aggcctggtt ttacgcagtt tcacttatgc    3480
cccttggcca gtgcttctgg ccacggcggg attcggcctg gcccttttcca tttacagcga    3540 cgcaagtaca gaaggtcccg cgttttgcgt ggccaccaat gggctatcga tcttcaccag    3600
ctggcccgcg gtgctgcaag cggagctcgc ggtgaacccg atccaccgta tcctggcggg    3660
ttggttgttg atgctgttga ccatgatgcc gccccttctg gcgatgccac tcatgcatgt    3720
gtggcgctcc agcctgccaa acaggcgaat acgtgcgagc gccggtttcc tgctcggcta    3780
ctgcgcgccg tggatggccg caggtctggt cctgtcggcc ctggcgctgt tgctacagat    3840
cactgtcgtg gacaacgccc tggcaatagc cctgctgatc gcgttgcttt ggagcgcaag    3900
cccgtggcac cgtgcggcac tcaatcgcag ccatcaaccg cggcgaatag gcctgttcgg    3960
tcgggccgcc gaccgggatt gcctggtctt cggcatgacg catggggcct attgtattgg    4020
ctcgtgctgg gcctggatgt tggtgcccgt tgtcagcggc gcctggcaca ttccgatgat    4080
gctgttcact ggcgtcatca tgctggctga acggttcacg cctcctggcc ctgcgcgctg    4140
gtgctggccc cggttttttt cacccgctca cctatacacc ctcctcaccc agcgcaatgc    4200
ggagcgtccc catggttagg cgtgtttgtc tggcaatcgg cgtcagcacg gtgacgcctg    4260
tcgcgaaact ggccctggac ttcgcctatc tggatggcgc cgttttcgcc gctcgcgcaa    4320
tgggagaatg ggccctgcgc tcgggtttcg gcgtcgacaa cgtaagagtc gtcgacgacg    4380
gctcaaccga cggcaaagcg aacccggtca cacgagagcg ggtacagcgg gccgtcgatg    4440
aactgttccc ggtgggcgcc gaggtcgttg accagttgat cctgtcattt tgcgggcatg    4500
gactgaccgg ggcgaacttc ggctcgatct ttttggctgtt cagcgactcg ctgcacatga    4560
agtaccgcat cgtggtcgat gggttctatg aggaattact tctgcacggc gtcaaacgca    4620
taacgcttat taccgacacc tgccgcgaag cgccgcagag cctggagctg atgcggcttg    4680
atggtgtgcg cgggatcgtt gtacagggca ctcgcgttga cagcccgaga ttcgaccgcc    4740
ttgcatcctg ccaggacgga cagctcggct atatggtcta tgaccctgcc gccgc         4795
```

```
<210> SEQ ID NO 12
<211> LENGTH: 1464
<212> TYPE: DNA
<213> ORGANISM: Pseudomonas
<220> FEATURE:
<221> NAME/KEY: CDS
<222> LOCATION: (1)...(1464)

<400> SEQUENCE: 12 atg agt act tct cgt cag gat gtc gca aaa ctc ggc cca ggg tgg aac      48
Met Ser Thr Ser Arg Gln Asp Val Ala Lys Leu Gly Pro Gly Trp Asn
1               5                   10                  15 aag gta tta ctg aac tac gcc ctc gcc atg caa gcg ttg gat gaa cag      96
Lys Val Leu Leu Asn Tyr Ala Leu Ala Met Gln Ala Leu Asp Glu Gln
            20                  25                  30 cca ata gcg gac cgc aat agc tgg aaa ttc ctc ggg gcc atg cat ggg     144
Pro Ile Ala Asp Arg Asn Ser Trp Lys Phe Leu Gly Ala Met His Gly
        35                  40                  45 ttt cat ccc caa tta tgg atc aac gag cgc ctg atc aag tca ggt gcc     192
Phe His Pro Gln Leu Trp Ile Asn Glu Arg Leu Ile Lys Ser Gly Ala
    50                  55                  60
```

```
ccg att cca gcg gat ttg acc aac cat acc tac ggc aat cag tgt cag         240
Pro Ile Pro Ala Asp Leu Thr Asn His Thr Tyr Gly Asn Gln Cys Gln
65                  70                  75                  80 cac ggc agt tgg tat ttt ctg tcc tgg cac cgt gcg tat ctg ttt gcg         288
His Gly Ser Trp Tyr Phe Leu Ser Trp His Arg Ala Tyr Leu Phe Ala
                85                  90                  95 ttc gag gca atc gtc gcc gct aaa gtg aag gag ctg acg ggt gac gac         336
Phe Glu Ala Ile Val Ala Ala Lys Val Lys Glu Leu Thr Gly Asp Asp
            100                 105                 110 tgg gca ctt ccc tac tgg aac tac ctc gac agc agc aac ccg caa gcg         384
Trp Ala Leu Pro Tyr Trp Asn Tyr Leu Asp Ser Ser Asn Pro Gln Ala
        115                 120                 125 ctg tac ctg ccc gat gcc ttt gtc gcc aag aca tta ccc gac gga aag         432
Leu Tyr Leu Pro Asp Ala Phe Val Ala Lys Thr Leu Pro Asp Gly Lys
    130                 135                 140 cca aac cct ctg aac aag tac cct cgc cgc ccc gga atc aag gcg atc         480
Pro Asn Pro Leu Asn Lys Tyr Pro Arg Arg Pro Gly Ile Lys Ala Ile
145                 150                 155                 160 aag ccg gtg cgc ggg ttc agc ctt gag gcg atg gat gag aat gac ttc         528
Lys Pro Val Arg Gly Phe Ser Leu Glu Ala Met Asp Glu Asn Asp Phe
                165                 170                 175 atc gta ggt aac ggg acc ctg gga ttt ggt ggg ggg att acc ggc aat         576
Ile Val Gly Asn Gly Thr Leu Gly Phe Gly Gly Gly Ile Thr Gly Asn
            180                 185                 190 ttc gtc cag ttc gac ggg gtt gcc ggc gag ctg gag acc aac ccg cat         624
Phe Val Gln Phe Asp Gly Val Ala Gly Glu Leu Glu Thr Asn Pro His
        195                 200                 205 aac acg gtc cat ggc ctc gtc gga gga tac atg ggc aat gcc ttg ctc         672
Asn Thr Val His Gly Leu Val Gly Gly Tyr Met Gly Asn Ala Leu Leu
    210                 215                 220 gca ggt ctt gat ccg atc ttc tgg ctt cac cat tgc aac atc gat cgg         720
Ala Gly Leu Asp Pro Ile Phe Trp Leu His His Cys Asn Ile Asp Arg
225                 230                 235                 240 ctc tgg gag gcg tgg atg aac acg ccg ggc aag aca atg gtt cgc gat         768
Leu Trp Glu Ala Trp Met Asn Thr Pro Gly Lys Thr Met Val Arg Asp
                245                 250                 255 ccg ctc tgg ctc aat ggc ccg gca gac cgc agt ttc atc atg cca gta         816
Pro Leu Trp Leu Asn Gly Pro Ala Asp Arg Ser Phe Ile Met Pro Val
            260                 265                 270 ccc gga gac aat gca cct gga gta acg ttc acc agt aag gac acg ttg         864
Pro Gly Asp Asn Ala Pro Gly Val Thr Phe Thr Ser Lys Asp Thr Leu
        275                 280                 285 aaa ggc ggc aaa ttt tat cgg acc tat gat gat ttg atc atc ggc acg         912
Lys Gly Gly Lys Phe Tyr Arg Thr Tyr Asp Asp Leu Ile Ile Gly Thr
    290                 295                 300 ggt gta acg ccg gga gtg cat gct gtg gca cgc gtc aat atg ggc tcg         960
Gly Val Thr Pro Gly Val His Ala Val Ala Arg Val Asn Met Gly Ser
305                 310                 315                 320 ccc agt aaa caa acc gtt cag cca atc ggc gcc aat gcc gcg gtc gtc        1008
Pro Ser Lys Gln Thr Val Gln Pro Ile Gly Ala Asn Ala Ala Val Val
                325                 330                 335 aag atc ggc ggg gcg ccg gta ggt acc cat att gac ctc gaa ccg aca        1056
Lys Ile Gly Gly Ala Pro Val Gly Thr His Ile Asp Leu Glu Pro Thr
            340                 345                 350 gcc gcc gcc aac agc atg gcc acg atg ggc gcg aca tcg cca ggc aag        1104
Ala Ala Ala Asn Ser Met Ala Thr Met Gly Ala Thr Ser Pro Gly Lys
        355                 360                 365 gaa gtg gcc cgg ctc tat ctt tcc ctg gag tct gtg cgc ggc tcc gca        1152
Glu Val Ala Arg Leu Tyr Leu Ser Leu Glu Ser Val Arg Gly Ser Ala
    370                 375                 380
```

```
ccc tcg cct ctg ctg gat gtg tac gtc aac ttg ccc gaa ggc gcc gac    1200
Pro Ser Pro Leu Leu Asp Val Tyr Val Asn Leu Pro Glu Gly Ala Asp
385                 390                 395                 400 ccg gca ctt agc cct gac cgg tac gcc ggt agc ctt acg ctt ttc ggt    1248
Pro Ala Leu Ser Pro Asp Arg Tyr Ala Gly Ser Leu Thr Leu Phe Gly
            405                 410                 415 ctc aac gtt gcc tcg caa acg gac ggc ccc cat gca ggc agc ggg ttg    1296
Leu Asn Val Ala Ser Gln Thr Asp Gly Pro His Ala Gly Ser Gly Leu
            420                 425                 430 ggc tat acg atc gac atc acc gat ctg gcc cag cgg ctg gcg gac gcc    1344
Gly Tyr Thr Ile Asp Ile Thr Asp Leu Ala Gln Arg Leu Ala Asp Ala
            435                 440                 445 ggg gac ttt gat ccg aat cat ctg cgg gtg acc ctg gtg cct gga gag    1392
Gly Asp Phe Asp Pro Asn His Leu Arg Val Thr Leu Val Pro Gly Glu
450                 455                 460 cag ata acc gat gaa gaa cct ata acc gtt gaa cgc ata agc gta ctc    1440
Gln Ile Thr Asp Glu Glu Pro Ile Thr Val Glu Arg Ile Ser Val Leu
465                 470                 475                 480 aag cga agc ggc atc gtc agt tga                                    1464
Lys Arg Ser Gly Ile Val Ser
                485
```

<210> SEQ ID NO 13
<211> LENGTH: 487
<212> TYPE: PRT
<213> ORGANISM: Pseudomonas

<400> SEQUENCE: 13

```
Met Ser Thr Ser Arg Gln Asp Val Ala Lys Leu Gly Pro Gly Trp Asn
  1               5                  10                  15

Lys Val Leu Leu Asn Tyr Ala Leu Ala Met Gln Ala Leu Asp Glu Gln
                 20                  25                  30

Pro Ile Ala Asp Arg Asn Ser Trp Lys Phe Leu Gly Ala Met His Gly
             35                  40                  45

Phe His Pro Gln Leu Trp Ile Asn Glu Arg Leu Ile Lys Ser Gly Ala
 50                  55                  60

Pro Ile Pro Ala Asp Leu Thr Asn His Thr Tyr Gly Asn Gln Cys Gln
 65                  70                  75                  80

His Gly Ser Trp Tyr Phe Leu Ser Trp His Arg Ala Tyr Leu Phe Ala
                 85                  90                  95

Phe Glu Ala Ile Val Ala Ala Lys Val Lys Glu Leu Thr Gly Asp Asp
                100                 105                 110

Trp Ala Leu Pro Tyr Trp Asn Tyr Leu Asp Ser Ser Asn Pro Gln Ala
            115                 120                 125

Leu Tyr Leu Pro Asp Ala Phe Val Ala Lys Thr Leu Pro Asp Gly Lys
130                 135                 140

Pro Asn Pro Leu Asn Lys Tyr Pro Arg Arg Pro Gly Ile Lys Ala Ile
145                 150                 155                 160

Lys Pro Val Arg Gly Phe Ser Leu Glu Ala Met Asp Glu Asn Asp Phe
                165                 170                 175

Ile Val Gly Asn Gly Thr Leu Gly Phe Gly Gly Ile Thr Gly Asn
            180                 185                 190

Phe Val Gln Phe Asp Gly Val Ala Gly Glu Leu Glu Thr Asn Pro His
            195                 200                 205

Asn Thr Val His Gly Leu Val Gly Gly Tyr Met Gly Asn Ala Leu Leu
210                 215                 220

Ala Gly Leu Asp Pro Ile Phe Trp Leu His His Cys Asn Ile Asp Arg
```

```
                225                 230                 235                 240
Leu Trp Glu Ala Trp Met Asn Thr Pro Gly Lys Thr Met Val Arg Asp
                245                 250                 255

Pro Leu Trp Leu Asn Gly Pro Ala Asp Arg Ser Phe Ile Met Pro Val
            260                 265                 270

Pro Gly Asp Asn Ala Pro Gly Val Thr Phe Thr Ser Lys Asp Thr Leu
        275                 280                 285

Lys Gly Gly Lys Phe Tyr Arg Thr Tyr Asp Asp Leu Ile Ile Gly Thr
    290                 295                 300

Gly Val Thr Pro Gly Val His Ala Val Ala Arg Val Asn Met Gly Ser
305                 310                 315                 320

Pro Ser Lys Gln Thr Val Gln Pro Ile Gly Ala Asn Ala Ala Val Val
                325                 330                 335

Lys Ile Gly Gly Ala Pro Val Gly Thr His Ile Asp Leu Glu Pro Thr
            340                 345                 350

Ala Ala Ala Asn Ser Met Ala Thr Met Gly Ala Thr Ser Pro Gly Lys
        355                 360                 365

Glu Val Ala Arg Leu Tyr Leu Ser Leu Glu Ser Val Arg Gly Ser Ala
    370                 375                 380

Pro Ser Pro Leu Leu Asp Val Tyr Val Asn Leu Pro Glu Gly Ala Asp
385                 390                 395                 400

Pro Ala Leu Ser Pro Asp Arg Tyr Ala Gly Ser Leu Thr Leu Phe Gly
                405                 410                 415

Leu Asn Val Ala Ser Gln Thr Asp Gly Pro His Ala Gly Ser Gly Leu
            420                 425                 430

Gly Tyr Thr Ile Asp Ile Thr Asp Leu Ala Gln Arg Leu Ala Asp Ala
        435                 440                 445

Gly Asp Phe Asp Pro Asn His Leu Arg Val Thr Leu Val Pro Gly Glu
    450                 455                 460

Gln Ile Thr Asp Glu Pro Ile Thr Val Glu Arg Ile Ser Val Leu
465                 470                 475                 480

Lys Arg Ser Gly Ile Val Ser
            485

<210> SEQ ID NO 14
<211> LENGTH: 295
<212> TYPE: PRT
<213> ORGANISM: Artificial Sequence
<220> FEATURE:
<223> OTHER INFORMATION: Predicted processed AXN-8 protein

<400> SEQUENCE: 14

Met Ser Thr Ser Arg Gln Asp Val Ala Lys Leu Gly Pro Gly Trp Asn
1               5                   10                  15

Lys Val Leu Leu Asn Tyr Ala Leu Ala Met Gln Ala Leu Asp Glu Gln
            20                  25                  30

Pro Ile Ala Asp Arg Asn Ser Trp Lys Phe Leu Gly Ala Met His Gly
        35                  40                  45

Phe His Pro Gln Leu Trp Ile Asn Glu Arg Leu Ile Lys Ser Gly Ala
    50                  55                  60

Pro Ile Pro Ala Asp Leu Thr Asn His Thr Tyr Gly Asn Gln Cys Gln
65                  70                  75                  80

His Gly Ser Trp Tyr Phe Leu Ser Trp His Arg Ala Tyr Leu Phe Ala
                85                  90                  95

Phe Glu Ala Ile Val Ala Ala Lys Val Lys Glu Leu Thr Gly Asp Asp
            100                 105                 110
```

```
Trp Ala Leu Pro Tyr Trp Asn Tyr Leu Asp Ser Ser Asn Pro Gln Ala
        115                 120                 125

Leu Tyr Leu Pro Asp Ala Phe Val Ala Lys Thr Leu Pro Asp Gly Lys
    130                 135                 140

Pro Asn Pro Leu Asn Lys Tyr Pro Arg Arg Pro Gly Ile Lys Ala Ile
145                 150                 155                 160

Lys Pro Val Arg Gly Phe Ser Leu Glu Ala Met Asp Glu Asn Asp Phe
                165                 170                 175

Ile Val Gly Asn Gly Thr Leu Gly Phe Gly Gly Ile Thr Gly Asn
            180                 185                 190

Phe Val Gln Phe Asp Gly Val Ala Gly Glu Leu Glu Thr Asn Pro His
    195                 200                 205

Asn Thr Val His Gly Leu Val Gly Gly Tyr Met Gly Asn Ala Leu Leu
    210                 215                 220

Ala Gly Leu Asp Pro Ile Phe Trp Leu His His Cys Asn Ile Asp Arg
225                 230                 235                 240

Leu Trp Glu Ala Trp Met Asn Thr Pro Gly Lys Thr Met Val Arg Asp
                245                 250                 255

Pro Leu Trp Leu Asn Gly Pro Ala Asp Arg Ser Phe Ile Met Pro Val
                260                 265                 270

Pro Gly Asp Asn Ala Pro Gly Val Thr Phe Thr Ser Lys Asp Thr Leu
            275                 280                 285

Lys Gly Gly Lys Phe Tyr Arg
        290                 295

<210> SEQ ID NO 15
<211> LENGTH: 1464
<212> TYPE: DNA
<213> ORGANISM: Artificial Sequence
<220> FEATURE:
<223> OTHER INFORMATION: Synthetic sequence encoding AXN-8

<400> SEQUENCE: 15
atgtctacct ctaggcaaga tgttgctaag ttgggaccag atggaacaa ggtgttgctt      60 aactacgctc ttgctatgca agctcttgat gagcaaccta tcgctgatag aaactcctgg    120
aagttccttg agctatgca tggattccat ccacagcttt ggattaacga gaggctcatt    180
aagtctggtg ctccaattcc agctgatctt accaaccata cctatggaaa ccagtgccaa    240
catggatctt gtatttcttt gtcttggcac agggcttatc ttttcgcttt cgaggctatt    300
gtggctgcta aggtgaaaga actcaccggt gatgattggg ctttgccata ctggaactac    360
cttgattctt ctaaccctca ggctctttat cttccagatg cttttcgttgc taagactctc    420 ccagatggaa agccaaaccc acttaacaag tacccaagaa ggccaggtat taaggctatt    480
aagccagtga ggattctc tttggaagct atggatgaga acgatttcat tgtgggaaac    540
ggaactcttg gattcggagg tggaattacc ggaaacttcg ttcaattcga tggtgttgct    600
ggtgaacttg agactaaccc acataacacc gttcatggac ttgttggagg ttatatggga    660
aacgctctcc ttgctggact tgatccaatt ttctggcttc accactgcaa cattgataga    720
ctttgggagg cttggatgaa cactcctgga agactatgg tgcgtgatcc actttggctt    780
aacggaccag ctgatagatc tttcatcatg ccagtgccag tgataacgc tccaggtgtt    840 actttcacct ctaaggatac ccttaagggt ggaaagttct acaggaccta cgatgatctc    900
attattggaa ccggtgttac tccaggtgtt catgctgttg ctagggttaa catgggatct    960
ccatctaagc aaaccgttca gccaattgga gctaacgctg ctgttgttaa gattggaggt    1020
```

```
gctccagttg gaacccatat tgatcttgag ccaactgctg ctgctaactc tatggctact   1080
atgggagcta cttctccagg aaaagaggtt gcaaggcttt acttgtctct tgagtctgtt   1140
agaggatctg ctccttctcc acttcttgat gtgtacgtga accttccaga aggtgctgat   1200
ccagctttgt ctccagatag atacgctgga tctcttaccc ttttcggact taacgttgct   1260
tctcaaaccg atggaccaca tgctggatct ggacttggat acaccatcga tattaccgat   1320
cttgctcaga gacttgctga tgctggtgat ttcgatccaa accatcttag ggttacccct   1380
gttccaggtg aacaaatcac tgacgaggaa cctattaccg ttgagaggat ttctgtgctt   1440
aagagatccg gaattgtgtc ctga                                          1464

<210> SEQ ID NO 16
<211> LENGTH: 2205
<212> TYPE: DNA
<213> ORGANISM: Glycine max

<400> SEQUENCE: 16
gatacgcaat ttggagaaag gaagaagata agctagctaa ggcagcaatg ggtaatcctt     60
ctaagctttt cccattttc tttgcattca ttgtgtttct gatgccctta gtttccttat    120
cccacaatga cttctctacc tttgccataa aaaccgtttc atacctagtt tcctttagtg    180
aaaatccaaa ccataatggc cacatcacca caagctccaa tgaaagagac aaatcacgtc    240
tttggaggaa agccttcatt ggcttaaaaa atactcacga gccatcttcg aatatttctc    300
gagcaatatc ccttaatgca agagagtgtt ttcctgtgga gttaccttct gatgcaataa    360
cttctacccg ttgttgtcca cctaggccat ctccttctaa tatcatagat ttcaaagatt    420
ttgcttctcc aaacgccacg cttcgagtaa gaaaacctgc tcacatggta gatgaggagt    480
acatagcaaa acttgaaaag ggcattgcac tcatgaaagc actccctgat gatgacccac    540
gtaatttcat tcaacaagca aaggtccatt gcgcttattg taacggtgcc tatcacctac    600
gccatccctt tcaggacaca aaactcaaca ttcacaggtc ttggttttc tttcccttc     660 atcgttggta cctttacttc tttgagagaa ctttgggaaa attaattggt gacccaaact    720
ttgccctacc cttttggaat tgggattctg tagaagggat gcaaattcca tcatatttca    780
ataaccctaa ttcgtcgctt tatcaccaac tccgaaacca aaaccacttg ccccacacg     840 tggttgatct gaactacaat aaacttgatc ctaatgatga tacgccttct catcaacaag    900
tttcgtataa tctagccttc atgtacaagc aaatggtgct agcaagtacc aaagaattgt    960
tcatgggaag ccctttttcgc cttggcgata accctactcc gggtatgggc tctatagagg   1020
ctgctcctca taacactgtt catacatggg tgggtgctgc tgataagcca accatgaag    1080 acatgggagc attctacaca gcagctagag acccccatttt ctacgctcat cacccgaact   1140
cggatcgatt gtgggggcta tggaagacat tggaaggagg aagaaaggac tatagtgatg   1200
atccagattg gttagattct gagttttact tctatgatga gaatgccaat tttgttcgtg   1260
ttaaggtaag agattgcctt gatactaaaa aattagggta tgtttacgaa gatgttgatc   1320
ttccatggct gcgaacgcca cccacatcgc cgaaaagcaa gctactgaga gaagcgaaga   1380
agagtccact tttgagttca agccaagca aatttccttt ggttttggat tccataacga   1440
gtaccgttgt taagaggccg aagaaattga gaagcaagga gagaaagaa caagaggagg   1500 aggttttggt gatagaaggg attgagtttg gaagtgataa atatgtaaag tttgatgttc   1560
atattgatga tgatgaagat aaatttgagtg aaccggatca gacagagttt gtgggaactt   1620
ttgttaattt gttccatgga caaggccata atatcaacac tagttttaag gtagggatat   1680
```

-continued

```
cgaaagtgct ggagtgttta gaagctgaag aagatgatgt tgtgctggtt actttggtgc    1740
ctaaggttgg gaaggagat gtcatcatag gaggcatcaa aattgagttt attccaaagt     1800
agaaagatta gttttgttgt tgtgtgtgca aatttaatac acttattaca ggtttattgt    1860
tttatgcttt taaaaagtac actttctttt ttggtttagc atctcgagct cgtattctca    1920
gtggctggat tttgtccaac caactgaaat atgagatgtc gaatttgctt tggtatagcg    1980
atagtagaag aagggaaaga agggaaagag tgtgaaggac agctgaaatt ttggatgcgg    2040
agaagtactc ttctacaagt atagatgagt gttttgaag aaaatcaaat aaatcaattt     2100
gattttctag aattaatttt cataataaaa tatgagtctg gtgtaaaaat ttgtatttga    2160 ttttttttt atgtgaaagg tgattttagc aaaaaaaaaa aaaaa                    2205
```

<210> SEQ ID NO 17
<211> LENGTH: 1509
<212> TYPE: DNA
<213> ORGANISM: Artificial Sequence
<220> FEATURE:
<223> OTHER INFORMATION: Synthetic sequence encoding the polyphenol
      oxidase from Glycine max
<220> FEATURE:
<221> NAME/KEY: CDS
<222> LOCATION: (1)...(1509)

<400> SEQUENCE: 17

```
atg tcc agg gct att tct ctt aac gct aga gag tgc ttc cca gtt gaa     48
Met Ser Arg Ala Ile Ser Leu Asn Ala Arg Glu Cys Phe Pro Val Glu
1               5                   10                  15 ctt cca tct gat gct att act tct act aga tgc tgc cca cca aga cca     96
Leu Pro Ser Asp Ala Ile Thr Ser Thr Arg Cys Cys Pro Pro Arg Pro
                20                  25                  30 tct cca tcc aac atc atc gac ttc aag gat ttc gct tct cca aac gct    144
Ser Pro Ser Asn Ile Ile Asp Phe Lys Asp Phe Ala Ser Pro Asn Ala
            35                  40                  45 act ctt aga gtt aga aag cca gct cat atg gtg gat gaa gag tac att    192
Thr Leu Arg Val Arg Lys Pro Ala His Met Val Asp Glu Glu Tyr Ile
        50                  55                  60 gca aag ctc gag aag gga att gct ctt atg aag gct ctc cca gat gat    240
Ala Lys Leu Glu Lys Gly Ile Ala Leu Met Lys Ala Leu Pro Asp Asp
65                  70                  75                  80 gat cct agg aac ttc att cag cag gct aag gtt cac tgc gct tat tgc    288
Asp Pro Arg Asn Phe Ile Gln Gln Ala Lys Val His Cys Ala Tyr Cys
                85                  90                  95 aac ggt gct tac cat ctt aga cac cca ttc cag gat acc aag ctc aac    336
Asn Gly Ala Tyr His Leu Arg His Pro Phe Gln Asp Thr Lys Leu Asn
                100                 105                 110 att cat agg tcc tgg ttc ttt ttc cca ttc cac cgt tgg tat ctc tat    384
Ile His Arg Ser Trp Phe Phe Phe Pro Phe His Arg Trp Tyr Leu Tyr
            115                 120                 125 ttc ttc gag agg acc ctt gga aag ttg att ggc gat cca aac ttc gct    432
Phe Phe Glu Arg Thr Leu Gly Lys Leu Ile Gly Asp Pro Asn Phe Ala
        130                 135                 140 ttg cca ttc tgg aac tgg gat tct gtt gag gga atg caa atc cca tcc    480
Leu Pro Phe Trp Asn Trp Asp Ser Val Glu Gly Met Gln Ile Pro Ser
145                 150                 155                 160 tac ttc aac aac cca aac tct tca ctt tac cac caa ctc agg aac cag    528
Tyr Phe Asn Asn Pro Asn Ser Ser Leu Tyr His Gln Leu Arg Asn Gln
                165                 170                 175 aac cat ctt cca cca cat gtt gtg gat ctc aac tac aac aag ctc gat    576
Asn His Leu Pro Pro His Val Val Asp Leu Asn Tyr Asn Lys Leu Asp
                180                 185                 190
```

```
cca aac gat gat act cca tct cat cag cag gtg tca tac aac ctt gcc    624
Pro Asn Asp Asp Thr Pro Ser His Gln Gln Val Ser Tyr Asn Leu Ala
        195                 200                 205 ttc atg tac aag cag atg gtt ctt gct tct acc aaa gaa ctc ttc atg    672
Phe Met Tyr Lys Gln Met Val Leu Ala Ser Thr Lys Glu Leu Phe Met
    210                 215                 220 gga tct cca ttc aga ctt gga gat aac cca act cca gga atg gga tct    720
Gly Ser Pro Phe Arg Leu Gly Asp Asn Pro Thr Pro Gly Met Gly Ser
225                 230                 235                 240 att gaa gct gct cca cat aac act gtt cat act tgg gtt ggt gct gct    768
Ile Glu Ala Ala Pro His Asn Thr Val His Thr Trp Val Gly Ala Ala
                245                 250                 255 gat aag cca cat cat gag gat atg gga gct ttc tat act gct gct agg    816
Asp Lys Pro His His Glu Asp Met Gly Ala Phe Tyr Thr Ala Ala Arg
            260                 265                 270 gac cca att ttc tac gct cat cac cca aac tct gat aga ctt tgg gga    864
Asp Pro Ile Phe Tyr Ala His His Pro Asn Ser Asp Arg Leu Trp Gly
        275                 280                 285 ctt tgg aaa act ctt gag ggc gga aga aag gat tat tcc gat gat cca    912
Leu Trp Lys Thr Leu Glu Gly Gly Arg Lys Asp Tyr Ser Asp Asp Pro
    290                 295                 300 gat tgg ctt gat tcc gag ttc tac ttc tac gat gag aac gct aac ttt    960
Asp Trp Leu Asp Ser Glu Phe Tyr Phe Tyr Asp Glu Asn Ala Asn Phe
305                 310                 315                 320 gtt agg gtg aaa gtg agg gat tgc ctt gat aca aag aag ctc ggc tac   1008
Val Arg Val Lys Val Arg Asp Cys Leu Asp Thr Lys Lys Leu Gly Tyr
                325                 330                 335 gtt tac gaa gat gtg gat ctt cca tgg ctt aga act cca cca act tct   1056
Val Tyr Glu Asp Val Asp Leu Pro Trp Leu Arg Thr Pro Pro Thr Ser
            340                 345                 350 cca aag tct aag ctc ctt aga gag gct aag aag tct cca ctt ttg tcc   1104
Pro Lys Ser Lys Leu Leu Arg Glu Ala Lys Lys Ser Pro Leu Leu Ser
        355                 360                 365 tct aag cca tct aag ttc cca ctt gtg ctc gat tct att acc tct acc   1152
Ser Lys Pro Ser Lys Phe Pro Leu Val Leu Asp Ser Ile Thr Ser Thr
    370                 375                 380 gtt gtg aag agg cca aag aag ttg agg tcc aaa gaa gag aaa gag caa   1200
Val Val Lys Arg Pro Lys Lys Leu Arg Ser Lys Glu Glu Lys Glu Gln
385                 390                 395                 400 gag gaa gag gtt ttg gtt att gag gga att gag ttc ggt tct gac aag   1248
Glu Glu Glu Val Leu Val Ile Glu Gly Ile Glu Phe Gly Ser Asp Lys
                405                 410                 415 tac gtt aag ttc gac gtg cac atc gat gat gag gat aac ctt tct       1296
Tyr Val Lys Phe Asp Val His Ile Asp Asp Glu Asp Asn Leu Ser
            420                 425                 430 gag cca gat caa act gag ttc gtt ggt act ttc gtg aac ctt ttc cat   1344
Glu Pro Asp Gln Thr Glu Phe Val Gly Thr Phe Val Asn Leu Phe His
        435                 440                 445 gga cag gga cac aac att aac acc agc ttc aaa gtg gga att tct aag   1392
Gly Gln Gly His Asn Ile Asn Thr Ser Phe Lys Val Gly Ile Ser Lys
    450                 455                 460 gtg ttg gag tgc ctt gaa gct gaa gag gat gat gtt gtg ctt gtt acc   1440
Val Leu Glu Cys Leu Glu Ala Glu Glu Asp Asp Val Val Leu Val Thr
465                 470                 475                 480 ctt gtt cca aaa gtg gga aag ggt gat gtg att att gga ggc atc aag   1488
Leu Val Pro Lys Val Gly Lys Gly Asp Val Ile Ile Gly Gly Ile Lys
                485                 490                 495 atc gag ttc atc cca aag tga                                       1509
Ile Glu Phe Ile Pro Lys
                500
```

<210> SEQ ID NO 18
<211> LENGTH: 502
<212> TYPE: PRT
<213> ORGANISM: Artificial Sequence
<220> FEATURE:
<223> OTHER INFORMATION: Amino acid sequence encoded by the synthetic
sequence encoding the polyphenol oxidase from
Glycine max

<400> SEQUENCE: 18

```
Met Ser Arg Ala Ile Ser Leu Asn Ala Arg Glu Cys Phe Pro Val Glu
 1               5                  10                  15

Leu Pro Ser Asp Ala Ile Thr Ser Thr Arg Cys Cys Pro Pro Arg Pro
            20                  25                  30

Ser Pro Ser Asn Ile Ile Asp Phe Lys Asp Phe Ala Ser Pro Asn Ala
        35                  40                  45

Thr Leu Arg Val Arg Lys Pro Ala His Met Val Asp Glu Glu Tyr Ile
 50                  55                  60

Ala Lys Leu Glu Lys Gly Ile Ala Leu Met Lys Ala Leu Pro Asp Asp
 65                  70                  75                  80

Asp Pro Arg Asn Phe Ile Gln Gln Ala Lys Val His Cys Ala Tyr Cys
                85                  90                  95

Asn Gly Ala Tyr His Leu Arg His Pro Phe Gln Asp Thr Lys Leu Asn
            100                 105                 110

Ile His Arg Ser Trp Phe Phe Phe Pro Phe His Arg Trp Tyr Leu Tyr
        115                 120                 125

Phe Phe Glu Arg Thr Leu Gly Lys Leu Ile Gly Asp Pro Asn Phe Ala
130                 135                 140

Leu Pro Phe Trp Asn Trp Asp Ser Val Glu Gly Met Gln Ile Pro Ser
145                 150                 155                 160

Tyr Phe Asn Asn Pro Asn Ser Ser Leu Tyr His Gln Leu Arg Asn Gln
                165                 170                 175

Asn His Leu Pro Pro His Val Val Asp Leu Asn Tyr Asn Lys Leu Asp
            180                 185                 190

Pro Asn Asp Asp Thr Pro Ser His Gln Gln Val Ser Tyr Asn Leu Ala
        195                 200                 205

Phe Met Tyr Lys Gln Met Val Leu Ala Ser Thr Lys Glu Leu Phe Met
210                 215                 220

Gly Ser Pro Phe Arg Leu Gly Asp Asn Pro Thr Pro Gly Met Gly Ser
225                 230                 235                 240

Ile Glu Ala Ala Pro His Asn Thr Val His Thr Trp Val Gly Ala Ala
                245                 250                 255

Asp Lys Pro His His Glu Asp Met Gly Ala Phe Tyr Thr Ala Ala Arg
            260                 265                 270

Asp Pro Ile Phe Tyr Ala His His Pro Asn Ser Asp Arg Leu Trp Gly
        275                 280                 285

Leu Trp Lys Thr Leu Glu Gly Gly Arg Lys Asp Tyr Ser Asp Asp Pro
290                 295                 300

Asp Trp Leu Asp Ser Glu Phe Tyr Phe Tyr Asp Glu Asn Ala Asn Phe
305                 310                 315                 320

Val Arg Val Lys Val Arg Asp Cys Leu Asp Thr Lys Lys Leu Gly Tyr
                325                 330                 335

Val Tyr Glu Asp Val Asp Leu Pro Trp Leu Arg Thr Pro Pro Thr Ser
            340                 345                 350

Pro Lys Ser Lys Leu Leu Arg Glu Ala Lys Lys Ser Pro Leu Leu Ser
```

```
                    355                 360                 365
Ser Lys Pro Ser Lys Phe Pro Leu Val Leu Asp Ser Ile Thr Ser Thr
            370                 375                 380

Val Val Lys Arg Pro Lys Lys Leu Arg Ser Lys Glu Glu Lys Glu Gln
385                 390                 395                 400

Glu Glu Glu Val Leu Val Ile Glu Gly Ile Glu Phe Gly Ser Asp Lys
                405                 410                 415

Tyr Val Lys Phe Asp Val His Ile Asp Asp Glu Asp Asn Leu Ser
            420                 425                 430

Glu Pro Asp Gln Thr Glu Phe Val Gly Thr Phe Val Asn Leu Phe His
            435                 440                 445

Gly Gln Gly His Asn Ile Asn Thr Ser Phe Lys Val Gly Ile Ser Lys
        450                 455                 460

Val Leu Glu Cys Leu Glu Ala Glu Glu Asp Asp Val Val Leu Val Thr
465                 470                 475                 480

Leu Val Pro Lys Val Gly Lys Gly Asp Val Ile Gly Gly Ile Lys
                485                 490                 495

Ile Glu Phe Ile Pro Lys
            500

<210> SEQ ID NO 19
<211> LENGTH: 2404
<212> TYPE: DNA
<213> ORGANISM: Hypocrea jecorina

<400> SEQUENCE: 19
atgctgttgt cagcgtccct ctcggcgttg gccttggcca cagtttcact cgcacagggc      60
acgacacaca tccccgtcac cggtgttccc gtctctcctg gtgctgccgt gccgctgaga     120
cagaacatca atgacctggc caagtccggg ccgcaatggt gagtgacgcc ctccttccac     180
cacactttac ctcagtcaag agacaagagg gagacaagta caaagcggat gaaaagaggt     240
ggacaagaga gagagagaga gaaagtgtgt gtgtgtatgt gagagcgaga gagagagaga     300
gagacaagag ctattggatg gaccaggagc cagcatggag aacaggggga gacttgacga     360
ttcgaggaga gggggggctca catgtgcgtg cgaatagga tctctacgtt caggccatgt      420
acaacatgtc caagatggac tcccatgacc cgtacagctt cttccagatt gccggtaaat     480
atacatctcg gcctcctgcg aggcgacgtg actctcggag cttttagtaa caccagctag     540
gcatccacgg cgcaccgtac attgagtaca acaaggccgg agcaaagtcg ggcgatggct     600
ggctgggcta ctgccctcac ggtgtatgtg tttttgtcca tcgaggaggg cgcaagagtt     660
tcatggactt gaactcttcg cccttgttgt gagccggaaa tcatcgtctc tgacagtttc     720
attaggagga cctcttcatc agctggcacc gcccctatgt cctgctcttt gaggtatgat     780
ttgaccacgc tggactttga cctcatacaa acatcaactg catcgttgc agcaagcctt      840 ggtctccgtc gccaagggca tcgccaactc gtatccccg tctgtccgcg ccaagtacca      900
ggctgccgcc gccagcctgc gcgcccccta ctgggactgg gccgccgaca gctccgtgcc     960
cgccgtcacc gtcccccaga cgctcaagat caacgtcccc agcggcagca gcaccaagac    1020
cgtcgactac accaacccgc tcaagacgta ctacttcccg cgcatgtcct tgaccggctc    1080
gtacggcgag ttcaccggcg aggcaacga ccacaccgtc cgctgcgccg cctccaagca    1140
gagctatccc gccaccgcca actccaacct ggctgcccgt ccttacaagt cctggatcgt    1200
acgtagtccc ccttttccctt tggaagcttc cccttgagta aagctcgtca ctgacacaga    1260
gagcggcccg cagtacgatg tcctgaccaa ctctcaaaac tttgccgact cgcctccac    1320
```

-continued

```
cagcggcccc ggcatcaacg ttgagcagat ccacaacgcc atccactggg acggtgcttg    1380
cggctcccag ttcctcgccc ccgactactc cggcttcgac ccctgttgt aagtcaatcg     1440 agacgtcaag agtcatcttg tcaacaaccg atggcaaacg cagtctgtac tgacgctgca    1500
aaatagcttc atgcaccacg cccaggtcga ccgcatgtgg gccttctggg aggccatcat    1560
gccctcgtcg cccctcttca cggcctcgta caagggccag tcgcgcttca actccaagtc    1620
gggcagcacc atcaccccg actcgcccct gcagcccttc taccaggcca acggcaagtt    1680
ccacacgtcc aacacggtca agagcatcca gggcatgggc tactcgtacc agggcatcga    1740
gtactggcaa aagtcccagg cccagatcaa gtcgagcgtc accaccatca tcaaccagct    1800
gtacgggccc aactcgggca agaagcgcaa cgccccgcgc gacttcttga gcgacattgt    1860
caccgacgtc gagaacctca tcaagacccg ttactttgcc aagatctcgg tcaacgtgac    1920
cgaggtgacg gtccgccccg ccgagatcaa cgtctacgtc ggcggccaga aggccggcag    1980
cttgatcgtc atgaagctcc ccgccgaggg cacggtcaac ggcggcttca ccattgacaa    2040
ccccatgcaa agcatcctgc acggtggtct ccgcaacgcc gtccaggcct ttaccgagga    2100
cattgaggtt gagattctct ctgtaagttt tcccccctct ctccactccc gaccactcac    2160
tgtcactatt tcgactagtc accgtcaaga tgtgtatttg tttgctgacc cccaagcgca    2220
gaaggacgga caagccatcc ccctcgagac ggtccccagc ctgtccatcg acctcgaggt    2280
cgccaacgtc accctgccct ccgccctcga ccagctgccc aagtacggcc agcgctccag    2340
gcaccgcgcc aaggccgccc agcgcggaca ccgctttgcc gttccccata tccctcctct    2400
gtaa                                                                 2404
```

<210> SEQ ID NO 20
<211> LENGTH: 561
<212> TYPE: PRT
<213> ORGANISM: Hypocrea jecorina

<400> SEQUENCE: 20

```
Met Leu Leu Ser Ala Ser Leu Ser Ala Leu Ala Leu Ala Thr Val Ser
  1               5                  10                  15

Leu Ala Gln Gly Thr Thr His Ile Pro Val Thr Gly Val Pro Val Ser
                 20                  25                  30

Pro Gly Ala Ala Val Pro Leu Arg Gln Asn Ile Asn Asp Leu Ala Lys
             35                  40                  45

Ser Gly Pro Gln Trp Asp Leu Tyr Val Gln Ala Met Tyr Asn Met Ser
         50                  55                  60

Lys Met Asp Ser His Asp Pro Tyr Ser Phe Phe Gln Ile Ala Gly Ile
 65                  70                  75                  80

His Gly Ala Pro Tyr Ile Glu Tyr Asn Lys Ala Gly Ala Lys Ser Gly
                 85                  90                  95

Asp Gly Trp Leu Gly Tyr Cys Pro His Gly Glu Asp Leu Phe Ile Ser
            100                 105                 110

Trp His Arg Pro Tyr Val Leu Leu Phe Glu Gln Ala Leu Val Ser Val
        115                 120                 125

Ala Lys Gly Ile Ala Asn Ser Tyr Pro Pro Ser Val Arg Ala Lys Tyr
    130                 135                 140

Gln Ala Ala Ala Ala Ser Leu Arg Ala Pro Tyr Trp Asp Trp Ala Ala
145                 150                 155                 160

Asp Ser Ser Val Pro Ala Val Thr Val Pro Gln Thr Leu Lys Ile Asn
                165                 170                 175
```

-continued

Val Pro Ser Gly Ser Ser Thr Lys Thr Val Asp Tyr Thr Asn Pro Leu
            180                 185                 190

Lys Thr Tyr Tyr Phe Pro Arg Met Ser Leu Thr Gly Ser Tyr Gly Glu
        195                 200                 205

Phe Thr Gly Gly Asn Asp His Thr Val Arg Cys Ala Ala Ser Lys
    210                 215                 220

Gln Ser Tyr Pro Ala Thr Ala Asn Ser Asn Leu Ala Ala Arg Pro Tyr
225                 230                 235                 240

Lys Ser Trp Ile Tyr Asp Val Leu Thr Asn Ser Gln Asn Phe Ala Asp
                245                 250                 255

Phe Ala Ser Thr Ser Gly Pro Gly Ile Asn Val Glu Gln Ile His Asn
            260                 265                 270

Ala Ile His Trp Asp Gly Ala Cys Gly Ser Gln Phe Leu Ala Pro Asp
        275                 280                 285

Tyr Ser Gly Phe Asp Pro Leu Phe Phe Met His His Ala Gln Val Asp
    290                 295                 300

Arg Met Trp Ala Phe Trp Glu Ala Ile Met Pro Ser Ser Pro Leu Phe
305                 310                 315                 320

Thr Ala Ser Tyr Lys Gly Gln Ser Arg Phe Asn Ser Lys Ser Gly Ser
                325                 330                 335

Thr Ile Thr Pro Asp Ser Pro Leu Gln Pro Phe Tyr Gln Ala Asn Gly
            340                 345                 350

Lys Phe His Thr Ser Asn Thr Val Lys Ser Ile Gln Gly Met Gly Tyr
        355                 360                 365

Ser Tyr Gln Gly Ile Glu Tyr Trp Gln Lys Ser Gln Ala Gln Ile Lys
    370                 375                 380

Ser Ser Val Thr Thr Ile Ile Asn Gln Leu Tyr Gly Pro Asn Ser Gly
385                 390                 395                 400

Lys Lys Arg Asn Ala Pro Arg Asp Phe Leu Ser Asp Ile Val Thr Asp
                405                 410                 415

Val Glu Asn Leu Ile Lys Thr Arg Tyr Phe Ala Lys Ile Ser Val Asn
            420                 425                 430

Val Thr Glu Val Thr Val Arg Pro Ala Glu Ile Asn Val Tyr Val Gly
        435                 440                 445

Gly Gln Lys Ala Gly Ser Leu Ile Val Met Lys Leu Pro Ala Glu Gly
    450                 455                 460

Thr Val Asn Gly Gly Phe Thr Ile Asp Asn Pro Met Gln Ser Ile Leu
465                 470                 475                 480

His Gly Gly Leu Arg Asn Ala Val Gln Ala Phe Thr Glu Asp Ile Glu
                485                 490                 495

Val Glu Ile Leu Ser Lys Asp Gly Gln Ala Ile Pro Leu Glu Thr Val
            500                 505                 510

Pro Ser Leu Ser Ile Asp Leu Glu Val Ala Asn Val Thr Leu Pro Ser
        515                 520                 525

Ala Leu Asp Gln Leu Pro Lys Tyr Gly Gln Arg Ser Arg His Arg Ala
    530                 535                 540

Lys Ala Ala Gln Arg Gly His Arg Phe Ala Val Pro His Ile Pro Pro
545                 550                 555                 560

Leu

<210> SEQ ID NO 21
<211> LENGTH: 1686
<212> TYPE: DNA
<213> ORGANISM: Artificial Sequence
<220> FEATURE:

<223> OTHER INFORMATION: Synthetic sequence encoding the polyphenol oxidase from T. reesei
<220> FEATURE:
<221> NAME/KEY: CDS
<222> LOCATION: (1)...(1686)

<400> SEQUENCE: 21

| | | | | | | | | | | | | | | | | |
|---|---|---|---|---|---|---|---|---|---|---|---|---|---|---|---|---|
| atg | ctt | ctt | tct | gct | tct | ctt | tct | gct | ctt | gct | ctt | gct | act | gtt | tct | 48 |
| Met | Leu | Leu | Ser | Ala | Ser | Leu | Ser | Ala | Leu | Ala | Leu | Ala | Thr | Val | Ser | |
| 1 | | | | 5 | | | | | 10 | | | | | 15 | | |
| ctt | gct | cag | gga | acc | act | cat | att | cca | gtt | act | ggt | gtt | cca | gtt | tct | 96 |
| Leu | Ala | Gln | Gly | Thr | Thr | His | Ile | Pro | Val | Thr | Gly | Val | Pro | Val | Ser | |
| | | | 20 | | | | | 25 | | | | | 30 | | | |
| cca | ggt | gct | gct | gtt | cca | ctt | agg | cag | aac | att | aac | gat | ctt | gct | aag | 144 |
| Pro | Gly | Ala | Ala | Val | Pro | Leu | Arg | Gln | Asn | Ile | Asn | Asp | Leu | Ala | Lys | |
| | | 35 | | | | | 40 | | | | | 45 | | | | |
| tct | gga | cca | caa | tgg | gat | ctt | tac | gtt | cag | gcc | atg | tac | aac | atg | tct | 192 |
| Ser | Gly | Pro | Gln | Trp | Asp | Leu | Tyr | Val | Gln | Ala | Met | Tyr | Asn | Met | Ser | |
| | 50 | | | | | 55 | | | | | 60 | | | | | |
| aag | atg | gat | tcc | cac | gac | cca | tat | tca | ttc | ttc | cag | atc | gct | ggt | att | 240 |
| Lys | Met | Asp | Ser | His | Asp | Pro | Tyr | Ser | Phe | Phe | Gln | Ile | Ala | Gly | Ile | |
| 65 | | | | | 70 | | | | | 75 | | | | | 80 | |
| cat | ggt | gct | ccc | tac | att | gag | tat | aac | aag | gct | ggt | gct | aag | tca | ggt | 288 |
| His | Gly | Ala | Pro | Tyr | Ile | Glu | Tyr | Asn | Lys | Ala | Gly | Ala | Lys | Ser | Gly | |
| | | | | 85 | | | | | 90 | | | | | 95 | | |
| gat | gga | tgg | ctt | gga | tat | tgc | cca | cat | ggt | gaa | gat | ctt | ttc | att | tcc | 336 |
| Asp | Gly | Trp | Leu | Gly | Tyr | Cys | Pro | His | Gly | Glu | Asp | Leu | Phe | Ile | Ser | |
| | | | 100 | | | | | 105 | | | | | 110 | | | |
| tgg | cat | agg | cca | tac | gtt | ctt | ttg | ttc | gag | cag | gct | ctt | gtt | tct | gtt | 384 |
| Trp | His | Arg | Pro | Tyr | Val | Leu | Leu | Phe | Glu | Gln | Ala | Leu | Val | Ser | Val | |
| | | 115 | | | | | 120 | | | | | 125 | | | | |
| gct | aag | ggt | atc | gct | aac | tct | tat | cca | cca | tct | gtt | agg | gct | aag | tat | 432 |
| Ala | Lys | Gly | Ile | Ala | Asn | Ser | Tyr | Pro | Pro | Ser | Val | Arg | Ala | Lys | Tyr | |
| | 130 | | | | | 135 | | | | | 140 | | | | | |
| caa | gct | gct | gct | gct | tct | ctt | agg | gct | cca | tat | tgg | gat | tgg | gct | gct | 480 |
| Gln | Ala | Ala | Ala | Ala | Ser | Leu | Arg | Ala | Pro | Tyr | Trp | Asp | Trp | Ala | Ala | |
| 145 | | | | | 150 | | | | | 155 | | | | | 160 | |
| gat | tct | tct | gtt | cca | gct | gtt | act | gtt | cca | cag | acc | ctc | aag | att | aac | 528 |
| Asp | Ser | Ser | Val | Pro | Ala | Val | Thr | Val | Pro | Gln | Thr | Leu | Lys | Ile | Asn | |
| | | | | 165 | | | | | 170 | | | | | 175 | | |
| gtt | cca | tct | gga | tct | tct | acc | aag | acc | gtg | gat | tac | act | aac | cca | ctc | 576 |
| Val | Pro | Ser | Gly | Ser | Ser | Thr | Lys | Thr | Val | Asp | Tyr | Thr | Asn | Pro | Leu | |
| | | | 180 | | | | | 185 | | | | | 190 | | | |
| aag | act | tac | tat | ttc | cca | agg | atg | tct | ctt | act | gga | tct | tac | ggt | gag | 624 |
| Lys | Thr | Tyr | Tyr | Phe | Pro | Arg | Met | Ser | Leu | Thr | Gly | Ser | Tyr | Gly | Glu | |
| | | | 195 | | | | | 200 | | | | | 205 | | | |
| ttc | act | ggt | gga | gga | aac | gat | cat | act | gtt | aga | tgc | gct | gct | tct | aag | 672 |
| Phe | Thr | Gly | Gly | Gly | Asn | Asp | His | Thr | Val | Arg | Cys | Ala | Ala | Ser | Lys | |
| | 210 | | | | | 215 | | | | | 220 | | | | | |
| caa | tct | tac | cca | gct | act | gct | aac | tct | aac | ctt | gct | gct | aga | cca | tac | 720 |
| Gln | Ser | Tyr | Pro | Ala | Thr | Ala | Asn | Ser | Asn | Leu | Ala | Ala | Arg | Pro | Tyr | |
| 225 | | | | | 230 | | | | | 235 | | | | | 240 | |
| aag | tcc | tgg | atc | tac | gat | gtt | ctt | acc | aac | tct | cag | aac | ttc | gct | gat | 768 |
| Lys | Ser | Trp | Ile | Tyr | Asp | Val | Leu | Thr | Asn | Ser | Gln | Asn | Phe | Ala | Asp | |
| | | | | 245 | | | | | 250 | | | | | 255 | | |
| ttc | gct | tct | act | tcc | gga | cca | ggt | att | aac | gtt | gag | cag | atc | cac | aac | 816 |
| Phe | Ala | Ser | Thr | Ser | Gly | Pro | Gly | Ile | Asn | Val | Glu | Gln | Ile | His | Asn | |
| | | | 260 | | | | | 265 | | | | | 270 | | | |
| gct | att | cat | tgg | gat | ggt | gct | tgc | gga | tct | caa | ttc | ctt | gct | cca | gat | 864 |
| Ala | Ile | His | Trp | Asp | Gly | Ala | Cys | Gly | Ser | Gln | Phe | Leu | Ala | Pro | Asp | |
| | | 275 | | | | | 280 | | | | | 285 | | | | |

```
tac tct gga ttc gac cca ctt ttc ttc atg cat cat gct caa gtt gat    912
Tyr Ser Gly Phe Asp Pro Leu Phe Phe Met His His Ala Gln Val Asp
    290             295             300 agg atg tgg gct ttc tgg gaa gct att atg cca tct tct cca ctt ttc    960
Arg Met Trp Ala Phe Trp Glu Ala Ile Met Pro Ser Ser Pro Leu Phe
305             310             315             320 acc gct tca tac aag gga caa tcc agg ttc aac tct aag tct ggt tct   1008
Thr Ala Ser Tyr Lys Gly Gln Ser Arg Phe Asn Ser Lys Ser Gly Ser
            325             330             335 acc att act cca gat tct cca ctt caa cca ttc tac cag gct aac gga   1056
Thr Ile Thr Pro Asp Ser Pro Leu Gln Pro Phe Tyr Gln Ala Asn Gly
        340             345             350 aag ttc cat acc tct aac acc gtg aag tct att cag gga atg gga tac   1104
Lys Phe His Thr Ser Asn Thr Val Lys Ser Ile Gln Gly Met Gly Tyr
    355             360             365 tct tac cag gga att gag tac tgg caa aag tct cag gct cag att aag   1152
Ser Tyr Gln Gly Ile Glu Tyr Trp Gln Lys Ser Gln Ala Gln Ile Lys
370             375             380 tca tct gtg acc acc att atc aac cag ctt tac gga cca aac tct gga   1200
Ser Ser Val Thr Thr Ile Ile Asn Gln Leu Tyr Gly Pro Asn Ser Gly
385             390             395             400 aag aag aga aac gct cca agg gat ttc ctt tcc gat att gtg acc gat   1248
Lys Lys Arg Asn Ala Pro Arg Asp Phe Leu Ser Asp Ile Val Thr Asp
            405             410             415 gtg gag aac ctt att aag acc aga tac ttc gct aag att tcc gtt aac   1296
Val Glu Asn Leu Ile Lys Thr Arg Tyr Phe Ala Lys Ile Ser Val Asn
        420             425             430 gtt acc gaa gtt act gtt agg cca gct gag att aac gtt tat gtg gga   1344
Val Thr Glu Val Thr Val Arg Pro Ala Glu Ile Asn Val Tyr Val Gly
    435             440             445 gga caa aag gct gga tct ctc att gtg atg aag ttg cca gct gag gga   1392
Gly Gln Lys Ala Gly Ser Leu Ile Val Met Lys Leu Pro Ala Glu Gly
450             455             460 act gtt aac ggt gga ttc acc att gat aac ccc atg caa tcc att ctt   1440
Thr Val Asn Gly Gly Phe Thr Ile Asp Asn Pro Met Gln Ser Ile Leu
465             470             475             480 cat ggt gga ctt agg aac gct gtt cag gct ttc act gag gat att gag   1488
His Gly Gly Leu Arg Asn Ala Val Gln Ala Phe Thr Glu Asp Ile Glu
            485             490             495 gtg gag att ctc tct aag gat gga cag gct att cca ctt gag act gtg   1536
Val Glu Ile Leu Ser Lys Asp Gly Gln Ala Ile Pro Leu Glu Thr Val
        500             505             510 cca tct ctt agc att gat ctt gag gtt gca aac gtt act ctt cca tct   1584
Pro Ser Leu Ser Ile Asp Leu Glu Val Ala Asn Val Thr Leu Pro Ser
    515             520             525 gct ctt gat cag ctt cca aag tac gga caa aga tct aga cat agg gct   1632
Ala Leu Asp Gln Leu Pro Lys Tyr Gly Gln Arg Ser Arg His Arg Ala
530             535             540 aag gct gct caa aga gga cat aga ttc gct gtt cca cac att cca cca   1680
Lys Ala Ala Gln Arg Gly His Arg Phe Ala Val Pro His Ile Pro Pro
545             550             555             560 ctt tga                                                            1686
Leu
```

<210> SEQ ID NO 22
<211> LENGTH: 561
<212> TYPE: PRT
<213> ORGANISM: Artificial Sequence
<220> FEATURE:
<223> OTHER INFORMATION: Amino acid sequence encoded by the synthetic
      sequence encoding the polyphenol oxidase from T.
      reesei

<400> SEQUENCE: 22

```
Met Leu Leu Ser Ala Ser Leu Ser Ala Leu Ala Leu Ala Thr Val Ser
 1               5                  10                  15

Leu Ala Gln Gly Thr Thr His Ile Pro Val Thr Gly Val Pro Val Ser
             20                  25                  30

Pro Gly Ala Ala Val Pro Leu Arg Gln Asn Ile Asn Asp Leu Ala Lys
         35                  40                  45

Ser Gly Pro Gln Trp Asp Leu Tyr Val Gln Ala Met Tyr Asn Met Ser
 50                  55                  60

Lys Met Asp Ser His Asp Pro Tyr Ser Phe Phe Gln Ile Ala Gly Ile
 65                  70                  75                  80

His Gly Ala Pro Tyr Ile Glu Tyr Asn Lys Ala Gly Ala Lys Ser Gly
                 85                  90                  95

Asp Gly Trp Leu Gly Tyr Cys Pro His Gly Glu Asp Leu Phe Ile Ser
            100                 105                 110

Trp His Arg Pro Tyr Val Leu Leu Phe Glu Gln Ala Leu Val Ser Val
            115                 120                 125

Ala Lys Gly Ile Ala Asn Ser Tyr Pro Pro Ser Val Arg Ala Lys Tyr
130                 135                 140

Gln Ala Ala Ala Ser Leu Arg Ala Pro Tyr Trp Asp Trp Ala Ala
145                 150                 155                 160

Asp Ser Ser Val Pro Ala Val Thr Val Pro Gln Thr Leu Lys Ile Asn
                165                 170                 175

Val Pro Ser Gly Ser Ser Thr Lys Thr Val Asp Tyr Thr Asn Pro Leu
            180                 185                 190

Lys Thr Tyr Tyr Phe Pro Arg Met Ser Leu Thr Gly Ser Tyr Gly Glu
            195                 200                 205

Phe Thr Gly Gly Gly Asn Asp His Thr Val Arg Cys Ala Ala Ser Lys
210                 215                 220

Gln Ser Tyr Pro Ala Thr Ala Asn Ser Asn Leu Ala Ala Arg Pro Tyr
225                 230                 235                 240

Lys Ser Trp Ile Tyr Asp Val Leu Thr Asn Ser Gln Asn Phe Ala Asp
                245                 250                 255

Phe Ala Ser Thr Ser Gly Pro Gly Ile Asn Val Glu Gln Ile His Asn
            260                 265                 270

Ala Ile His Trp Asp Gly Ala Cys Gly Ser Gln Phe Leu Ala Pro Asp
            275                 280                 285

Tyr Ser Gly Phe Asp Pro Leu Phe Phe Met His His Ala Gln Val Asp
290                 295                 300

Arg Met Trp Ala Phe Trp Glu Ala Ile Met Pro Ser Ser Pro Leu Phe
305                 310                 315                 320

Thr Ala Ser Tyr Lys Gly Gln Ser Arg Phe Asn Ser Lys Ser Gly Ser
                325                 330                 335

Thr Ile Thr Pro Asp Ser Pro Leu Gln Pro Phe Tyr Gln Ala Asn Gly
            340                 345                 350

Lys Phe His Thr Ser Asn Thr Val Lys Ser Ile Gln Gly Met Gly Tyr
            355                 360                 365

Ser Tyr Gln Gly Ile Glu Tyr Trp Gln Lys Ser Gln Ala Gln Ile Lys
370                 375                 380

Ser Ser Val Thr Thr Ile Ile Asn Gln Leu Tyr Gly Pro Asn Ser Gly
385                 390                 395                 400

Lys Lys Arg Asn Ala Pro Arg Asp Phe Leu Ser Asp Ile Val Thr Asp
                405                 410                 415
```

```
Val Glu Asn Leu Ile Lys Thr Arg Tyr Phe Ala Lys Ile Ser Val Asn
            420                 425                 430

Val Thr Glu Val Thr Val Arg Pro Ala Glu Ile Asn Val Tyr Val Gly
        435                 440                 445

Gly Gln Lys Ala Gly Ser Leu Ile Val Met Lys Leu Pro Ala Glu Gly
    450                 455                 460

Thr Val Asn Gly Gly Phe Thr Ile Asp Asn Pro Met Gln Ser Ile Leu
465                 470                 475                 480

His Gly Gly Leu Arg Asn Ala Val Gln Ala Phe Thr Glu Asp Ile Glu
            485                 490                 495

Val Glu Ile Leu Ser Lys Asp Gly Gln Ala Ile Pro Leu Glu Thr Val
        500                 505                 510

Pro Ser Leu Ser Ile Asp Leu Glu Val Ala Asn Val Thr Leu Pro Ser
    515                 520                 525

Ala Leu Asp Gln Leu Pro Lys Tyr Gly Gln Arg Ser Arg His Arg Ala
    530                 535                 540

Lys Ala Ala Gln Arg Gly His Arg Phe Ala Val Pro His Ile Pro Pro
545                 550                 555                 560

Leu

<210> SEQ ID NO 23
<211> LENGTH: 10
<212> TYPE: PRT
<213> ORGANISM: Artificial Sequence
<220> FEATURE:
<223> OTHER INFORMATION: N-terminal sequence from trypsin fragments of
      the 50 kDa protein from ATX21995

<400> SEQUENCE: 23

Gly Thr Trp Ser Ile Ala Ala Gly Ser Arg
1               5                   10

<210> SEQ ID NO 24
<211> LENGTH: 12
<212> TYPE: PRT
<213> ORGANISM: Artificial Sequence
<220> FEATURE:
<223> OTHER INFORMATION: N-terminal sequence from trypsin fragments of
      the 50 kDa protein from ATX21995

<400> SEQUENCE: 24

Asp Ser Thr Gly Glu Phe Asn Ala Thr Leu Tyr Arg
1               5                   10

<210> SEQ ID NO 25
<211> LENGTH: 9
<212> TYPE: PRT
<213> ORGANISM: Artificial Sequence
<220> FEATURE:
<223> OTHER INFORMATION: N-terminal sequence from trypsin fragments of
      the 50 kDa protein from ATX21995

<400> SEQUENCE: 25

Ser Ala Pro Tyr Ala Ile Thr Gly Ile
1               5

<210> SEQ ID NO 26
<211> LENGTH: 14
<212> TYPE: PRT
<213> ORGANISM: Artificial Sequence
<220> FEATURE:
<223> OTHER INFORMATION: N-terminal sequence from trypsin fragments of
      the 50 kDa protein from ATX21995
```

<400> SEQUENCE: 26

Tyr Pro Asp Ala Trp Phe Asn Ala Gln Ser Ala Gln Leu Arg
1               5                   10

<210> SEQ ID NO 27
<211> LENGTH: 10
<212> TYPE: PRT
<213> ORGANISM: Artificial Sequence
<220> FEATURE:
<223> OTHER INFORMATION: N-terminal sequence from trypsin fragments of
      the 50 kDa protein from ATX21995

<400> SEQUENCE: 27

Phe Gly Ser Ser Tyr Pro Glu Leu Gln Pro
1               5                   10

<210> SEQ ID NO 28
<211> LENGTH: 30
<212> TYPE: PRT
<213> ORGANISM: Artificial Sequence
<220> FEATURE:
<223> OTHER INFORMATION: N-terminal sequences of ATX20514 toxins

<400> SEQUENCE: 28

Ser Thr Ser Arg Gln Asp Val Ala Lys Leu Gly Pro Gly Trp Asn Lys
1               5                   10                  15

Val Leu Leu Asn Tyr Ala Leu Ala Met Gln Ala Leu Asp Glu
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: N-terminal sequences of ATX20514 toxins

<400> SEQUENCE: 29

Ser Thr Ser Gly Gln Asp Val Ala Lys Leu Gly Pro Gln Trp Asn Lys
1               5                   10                  15

Val Leu Leu Asn Tyr Ala Leu Ala Met Gln Ala Leu Asp Glu
            20                  25                  30

<210> SEQ ID NO 30
<211> LENGTH: 4
<212> TYPE: PRT
<213> ORGANISM: Artificial Sequence
<220> FEATURE:
<223> OTHER INFORMATION: targeting peptide

<400> SEQUENCE: 30

Lys Asp Glu Leu
1

<210> SEQ ID NO 31
<211> LENGTH: 685
<212> TYPE: PRT
<213> ORGANISM: Neurospora crassa

<400> SEQUENCE: 31

Met Ser Thr Asp Ile Lys Phe Ala Ile Thr Gly Val Pro Thr Pro Pro
1               5                   10                  15

Ser Ser Asn Gly Ala Val Pro Leu Arg Arg Glu Leu Arg Asp Leu Gln
            20                  25                  30

Gln Asn Tyr Pro Glu Gln Phe Asn Leu Tyr Leu Leu Gly Leu Arg Asp

```
                    35                  40                  45
Phe Gln Gly Leu Asp Glu Ala Lys Leu Asp Ser Tyr Tyr Gln Val Ala
 50                  55                  60

Gly Ile His Gly Met Pro Phe Lys Pro Trp Ala Gly Val Pro Ser Asp
 65                  70                  75                  80

Thr Asp Trp Ser Gln Pro Gly Ser Ser Gly Phe Gly Gly Tyr Cys Thr
                     85                  90                  95

His Ser Ser Ile Leu Phe Ile Thr Trp His Arg Pro Tyr Leu Ala Leu
                    100                 105                 110

Tyr Glu Gln Ala Leu Tyr Ala Ser Val Gln Ala Val Ala Gln Lys Phe
                    115                 120                 125

Pro Val Glu Gly Gly Leu Arg Ala Lys Tyr Val Ala Ala Lys Asp
                    130                 135                 140

Phe Arg Ala Pro Tyr Phe Asp Trp Ala Ser Gln Pro Pro Lys Gly Thr
145                 150                 155                 160

Leu Ala Phe Pro Glu Ser Leu Ser Ser Arg Thr Ile Gln Val Val Asp
                    165                 170                 175

Val Asp Gly Lys Thr Lys Ser Ile Asn Asn Pro Leu His Arg Phe Thr
                    180                 185                 190

Phe His Pro Val Asn Pro Ser Pro Gly Asp Phe Ser Ala Ala Trp Ser
                    195                 200                 205

Arg Tyr Pro Ser Thr Val Arg Tyr Pro Asn Arg Leu Thr Gly Ala Ser
                    210                 215                 220

Arg Asp Glu Arg Ile Ala Pro Ile Leu Ala Asn Glu Leu Ala Ser Leu
225                 230                 235                 240

Arg Asn Asn Val Ser Leu Leu Leu Ser Tyr Lys Asp Phe Asp Ala
                    245                 250                 255

Phe Ser Tyr Asn Arg Trp Asp Pro Asn Thr Asn Pro Gly Asp Phe Gly
                    260                 265                 270

Ser Leu Glu Asp Val His Asn Glu Ile His Asp Arg Thr Gly Gly Asn
                    275                 280                 285

Gly His Met Ser Ser Leu Glu Val Ser Ala Phe Asp Pro Leu Phe Trp
                    290                 295                 300

Leu His His Val Asn Val Asp Arg Leu Trp Ser Ile Trp Gln Asp Leu
305                 310                 315                 320

Asn Pro Asn Ser Phe Met Thr Pro Arg Pro Ala Pro Tyr Ser Thr Phe
                    325                 330                 335

Val Ala Gln Glu Gly Glu Ser Gln Ser Lys Ser Thr Pro Leu Glu Pro
                    340                 345                 350

Phe Trp Asp Lys Ser Ala Ala Asn Phe Trp Thr Ser Glu Gln Val Lys
                    355                 360                 365

Asp Ser Ile Thr Phe Gly Tyr Ala Tyr Pro Glu Thr Gln Lys Trp Lys
                    370                 375                 380

Tyr Ser Ser Val Lys Glu Tyr Gln Ala Ala Ile Arg Lys Ser Val Thr
385                 390                 395                 400

Ala Leu Tyr Gly Ser Asn Val Phe Ala Asn Phe Val Glu Asn Val Ala
                    405                 410                 415

Asp Arg Thr Pro Ala Leu Lys Lys Pro Gln Ala Thr Gly Glu Glu Ser
                    420                 425                 430

Lys Ser Thr Val Ser Ala Ala Ala His Ala Val Glu Leu Ser Gly
                    435                 440                 445

Ala Lys Lys Val Ala Glu Lys Val His Asn Val Phe Gln His Ala Glu
450                 455                 460
```

```
Glu Lys Ala Gln Lys Pro Val Val Pro Val Lys Asp Thr Lys Ala Glu
465                 470                 475                 480

Ser Ser Thr Ala Ala Gly Met Met Ile Gly Leu Ser Ile Lys Arg Pro
                485                 490                 495

Ser Lys Leu Thr Ala Ser Pro Gly Pro Ile Pro Glu Ser Leu Lys Tyr
            500                 505                 510

Leu Ala Pro Asp Gly Lys Tyr Thr Asp Trp Ile Val Asn Val Arg Ala
            515                 520                 525

Gln Lys His Gly Leu Gly Gln Ser Phe Arg Val Ile Val Phe Leu Gly
        530                 535                 540

Glu Phe Asn Pro Asp Pro Glu Thr Trp Asp Asp Glu Phe Asn Cys Val
545                 550                 555                 560

Gly Arg Val Ser Val Leu Gly Arg Ser Ala Glu Thr Gln Cys Gly Lys
                565                 570                 575

Cys Arg Lys Asp Asn Ala Asn Gly Leu Ile Val Ser Gly Thr Val Pro
                580                 585                 590

Leu Thr Ser Ala Leu Leu Gln Asp Ile Val Gly Gly Glu Leu Gln Ser
            595                 600                 605

Leu Lys Pro Glu Asp Val Ile Pro His Leu Arg Ala Asn Leu Lys Trp
610                 615                 620

Lys Val Ala Leu Phe Asn Gly Asp Glu Tyr Asn Leu Glu Val Pro
625                 630                 635                 640

Asp Leu Lys Val Ser Val Ala Ser Thr Glu Val Thr Ile Asp Glu Glu
                645                 650                 655

Gly Leu Pro His Tyr Ser Arg Gln Tyr Thr Val Tyr Pro Glu Ile Thr
                660                 665                 670

Glu Gly Lys Pro Cys Gly His Gly Pro Glu Asp His Ile
            675                 680                 685

<210> SEQ ID NO 32
<211> LENGTH: 579
<212> TYPE: PRT
<213> ORGANISM: Pyrenophora triticirepentis

<400> SEQUENCE: 32

Met Val Asn Asp Thr Gln Ala Phe Gln Gln Gly Ala Leu Ser Asn Ala
1               5                   10                  15

Leu Thr Gly Asn Val Phe Val Arg Arg Glu Val Arg Asp Leu Gln Ala
                20                  25                  30

Asn Phe Pro Asp Gln Trp Thr Leu Tyr Ile Leu Ala Leu Asn Lys Leu
            35                  40                  45

His Asn Ala Asn Gln Ser Asp Ala Tyr Ser Phe Tyr Gly Ile Ala Ser
        50                  55                  60

Ile His Gly Arg Pro Phe Gln Thr Trp Gly Asp Ala Pro Gly Leu Pro
65                  70                  75                  80

Tyr Lys Gln Gly Met Thr Gly Tyr Cys Pro His Gly Asn Glu Leu Phe
                85                  90                  95

Met Gly Trp His Arg Pro Tyr Leu Ala Leu Phe Glu Gln Val Val Ser
            100                 105                 110

Asp Tyr Val His Asp Ile Ala Thr Gln Ala Pro Thr Asp Lys Val Glu
        115                 120                 125

Arg Tyr Leu Ala Ala Ala Asn Glu Phe Arg Ile Pro Tyr Trp Asp Trp
    130                 135                 140

Ala Gln Gly Thr Asn Ser Gly Pro Val Pro Glu Phe Phe Thr Asn Pro
145                 150                 155                 160
```

```
Met Leu Thr Val Thr Asn Thr Asp Gly Val Ser Thr Pro Met Ser Asn
                165                 170                 175

Pro Leu Tyr Ser Tyr Gln Phe Asn Pro Ile Ser Asp Arg Phe Asp Glu
            180                 185                 190

Lys Trp Arg Asn Ile Asn Ala Thr Ile Arg Trp Pro Asn Thr Asp Asp
        195                 200                 205

Ala Thr Ala His Ser Gln Asn Gly Met Phe Ser Asp Ala Phe Ala Gly
        210                 215                 220

Gln Ser Val Asn Ile Val Ala Gln Ile Gly Val Val Phe Arg Ser Ser
225                 230                 235                 240

Thr Phe Ser Arg Phe Ser Thr Thr Leu Glu Asp Pro His Gly Trp Ile
                245                 250                 255

His Gly Ile Ile Gly Gly Gly Tyr Thr Ala Asp Ala Pro Tyr Lys Gly
            260                 265                 270

His Met Trp Pro Leu Glu Tyr Ser Ala Phe Glu Pro Leu Phe Met Leu
        275                 280                 285

His His Ala Asn Val Asp Arg Leu Leu Ala Leu Tyr Gln Ala Ala His
        290                 295                 300

Pro Asp Arg Trp Met Glu Ser Ser Asn Ile Gly Pro His Gly Asn Val
305                 310                 315                 320

Tyr Leu Glu Asp Tyr Gln Glu Val Asn Gly Asp Thr Ser Leu Leu Pro
                325                 330                 335

Phe Arg Lys Thr Pro Gly Glu Phe Trp Thr Pro Asn Ala Cys Arg Asn
            340                 345                 350

Thr Thr Val Leu Gly Tyr Ala Tyr Pro Glu Thr Gln Arg Trp Gln Tyr
        355                 360                 365

Pro Ser Asp Asp Ser Tyr Gln Asn Ala Val Asn Ser Val Ile Ser Thr
        370                 375                 380

Leu Tyr Gly Gly Gln Thr Arg Ser Gln Leu Thr Ser Ala Ile Glu Thr
385                 390                 395                 400

Gly Ser Gly Glu Arg Leu Leu Lys Asn Gly Asn Ser Phe Thr Asp Trp
                405                 410                 415

Thr Ile Asn Thr Gln Ala Ile Ala Ser Lys Leu Pro Ser Thr Phe Ile
            420                 425                 430

Val Lys Phe Ser Phe Val Gly Ile Phe Gln Ser Asp Pro Ser Val Asp
        435                 440                 445

Ala Gly Ser Trp Met Met Leu Met Pro Asp Asn Lys Gln Asn Met His
        450                 455                 460

Thr Leu Gln Val Arg Thr Glu Ser Glu Lys Val Leu Tyr Gly Thr Thr
465                 470                 475                 480

Ser Ile Thr Ala His Leu Ile Asp Leu Val Asn Ala Gly Lys Leu Asn
                485                 490                 495

Ser Ile Ser Ser Asp Asp Val Val Pro Tyr Leu Arg Asp Thr Leu Thr
            500                 505                 510

Trp Asn Ile Phe Thr Asp Asn Gly Thr Arg Ile Ala Gln Pro Asn Gly
        515                 520                 525

Ala Leu Thr Val Gln Val Thr Ser Thr Glu Ala Tyr Val Pro Glu Asp
        530                 535                 540

Arg Ser Ala Pro Ile Gln Tyr Ser Glu Asn Ile Thr Glu His Pro Glu
545                 550                 555                 560

Ile Thr Ala Asn Lys Phe Gly Gly Thr Ser Ser Thr Ser Pro Ala Met
                565                 570                 575

Met Phe Leu
```

<210> SEQ ID NO 33
<211> LENGTH: 574
<212> TYPE: PRT
<213> ORGANISM: Podospora anserina

<400> SEQUENCE: 33

```
Met Ser Thr Thr Gly Asn Ile Ala Ile Thr Gly Ile Pro Thr Thr Ala
 1               5                  10                  15

Gly Pro Asp Gly Ser Phe Pro Leu Arg Arg Glu Leu Arg Asp Leu Gln
                20                  25                  30

Arg Asn Tyr Pro Asp His Phe Asn Leu Leu Val Leu Ala Leu Lys Asp
            35                  40                  45

Phe Gln Ala Leu Asn Glu Ser Val Gln Thr Ser Tyr Tyr Gln Ile Ala
    50                  55                  60

Gly Ile His Gly Leu Pro Tyr Lys Pro Trp Asn Asn Val Gly Ser Asn
65                  70                  75                  80

Ser Asp Trp Gln Ser Thr Ser Gly Phe Gly Gly Tyr Cys Thr His Ser
                85                  90                  95

Ser Ile Leu Phe Leu Thr Trp His Arg Pro Tyr Leu Ala Leu Phe Glu
            100                 105                 110

Gln Ala Leu Tyr Asn Ser Ile Gln Lys Ile Ala Asn Gln Phe Pro Gln
        115                 120                 125

Gly Pro Leu Arg Thr Lys Tyr Val Glu Ala Ala Lys Thr Phe Arg Met
    130                 135                 140

Pro Tyr Phe Asp Trp Ala Ser Gln Pro Pro Ser Gly Ser Ser Ala Phe
145                 150                 155                 160

Pro Ser Ala Phe Thr Ala Pro Ser Leu Gln Val Val Asp Val Asp Gly
                165                 170                 175

Lys Thr Lys Ser Thr Ala Asn Pro Ile Tyr Arg Phe Val Phe His Pro
            180                 185                 190

Val Asn Pro Ser Pro Gly Asp Phe Pro Arg Gln Trp Ser Arg Phe Pro
        195                 200                 205

Thr Thr Val Arg Tyr Pro Asn Pro Arg Thr Gly Gln Ser Gln Asp Asn
    210                 215                 220

Arg Val Ala Pro Ile Leu Ala Asn Glu Leu Ala Ser Leu Arg Thr Asn
225                 230                 235                 240

Val Ser Leu Leu Leu Leu Ser Tyr Thr Asn Phe Asp Ala Phe Ser Phe
                245                 250                 255

Asn Arg Trp Asp Pro Asn Met Thr Pro Gly Glu Phe Gly Ser Leu Glu
            260                 265                 270

Asp Val His Asn Glu Ile His Asp Arg Thr Gly Gly Gly His Met
        275                 280                 285

Ser Ser Leu Asp Val Ser Ser Phe Asp Pro Leu Phe Trp Phe His His
    290                 295                 300

Thr Asn Val Asp Arg Leu Trp Ala Ile Trp Gln Asp Leu Asn Pro Asp
305                 310                 315                 320

Asn Phe Leu Thr Pro Arg Pro Ala Pro Tyr Ser Thr Phe Asn Ser Thr
                325                 330                 335

Glu Gly Glu Ser Gln Thr Lys Asp Thr Pro Leu Thr Pro Phe Trp Asp
            340                 345                 350

Lys Ser Ala Thr Lys Phe Trp Thr Ser Glu Ile Lys Asp Thr Thr
        355                 360                 365

Thr Thr Phe Gly Tyr Ala Tyr Pro Glu Thr Gln Glu Trp Lys Tyr Arg
    370                 375                 380
```

```
Thr Gly Ser Glu Tyr Gln Thr Ser Ile Arg Gln Ala Val Thr Thr Leu
385                 390                 395                 400

Tyr Gly Thr Asn Val Phe Ala Asn Phe Ala Ala Asn Val Gln Ala
            405                 410                 415

Arg Ala Thr Glu His Thr Glu Leu Ile Lys Ser Leu Ser Leu Ala Ala
            420                 425                 430

Pro Pro Pro Ser Ala Pro Ile Thr Ala Glu Lys Pro Leu Leu Ile Thr
            435                 440                 445

Gln Glu Met Lys Ala Ser Pro Ile Pro Glu His Leu Gln His Leu Ala
            450                 455                 460

Pro Asn Asn Lys Tyr Pro Glu Trp Val Val Asn Ile Arg Ala Gln Lys
465                 470                 475                 480

His Gly Leu His Gly Ala Phe Arg Val Ile Val Phe Leu Gly Pro Ile
                485                 490                 495

Asp Glu Ser Asp Pro Asp Ser Trp Gln Thr Glu Phe Asn Thr Val Gly
                500                 505                 510

Arg Val Ser Val Leu Gly Arg Ser Thr Gln Gly Pro Thr Thr Thr Lys
            515                 520                 525

Cys Ala Lys Cys Ile Thr Asp Ala Ala Asp Glu Leu Met Ile Ser Gly
            530                 535                 540

Thr Val Pro Leu Thr Ser Ala Leu Leu Gln Asp Ile Val Asn Glu Asn
545                 550                 555                 560

Thr Ala Ser Ile Ala Cys Ser Gln Arg Lys Trp Cys Arg Ile
                565                 570

<210> SEQ ID NO 34
<211> LENGTH: 618
<212> TYPE: PRT
<213> ORGANISM: Lentinula elodes

<400> SEQUENCE: 34

Met Ser His Tyr Leu Val Thr Gly Ala Thr Gly Gly Ser Thr Ser Gly
1               5                   10                  15

Ala Ala Ala Pro Asn Arg Leu Glu Ile Asn Asp Phe Val Lys Gln Glu
                20                  25                  30

Asp Gln Phe Ser Leu Tyr Ile Gln Ala Leu Gln Tyr Ile Tyr Ser Ser
            35                  40                  45

Lys Ser Gln Asp Asp Ile Asp Ser Phe Phe Gln Ile Gly Gly Ile His
50                  55                  60

Gly Leu Pro Tyr Val Pro Trp Asp Gly Ala Gly Asn Lys Pro Val Asp
65                  70                  75                  80

Thr Asp Ala Trp Glu Gly Tyr Cys Thr His Gly Ser Val Leu Phe Pro
                85                  90                  95

Thr Phe His Arg Pro Tyr Val Leu Leu Ile Glu Gln Ala Ile Gln Ala
            100                 105                 110

Ala Ala Val Asp Ile Ala Ala Thr Tyr Ile Val Asp Arg Ala Arg Tyr
            115                 120                 125

Gln Asp Ala Ala Leu Asn Leu Arg Gln Pro Tyr Trp Asp Trp Ala Arg
            130                 135                 140

Asn Pro Val Pro Pro Glu Val Ile Ser Leu Asp Glu Val Thr Ile
145                 150                 155                 160

Val Asn Pro Ser Gly Glu Lys Ile Ser Val Pro Asn Pro Leu Arg Arg
                165                 170                 175

Tyr Thr Phe His Pro Ile Asp Pro Ser Phe Pro Glu Pro Tyr Gln Ser
            180                 185                 190
```

-continued

```
Trp Ser Thr Thr Leu Arg His Pro Leu Ser Asp Asp Ala Asn Ala Ser
        195                 200                 205

Asp Asn Val Pro Glu Leu Lys Ala Thr Leu Arg Ser Ala Gly Pro Gln
210                 215                 220

Leu Lys Thr Lys Thr Tyr Asn Leu Leu Thr Arg Val His Thr Trp Pro
225                 230                 235                 240

Ala Phe Ser Asn His Thr Pro Asp Asp Gly Gly Ser Thr Ser Asn Ser
                245                 250                 255

Leu Glu Gly Ile His Asp Ser Val His Val Asp Val Gly Gly Asn Gly
                260                 265                 270

Gln Met Ser Asp Pro Ser Val Ala Gly Phe Asp Pro Ile Phe Met
        275                 280                 285

His His Ala Gln Val Asp Arg Leu Leu Ser Leu Trp Ser Ala Leu Asn
        290                 295                 300

Pro Arg Val Trp Ile Thr Asp Gly Pro Ser Gly Asp Gly Thr Trp Thr
305                 310                 315                 320

Ile Pro Pro Asp Thr Val Val Gly Lys Asp Thr Asp Leu Thr Pro Phe
                325                 330                 335

Trp Asn Thr Gln Ser Ser Tyr Trp Ile Ser Ala Asn Val Thr Asp Thr
                340                 345                 350

Ser Lys Met Gly Tyr Thr Tyr Pro Glu Phe Asn Asn Leu Asp Met Gly
        355                 360                 365

Asn Glu Val Ala Val Arg Ser Ala Ile Ala Gln Val Asn Lys Leu
370                 375                 380

Tyr Gly Gly Pro Phe Thr Lys Phe Ala Ala Ile Gln Gln Pro Ser
385                 390                 395                 400

Ser Gln Thr Thr Ala Asp Ala Ser Thr Ile Gly Asn Val Thr Ser Asp
                405                 410                 415

Ala Ser Ser His Leu Val Asp Ser Lys Ile Asn Pro Thr Pro Asn Arg
                420                 425                 430

Ser Ile Asp Asp Ala Pro Gln Val Lys Ile Ala Ser Thr Leu Arg Asn
        435                 440                 445

Asn Glu Gln Lys Glu Phe Trp Glu Trp Thr Ala Arg Val Gln Val Lys
        450                 455                 460

Lys Tyr Glu Ile Gly Gly Ser Phe Lys Val Leu Phe Phe Leu Gly Ser
465                 470                 475                 480

Val Pro Ser Asp Pro Lys Glu Trp Ala Thr Asp Pro His Phe Val Gly
                485                 490                 495

Ala Phe His Gly Phe Val Asn Ser Ser Ala Glu Arg Cys Ala Asn Cys
                500                 505                 510

Arg Arg Gln Gln Asp Val Val Leu Glu Gly Phe Val His Leu Asn Glu
        515                 520                 525

Gly Ile Ala Asn Ile Ser Asn Leu Asn Ser Phe Asp Pro Ile Val Val
        530                 535                 540

Glu Pro Tyr Leu Lys Glu Asn Leu His Trp Arg Val Gln Lys Val Ser
545                 550                 555                 560

Gly Glu Val Val Asn Leu Asp Ala Ala Thr Ser Leu Glu Val Val
                565                 570                 575

Val Ala Thr Arg Leu Glu Leu Pro Pro Gly Glu Ile Phe Pro Val Pro
                580                 585                 590

Ala Glu Thr His His His His His Ile Thr His Gly Arg Pro Gly Gly
        595                 600                 605

Ser Arg His Ser Val Ala Ser Ser Ser
610                 615
```

<210> SEQ ID NO 35
<211> LENGTH: 618
<212> TYPE: PRT
<213> ORGANISM: Pycnoporus sanguineus

<400> SEQUENCE: 35

| | | | | | | | | | | | | | | |
|---|---|---|---|---|---|---|---|---|---|---|---|---|---|---|
| Met | Ser | His | Phe | Ile | Val | Thr | Gly | Pro | Val | Gly | Gly | Gln | Thr | Glu | Gly |
| 1 | | | | 5 | | | | | 10 | | | | | 15 | |
| Ala | Pro | Ala | Pro | Asn | Arg | Leu | Glu | Ile | Asn | Asp | Phe | Val | Lys | Asn | Glu |
| | | | 20 | | | | | 25 | | | | | 30 | | |
| Glu | Phe | Phe | Ser | Leu | Tyr | Val | Gln | Ala | Leu | Asp | Ile | Met | Tyr | Gly | Leu |
| | | | 35 | | | | | 40 | | | | | 45 | | |
| Lys | Gln | Glu | Glu | Leu | Ile | Ser | Phe | Phe | Gln | Ile | Gly | Gly | Ile | His | Gly |
| 50 | | | | | 55 | | | | | 60 | | | | | |
| Leu | Pro | Tyr | Val | Ala | Trp | Ser | Asp | Ala | Gly | Ala | Asp | Asp | Pro | Ala | Glu |
| 65 | | | | | 70 | | | | | 75 | | | | | 80 |
| Pro | Ser | Gly | Tyr | Cys | Thr | His | Gly | Ser | Val | Leu | Phe | Pro | Thr | Trp | His |
| | | | | 85 | | | | | 90 | | | | | 95 | |
| Arg | Pro | Tyr | Val | Ala | Leu | Tyr | Glu | Gln | Ile | Leu | His | Lys | Tyr | Ala | Gly |
| | | | | 100 | | | | | 105 | | | | | 110 | |
| Glu | Ile | Ala | Asp | Lys | Tyr | Thr | Val | Asp | Lys | Pro | Arg | Trp | Gln | Lys | Ala |
| | | | | 115 | | | | | 120 | | | | | 125 | |
| Ala | Ala | Asp | Leu | Arg | Gln | Pro | Phe | Trp | Asp | Trp | Ala | Lys | Asn | Thr | Leu |
| | 130 | | | | | 135 | | | | | 140 | | | | |
| Pro | Pro | Pro | Glu | Val | Ile | Ser | Leu | Asp | Lys | Val | Thr | Ile | Thr | Thr | Pro |
| 145 | | | | | 150 | | | | | 155 | | | | | 160 |
| Asp | Gly | Gln | Arg | Thr | Gln | Val | Asp | Asn | Pro | Leu | Arg | Arg | Tyr | Arg | Phe |
| | | | | 165 | | | | | 170 | | | | | 175 | |
| His | Pro | Ile | Asp | Pro | Ser | Phe | Pro | Glu | Pro | Tyr | Ser | Asn | Trp | Pro | Ala |
| | | | | 180 | | | | | 185 | | | | | 190 | |
| Thr | Leu | Arg | His | Pro | Thr | Ser | Asp | Gly | Ser | Asp | Ala | Lys | Asp | Asn | Val |
| | | | | 195 | | | | | 200 | | | | | 205 | |
| Lys | Asp | Leu | Thr | Thr | Thr | Leu | Lys | Ala | Asp | Gln | Pro | Asp | Ile | Thr | Thr |
| 210 | | | | | 215 | | | | | 220 | | | | | |
| Lys | Thr | Tyr | Asn | Leu | Leu | Thr | Arg | Val | His | Thr | Trp | Pro | Ala | Phe | Ser |
| 225 | | | | | 230 | | | | | 235 | | | | | 240 |
| Asn | His | Thr | Pro | Gly | Asp | Gly | Ser | Ser | Ser | Asn | Ser | Leu | Glu | Ala |
| | | | | 245 | | | | | 250 | | | | | 255 | |
| Ile | His | Asp | His | Ile | His | Asp | Ser | Val | Gly | Gly | Gly | Gln | Met | Gly |
| | | | | 260 | | | | | 265 | | | | | 270 | |
| Asp | Pro | Ser | Val | Ala | Gly | Phe | Asp | Pro | Ile | Phe | Phe | Leu | His | His | Cys |
| | | | | 275 | | | | | 280 | | | | | 285 | |
| Gln | Val | Asp | Arg | Leu | Leu | Ala | Leu | Trp | Ser | Ala | Leu | Asn | Pro | Gly | Val |
| | 290 | | | | | 295 | | | | | 300 | | | | |
| Trp | Val | Asn | Ser | Ser | Ser | Ser | Glu | Asp | Gly | Thr | Tyr | Thr | Ile | Pro | Pro |
| 305 | | | | | 310 | | | | | 315 | | | | | 320 |
| Asp | Ser | Thr | Val | Asp | Gln | Thr | Thr | Ala | Leu | Thr | Pro | Phe | Trp | Asp | Thr |
| | | | | 325 | | | | | 330 | | | | | 335 | |
| Gln | Ser | Thr | Phe | Trp | Thr | Ser | Phe | Gln | Ser | Ala | Gly | Val | Ser | Pro | Ser |
| | | | | 340 | | | | | 345 | | | | | 350 | |
| Gln | Phe | Gly | Tyr | Ser | Tyr | Pro | Glu | Phe | Asn | Gly | Leu | Asn | Leu | Gln | Asp |
| | | | | 355 | | | | | 360 | | | | | 365 | |
| Gln | Lys | Ala | Val | Lys | Asp | His | Ile | Ala | Glu | Val | Val | Asn | Glu | Leu | Tyr |
| | 370 | | | | | 375 | | | | | 380 | | | | |

```
Gly His Arg Met Arg Lys Thr Phe Pro Phe Pro Gln Leu Gln Ala Val
385                 390                 395                 400

Ser Val Ala Lys Gln Gly Asp Ala Val Thr Pro Ser Val Ala Thr Asp
            405                 410                 415

Ser Val Ser Ser Thr Thr Pro Ala Glu Asn Pro Ala Ser Arg Glu
        420                 425                 430

Asp Ala Ser Asp Lys Asp Thr Glu Pro Thr Leu Asn Val Glu Val Ala
        435                 440                 445

Ala Pro Gly Ala His Leu Thr Ser Thr Lys Tyr Trp Asp Trp Thr Ala
    450                 455                 460

Arg Ile His Val Lys Lys Tyr Glu Val Gly Ser Phe Ser Val Leu
465                 470                 475                 480

Leu Phe Leu Gly Ala Ile Pro Glu Asn Pro Ala Asp Trp Arg Thr Ser
                485                 490                 495

Pro Asn Tyr Val Gly Gly His His Ala Phe Val Asn Ser Ser Pro Gln
                500                 505                 510

Arg Cys Ala Asn Cys Arg Gly Gln Gly Asp Leu Val Ile Glu Gly Phe
                515                 520                 525

Val His Leu Asn Glu Ala Ile Ala Arg His Ala His Leu Asp Ser Phe
                530                 535                 540

Asp Pro Thr Val Val Arg Pro Tyr Leu Thr Arg Glu Leu His Trp Gly
545                 550                 555                 560

Val Met Lys Val Asn Gly Thr Val Pro Leu Gln Asp Val Pro Ser
                565                 570                 575

Leu Glu Val Val Val Leu Ser Thr Pro Leu Thr Leu Pro Pro Gly Glu
            580                 585                 590

Pro Phe Pro Val Pro Gly Thr Pro Val Asn His His Asp Ile Thr His
            595                 600                 605

Gly Arg Pro Gly Gly Ser His His Thr His
    610                 615
```

<210> SEQ ID NO 36
<211> LENGTH: 625
<212> TYPE: PRT
<213> ORGANISM: Pholio nameka

<400> SEQUENCE: 36

```
Met Ser Arg Val Val Ile Thr Gly Val Ser Gly Thr Val Ala Asn Arg
1               5                   10                  15

Leu Glu Ile Asn Asp Phe Val Lys Asn Asp Lys Phe Phe Ser Leu Tyr
            20                  25                  30

Ile Gln Ala Leu Gln Val Met Ser Ser Val Pro Pro Gln Glu Asn Val
        35                  40                  45

Arg Ser Phe Phe Gln Ile Gly Gly Ile His Gly Leu Pro Tyr Thr Pro
    50                  55                  60

Trp Asp Gly Ile Thr Gly Asp Gln Pro Phe Asp Pro Asn Thr Gln Trp
65              70                  75                  80

Gly Gly Tyr Cys Thr His Gly Ser Val Leu Phe Pro Thr Trp His Arg
                85                  90                  95

Pro Tyr Val Leu Leu Tyr Glu Gln Ile Leu His Lys His Val Gln Asp
                100                 105                 110

Ile Ala Ala Thr Tyr Thr Thr Ser Asp Lys Ala Ala Trp Val Gln Ala
            115                 120                 125

Ala Ala Asn Leu Arg Gln Pro Tyr Trp Asp Trp Ala Ala Asn Ala Val
        130                 135                 140
```

```
Pro Pro Asp Gln Val Ile Ala Ser Lys Lys Val Thr Ile Thr Gly Ser
145                 150                 155                 160

Asn Gly His Lys Val Glu Val Asp Asn Pro Leu Tyr His Tyr Lys Phe
            165                 170                 175

His Pro Ile Asp Ser Ser Phe Pro Arg Pro Tyr Ser Glu Trp Pro Thr
            180                 185                 190

Thr Leu Arg Gln Pro Asn Ser Ser Arg Pro Asn Ala Thr Asp Asn Val
            195                 200                 205

Ala Lys Leu Arg Asn Val Leu Arg Ala Ser Gln Glu Asn Ile Thr Ser
210                 215                 220

Asn Thr Tyr Ser Met Leu Thr Arg Val His Thr Trp Lys Ala Phe Ser
225                 230                 235                 240

Asn His Thr Val Gly Asp Gly Ser Thr Ser Asn Ser Leu Glu Ala
            245                 250                 255

Ile His Asp Gly Ile His Val Asp Val Gly Gly Gly His Met Ala
            260                 265                 270

Asp Pro Ala Val Ala Ala Phe Asp Pro Ile Phe Phe Leu His His Cys
            275                 280                 285

Asn Val Asp Arg Leu Leu Ser Leu Trp Ala Ala Ile Asn Pro Gly Val
290                 295                 300

Trp Val Ser Pro Gly Asp Ser Glu Asp Gly Thr Phe Ile Leu Pro Pro
305                 310                 315                 320

Glu Ala Pro Val Asp Val Ser Thr Pro Leu Thr Pro Phe Ser Asn Thr
            325                 330                 335

Glu Thr Thr Phe Trp Ala Ser Gly Gly Ile Thr Asp Thr Thr Lys Leu
            340                 345                 350

Gly Tyr Thr Tyr Pro Glu Phe Asn Gly Leu Asp Leu Gly Asn Ala Gln
            355                 360                 365

Ala Val Lys Ala Ala Ile Gly Asn Ile Val Asn Arg Leu Tyr Gly Ala
370                 375                 380

Ser Val Phe Ser Gly Phe Ala Ala Ala Thr Ser Ala Ile Gly Ala Gly
385                 390                 395                 400

Ser Val Ala Ser Leu Ala Ala Asp Val Pro Leu Glu Lys Ala Pro Ala
            405                 410                 415

Pro Ala Pro Glu Ala Ala Gln Ser Pro Val Pro Ala Pro Ala His
            420                 425                 430

Val Glu Pro Ala Val Arg Ala Val Ser Val His Ala Ala Ala Gln
            435                 440                 445

Pro His Ala Glu Pro Pro Val His Val Ser Ala Gly Gly His Pro Ser
450                 455                 460

Pro His Gly Phe Tyr Asp Trp Thr Ala Arg Ile Glu Phe Lys Lys Tyr
465                 470                 475                 480

Glu Phe Gly Ser Ser Phe Ser Val Leu Leu Phe Leu Gly Pro Val Pro
            485                 490                 495

Glu Asp Pro Glu Gln Trp Leu Val Ser Pro Asn Phe Val Gly Ala His
            500                 505                 510

His Ala Phe Val Asn Ser Ala Ala Gly His Cys Ala Asn Cys Arg Asn
            515                 520                 525

Gln Gly Asn Val Val Glu Gly Phe Val His Leu Thr Lys Tyr Ile
            530                 535                 540

Ser Glu His Ala Gly Leu Arg Ser Leu Asn Pro Glu Val Val Glu Pro
545                 550                 555                 560

Tyr Leu Thr Asn Glu Leu His Trp Arg Val Leu Lys Ala Asp Gly Ser
```

```
                    565                 570                 575
Val Gly Gln Leu Glu Ser Leu Glu Val Ser Val Tyr Gly Thr Pro Met
                580                 585                 590

Asn Leu Pro Val Gly Ala Met Phe Pro Val Pro Gly Asn Arg Arg His
            595                 600                 605

Phe His Gly Ile Thr His Gly Arg Val Gly Gly Ser Arg His Ala Ile
        610                 615                 620

Val
625

<210> SEQ ID NO 37
<211> LENGTH: 630
<212> TYPE: PRT
<213> ORGANISM: Tuber melanosporum

<400> SEQUENCE: 37

Met Thr Met Lys Thr Tyr Pro Ile Thr Gly Val Ala Ser Gln Ala Pro
1               5                   10                  15

Arg Pro Arg Arg Asn Ile Asn Asp Phe Ala Gln Asp Pro Leu Gln Trp
            20                  25                  30

Asn Leu Phe Leu Gln Ala Leu Ile Asn Leu Gln Ser Gln Gly Glu Asp
        35                  40                  45

Thr His Ser Pro Leu Gly Tyr Tyr Gln Val Ala Gly Val His Gly Thr
    50                  55                  60

Pro Tyr Ile Pro Trp Met Glu Lys Ala Asp Ala Asp Arg Ala Gly
65                  70                  75                  80

Asp Tyr Cys Thr His Gly Thr Ala Leu Phe Ile Thr Trp His Arg Pro
                85                  90                  95

Tyr Leu Leu Leu Phe Glu Gln Arg Ile Val Glu Ala Leu Thr Ile
            100                 105                 110

Ala Arg Asn Phe Ser Asp Lys Tyr Arg Ala Glu Tyr Glu Glu Ala Ala
        115                 120                 125

Leu Asn Ile Arg Ile Pro Tyr Trp Asp Trp Ala Thr Asp Ser Asp Val
    130                 135                 140

Pro Gln Ser Ile Arg Phe Ala Glu Thr Asp Ile Thr Leu Pro Glu Val
145                 150                 155                 160

Gly Ser Asp Ala Pro Pro Val Thr Arg Lys Gly Val Pro Asn Pro Met
                165                 170                 175

Tyr Ser Tyr Lys Phe Lys Thr Ser Ile Arg Arg Gln Arg Asp Phe Ser
            180                 185                 190

Ile Val Gly Val Gln Glu Met Val Ala Trp Glu Glu Thr Lys Arg Cys
        195                 200                 205

Pro Asp Glu Lys Gly Ile Ser His Pro Glu Ile Val Arg Gln Leu
    210                 215                 220

Arg Ile Pro Thr Val Asn Pro Thr Ala Gly Ser Ser Phe Arg Asp Pro
225                 230                 235                 240

Ile Tyr Lys Leu Leu Thr Leu Val Gly Ser Tyr Gly Ala Phe Gly Asn
                245                 250                 255

Thr Gly Trp Gln Thr Gly Arg Pro Gly Pro Asn Asn Ile Ser Leu Glu
            260                 265                 270

His Tyr His Asn Ile Ile His Thr Phe Thr Gly Thr Asn Tyr Ile Glu
        275                 280                 285

Glu Asn Ser Lys Glu Gly His Met Ser Glu Val Gly Val Ser Ala Phe
    290                 295                 300

Asp Pro Ile Phe Trp Leu His His Cys Asn Val Asp Arg Leu Tyr Ala
```

```
                305                 310                 315                 320
Ile Trp Gln Ala Ile His Tyr Glu Ala Pro Phe Glu Asp Gln Ala Thr
                325                 330                 335

Asp Tyr Thr Arg Met Pro Leu Thr Lys Ala Ile Asp Asp Ala Glu Thr
                340                 345                 350

Thr Leu Arg Pro Phe Tyr Lys Asp Glu Cys Tyr Asp Val Pro Trp Thr
                355                 360                 365

Ser Ser Met Val Gln Lys Ser Ser Ala Ala Thr Gly Pro Thr Val Phe
                370                 375                 380

Asp Tyr Asn Tyr His Tyr Pro Glu Leu Pro Val Asp Leu Ser Gly Pro
385                 390                 395                 400

Gly Lys Gln Lys Glu Met Ala Ser His Val Leu Arg Arg Val His Gln
                405                 410                 415

Leu Tyr Gly Pro Pro Thr Asp Glu Ser Leu Val Asp Thr Pro Lys Val
                420                 425                 430

Pro Asn Ala Leu Leu Pro Pro Ser Arg Ile Val Arg Asp Gly Met Phe
                435                 440                 445

Arg Arg Glu Trp Leu Ile Phe Leu Arg Val Arg Lys Tyr Leu Ile Pro
                450                 455                 460

Gly Asn Phe Ile Ile Phe Phe Phe Leu Gly Glu Pro Gly Asp Asp Pro
465                 470                 475                 480

Arg Gln Trp Leu Leu Ser Glu Asn His Val Gly Ala Val Asn Thr Phe
                485                 490                 495

Lys Ser Ser Thr Asp Ile Cys Gly Asn Cys Ala Gly Gln Gly Ala Ala
                500                 505                 510

Asp Gln Leu Phe Ser Gly Gly Val Asp Ile Thr Asn Ala Leu Tyr Asn
                515                 520                 525

Lys Leu Ala Asn Ile Gly Leu Thr Leu Asp Asp Gln Asp Glu Ile Glu
                530                 535                 540

Glu Trp Leu Ala Lys Asn Leu Lys Trp Arg Ile Leu Lys Gln Asn Asp
545                 550                 555                 560

Lys Thr Glu Leu Thr Ser His Glu Ile Leu Glu Asn Pro Asp Ser Leu
                565                 570                 575

Phe Ile Gly Val Lys Ser Phe Val Leu Leu Tyr Pro Thr Ser Arg Leu
                580                 585                 590

Pro Ile Asp Gly Gly Glu Phe Leu Ser Ala Pro Lys Ile Ile Asn Glu
                595                 600                 605

Lys Ile His Phe Gly Ala Thr Glu Pro His Lys Asn Arg Gly Gly Leu
                610                 615                 620

Gly Ala Gln Asp Pro Tyr
625                 630

<210> SEQ ID NO 38
<211> LENGTH: 616
<212> TYPE: PRT
<213> ORGANISM: Aspergillus fumigatus

<400> SEQUENCE: 38

Met Ser Ser Asn Lys Pro Tyr Val Ile Lys Gly Ile Pro Val Asp Ala
1               5                   10                  15

Gly Gln Ile Ile Pro Val Arg Arg Asp Ile Asp Glu Trp Tyr Glu Asp
                20                  25                  30

Thr Ser Arg Gln Ser Arg Ile Gln Leu Ser Ile Phe Ile Trp Ala Leu
                35                  40                  45

Arg Glu Phe Gln Ser Ile Asp Tyr Lys Asp Arg Leu Ser Tyr Phe Gln
```

```
                50                  55                  60
Ile Ala Gly Ile His His Phe Pro Leu Ile Thr Trp Asp Glu Glu
 65                  70                  75                  80

Pro Pro Val Pro Asn Lys Pro Gly Tyr Cys Val His Asn Asn Val Thr
                     85                  90                  95

Phe Pro Thr Trp His Arg Pro Tyr Met Leu Leu Phe Glu Gln Arg Leu
                    100                 105                 110

Phe Glu Ile Met Glu Thr Thr Ile Lys Glu Thr Val Pro Glu Ser His
                    115                 120                 125

Lys Gln Glu Trp Arg Asp Ala Ala Arg Gln Trp Arg Leu Pro Tyr Trp
130                 135                 140

Asp Phe Ala Lys Thr Ser Gly Pro His Ala Thr Gly Pro Leu Ser Leu
145                 150                 155                 160

Pro Val Leu Cys Gly Leu Ala Asn Val Val Ile Leu Asn Pro Ala Asn
                    165                 170                 175

Pro Glu Thr Pro Ile Glu Leu Pro Asn Pro Val Tyr Lys Tyr Arg Ala
                    180                 185                 190

Pro Asp Leu Met Gly Asn Leu Asp Lys Pro Phe His Ile Pro Pro Glu
                    195                 200                 205

Arg Ile Asp Pro Asp Lys Asp Tyr Tyr Pro Trp Asp Lys Cys Gln
210                 215                 220

Ala Thr Thr Lys Tyr Gly Leu Leu Lys Asn Asn Pro His Ile Gln Asp
225                 230                 235                 240

Ala Gly Gln Asp Val Thr Lys Ser Asn Leu Ala Leu Asn Glu His Pro
                    245                 250                 255

Trp Tyr Arg Pro Asn Lys Ala Gly Phe Pro Pro Leu Gln Thr Leu Thr
                    260                 265                 270

Tyr Glu Val His Arg Leu Leu Ser Phe Lys Phe Ser Ser Trp Gly Ala
                    275                 280                 285

Phe Ala Ser Thr Lys Trp Cys Asn Glu Glu Asn Lys Pro Pro Ala Ser
                    290                 295                 300

Gln Gln Thr Arg Asp Ile Leu Ser Leu Glu Tyr Ile His Asn Asn Val
305                 310                 315                 320

His Pro Asp Leu Gln Gly Ala Gly His Met Ser Ser Val Pro Val Ala
                    325                 330                 335

Ala Phe Asp Pro Ile Phe Trp Leu Tyr His Asn Asn Val Asp Arg Leu
                    340                 345                 350

Thr Ala Ile Trp Gln Val Leu Asn Gln Asp His Trp Phe Asp Glu Pro
                    355                 360                 365

His Pro Ser Asp Ala Lys Pro Asp Pro Leu Lys Pro Phe His Val
370                 375                 380

Ser Lys Asp Lys Tyr Phe Thr Ser Asp Asp Ala Arg Phe Trp Arg Lys
385                 390                 395                 400

Tyr Gly Tyr Asp Tyr Asp Ile Val Lys Lys Pro Gly Thr Asn Glu Asp
                    405                 410                 415

Arg Ala Pro Glu Glu Val Lys Met Lys Ile Asn Gln Leu Tyr Gly Glu
                    420                 425                 430

Pro Ile Ser Arg Leu His Glu Gly Gln Pro Val Glu Tyr Asp Tyr Val
                    435                 440                 445

Ile Asn Val Ile Tyr Asp Arg Tyr Ala Leu Asp Gly Ile Pro Tyr Thr
            450                 455                 460

Ile Val Phe Tyr Leu His Leu Lys Asp Gly Ser Tyr Lys Cys Leu Gly
465                 470                 475                 480
```

```
Gly Val Tyr Thr Phe Ser Thr Lys Leu Ser Asp Ala Gln Asp Thr Glu
            485                 490                 495

Arg Gly Gly Cys Asp Asn Cys Arg Glu Gln Lys Lys Ala Gly Val Leu
            500                 505                 510

Ala Ser Ala Gln Ile Pro Leu Thr Tyr Thr Leu Tyr Glu Arg Gln Glu
            515                 520                 525

Trp His Asn Leu Gly Lys Leu Leu Pro Val Lys Glu Thr Ala Asp Ile
            530                 535                 540

Ile Arg Gln His Leu Cys Trp Lys Val Val Gly Val Asn Asn Ser Ile
545                 550                 555                 560

Leu Phe Asp Ser Glu Gln Pro Met Arg Gly Asp Pro Ala Thr Trp Arg
            565                 570                 575

Ser Leu Asp Val Thr Ala Ala Tyr Ser Glu Ile His Tyr Pro Val Asp
            580                 585                 590

Arg Asn Tyr Lys Tyr Ile Asp Arg Gly Leu Pro Ala Tyr His Asn Tyr
            595                 600                 605

Leu Pro Ile His Leu Ser Pro Thr
            610                 615

<210> SEQ ID NO 39
<211> LENGTH: 556
<212> TYPE: PRT
<213> ORGANISM: Agaricus bisporus

<400> SEQUENCE: 39

Met Ser Leu Ile Ala Thr Val Gly Pro Thr Gly Gly Val Lys Asn Arg
1               5                   10                  15

Leu Asn Ile Val Asp Phe Val Lys Asn Glu Lys Phe Phe Thr Leu Tyr
            20                  25                  30

Val Arg Ser Leu Glu Leu Leu Gln Ala Lys Glu Gln His Asp Tyr Ser
        35                  40                  45

Ser Phe Phe Gln Leu Ala Gly Ile His Gly Leu Pro Thr Glu Trp
    50                  55                  60

Ala Lys Glu Arg Pro Ser Met Asn Leu Tyr Lys Ala Gly Tyr Cys Thr
65              70                  75                  80

His Gly Gln Val Leu Phe Pro Thr Trp His Arg Thr Tyr Leu Ser Val
            85                  90                  95

Leu Glu Gln Ile Leu Gln Gly Ala Ala Ile Glu Val Ala Lys Lys Phe
            100                 105                 110

Thr Ser Asn Gln Thr Asp Trp Val Gln Ala Ala Gln Asp Leu Arg Gln
            115                 120                 125

Pro Tyr Trp Asp Trp Gly Phe Glu Leu Met Pro Pro Asp Glu Val Ile
            130                 135                 140

Lys Asn Glu Glu Val Asn Ile Thr Asn Tyr Asp Gly Lys Lys Ile Ser
145                 150                 155                 160

Val Lys Asn Pro Ile Leu Arg Tyr His Phe His Pro Ile Asp Pro Ser
            165                 170                 175

Phe Lys Pro Tyr Gly Asp Phe Ala Thr Trp Arg Thr Thr Val Arg Asn
            180                 185                 190

Pro Asp Arg Asn Arg Arg Glu Asp Ile Pro Gly Leu Ile Lys Lys Met
            195                 200                 205

Arg Leu Glu Glu Gly Gln Ile Arg Glu Lys Thr Tyr Asn Met Leu Lys
            210                 215                 220

Phe Asn Asp Ala Trp Glu Arg Phe Ser Asn His Gly Ile Ser Asp Asp
225                 230                 235                 240
```

```
Gln His Ala Asn Ser Leu Glu Ser Val His Asp Asp Ile His Val Met
                245                 250                 255

Val Gly Tyr Gly Lys Ile Glu Gly His Met Asp His Pro Phe Phe Ala
            260                 265                 270

Ala Phe Asp Pro Ile Phe Trp Leu His His Thr Asn Val Asp Arg Leu
        275                 280                 285

Leu Ser Leu Trp Lys Ala Ile Asn Pro Asp Val Trp Val Thr Ser Gly
    290                 295                 300

Arg Asn Arg Asp Gly Thr Met Gly Ile Ala Pro Asn Ala Gln Ile Asn
305                 310                 315                 320

Ser Glu Thr Pro Leu Glu Pro Phe Tyr Gln Ser Gly Asp Lys Val Trp
                325                 330                 335

Thr Ser Ala Ser Leu Ala Asp Thr Ala Arg Leu Gly Tyr Ser Tyr Pro
            340                 345                 350

Asp Phe Asp Lys Leu Val Gly Gly Thr Lys Glu Leu Ile Arg Asp Ala
        355                 360                 365

Ile Asp Asp Leu Ile Asp Glu Arg Tyr Gly Ser Lys Pro Ser Ser Gly
    370                 375                 380

Ala Arg Asn Thr Ala Phe Asp Leu Leu Ala Asp Phe Lys Gly Ile Thr
385                 390                 395                 400

Lys Glu His Lys Glu Asp Leu Lys Met Tyr Asp Trp Thr Ile His Val
                405                 410                 415

Ala Phe Lys Lys Phe Glu Leu Lys Glu Ser Phe Ser Leu Leu Phe Tyr
            420                 425                 430

Phe Ala Ser Asp Gly Gly Asp Tyr Asp Gln Glu Asn Cys Phe Val Gly
        435                 440                 445

Ser Ile Asn Ala Phe Arg Gly Thr Ala Pro Glu Thr Cys Ala Asn Cys
    450                 455                 460

Gln Asp Asn Glu Asn Leu Ile Gln Glu Gly Phe Ile His Leu Asn His
465                 470                 475                 480

Tyr Leu Ala Arg Asp Leu Glu Ser Phe Glu Pro Gln Asp Val His Lys
                485                 490                 495

Phe Leu Lys Glu Lys Gly Leu Ser Tyr Lys Leu Tyr Ser Arg Gly Asp
            500                 505                 510

Lys Pro Leu Thr Ser Leu Ser Val Lys Ile Glu Gly Arg Pro Leu His
        515                 520                 525

Leu Pro Pro Gly Glu His Arg Pro Lys Tyr Asp His Thr Gln Ala Arg
    530                 535                 540

Val Val Phe Asp Asp Val Ala Val His Val Ile Asn
545                 550                 555

<210> SEQ ID NO 40
<211> LENGTH: 273
<212> TYPE: PRT
<213> ORGANISM: Streptomyces castaneglobisporus

<400> SEQUENCE: 40

Met Thr Val Arg Lys Asn Gln Ala Thr Leu Thr Ala Asp Glu Lys Arg
  1               5                  10                  15

Arg Phe Val Ala Ala Val Leu Glu Leu Lys Arg Ser Gly Arg Tyr Asp
            20                  25                  30

Glu Phe Val Arg Thr His Asn Glu Phe Ile Met Ser Asp Thr Asp Ser
        35                  40                  45

Gly Glu Arg Thr Gly His Arg Ser Pro Ser Phe Leu Pro Trp His Arg
    50                  55                  60
```

```
Arg Phe Leu Leu Asp Phe Glu Gln Ala Leu Gln Ser Val Asp Ser Ser
 65                  70                  75                  80

Val Thr Leu Pro Tyr Trp Asp Trp Ser Ala Asp Arg Thr Val Arg Ala
                 85                  90                  95

Ser Leu Trp Ala Pro Asp Phe Leu Gly Gly Thr Gly Arg Ser Thr Asp
            100                 105                 110

Gly Arg Val Met Asp Gly Pro Phe Ala Ala Phe Thr Gly Asn Trp Pro
        115                 120                 125

Ile Asn Val Arg Val Asp Ser Arg Thr Tyr Leu Arg Arg Ser Leu Gly
130                 135                 140

Gly Ser Val Ala Glu Leu Pro Thr Arg Ala Glu Val Glu Ser Val Leu
145                 150                 155                 160

Ala Ile Ser Ala Tyr Asp Leu Pro Pro Tyr Asn Ser Ala Ser Glu Gly
                165                 170                 175

Phe Arg Asn His Leu Glu Gly Trp Arg Gly Val Asn Leu His Asn Arg
            180                 185                 190

Val His Val Trp Val Gly Gly Gln Met Ala Thr Gly Val Ser Pro Asn
        195                 200                 205

Asp Pro Val Phe Trp Leu His His Ala Tyr Val Asp Lys Leu Trp Ala
210                 215                 220

Glu Trp Gln Arg Arg His Pro Asp Ser Ala Tyr Val Pro Thr Gly Gly
225                 230                 235                 240

Thr Pro Asp Val Val Asp Leu Asn Glu Thr Met Lys Pro Trp Asn Thr
                245                 250                 255

Val Arg Pro Ala Asp Leu Leu Asp His Thr Ala Tyr Tyr Thr Phe Asp
            260                 265                 270

Ala

<210> SEQ ID NO 41
<211> LENGTH: 258
<212> TYPE: PRT
<213> ORGANISM: Unknown
<220> FEATURE:
<223> OTHER INFORMATION: isolated from soil

<400> SEQUENCE: 41

Met Arg Pro Gly Leu Val Leu Arg Ser Phe Thr Tyr Ala Pro Trp Pro
  1               5                  10                  15

Val Leu Leu Ala Thr Ala Gly Phe Gly Leu Ala Leu Ser Ile Tyr Ser
                 20                  25                  30

Asp Ala Ser Thr Glu Gly Pro Ala Phe Cys Val Ala Thr Asn Gly Leu
             35                  40                  45

Ser Ile Phe Thr Ser Trp Pro Ala Val Leu Gln Ala Glu Leu Ala Val
         50                  55                  60

Asn Pro Ile His Arg Ile Leu Ala Gly Trp Leu Leu Met Leu Leu Thr
 65                  70                  75                  80

Met Met Pro Pro Leu Leu Ala Met Pro Leu Met His Val Trp Arg Ser
                 85                  90                  95

Ser Leu Pro Asn Arg Arg Ile Arg Ala Ser Ala Gly Phe Leu Leu Gly
            100                 105                 110

Tyr Cys Ala Pro Trp Met Ala Ala Gly Leu Val Leu Ser Ala Leu Ala
        115                 120                 125

Leu Leu Leu Gln Ile Thr Val Val Asp Asn Ala Leu Ala Ile Ala Leu
130                 135                 140

Leu Ile Ala Leu Leu Trp Ser Ala Ser Pro Trp His Arg Ala Ala Leu
145                 150                 155                 160
```

```
Asn Arg Ser His Gln Pro Arg Arg Ile Gly Leu Phe Gly Arg Ala Ala
                165                 170                 175
Asp Arg Asp Cys Leu Val Phe Gly Met Thr His Gly Ala Tyr Cys Ile
            180                 185                 190
Gly Ser Cys Trp Ala Trp Met Leu Val Pro Val Ser Gly Ala Trp
        195                 200                 205
His Ile Pro Met Met Leu Phe Thr Gly Val Ile Met Leu Ala Glu Arg
    210                 215                 220
Phe Thr Pro Pro Gly Pro Ala Arg Trp Cys Trp Pro Arg Phe Phe Ser
225                 230                 235                 240
Pro Ala His Leu Tyr Thr Leu Leu Thr Gln Arg Asn Ala Glu Arg Pro
                245                 250                 255
His Gly

<210> SEQ ID NO 42
<211> LENGTH: 37
<212> TYPE: PRT
<213> ORGANISM: Artificial Sequence
<220> FEATURE:
<223> OTHER INFORMATION: N-terminal sequence of protein from active
      fractions of strain ATX26455

<400> SEQUENCE: 42

Met Asn Thr Ile Arg Gln Asp Val Ala Thr Leu Gly Ser Gly Trp Asp
  1               5                  10                  15
Asn Lys Val Leu Leu Asn Tyr Ala Leu Ala Met Arg Glu Leu Asp Lys
             20                  25                  30
Leu Pro Ile Thr Asn
         35

<210> SEQ ID NO 43
<211> LENGTH: 30
<212> TYPE: DNA
<213> ORGANISM: Artificial Sequence
<220> FEATURE:
<223> OTHER INFORMATION: olignonucleotide primer
<220> FEATURE:
<221> NAME/KEY: misc_feature
<222> LOCATION: 3
<223> OTHER INFORMATION: n = A or G
<220> FEATURE:
<221> NAME/KEY: misc_feature
<222> LOCATION: 6, 16
<223> OTHER INFORMATION: n = C or T
<220> FEATURE:
<221> NAME/KEY: misc_feature
<222> LOCATION: 9, 12, 15, 18, 21, 24, 27
<223> OTHER INFORMATION: n = inosine

<400> SEQUENCE: 43
cangangtng cnacnntngg nccnggntgg                                    30

<210> SEQ ID NO 44
<211> LENGTH: 24
<212> TYPE: DNA
<213> ORGANISM: Artificial Sequence
<220> FEATURE:
<223> OTHER INFORMATION: olignonucleotide primer
<220> FEATURE:
<221> NAME/KEY: misc_feature
<222> LOCATION: 1, 4, 13, 22
<223> OTHER INFORMATION: n = A or G
<220> FEATURE:
<221> NAME/KEY: misc_feature
<222> LOCATION: 7, 16, 19
<223> OTHER INFORMATION: n = inosine
```

<400> SEQUENCE: 44
ntgntgnagc canaanatng gntc                                          24

<210> SEQ ID NO 45
<211> LENGTH: 1971
<212> TYPE: DNA
<213> ORGANISM: Pseudomonas aurantiaca

<400> SEQUENCE: 45

```
ctgagcatct gggaacacca gcagttgcag cgcctgctgc aggcgttgtg aacaaaggtt     60
ccttccatta cacccacgcc aatcctccgt ccgtccgccc aagccaccgg aacccgtgtc    120
gttcatcggg ataatgggaa tcggccatgg cgttttttgcc aggcctctat actcattttc   180
gacgaggcgc gcaccggcac tgcgggcctc atgagcgcag tkscgycgwg agacatgaag    240
tcgccagcgg caaaggattg cgaggggtgt ggcgccatac gcgtcacctg gcctgatgct    300
gcaaggaagg tgcattcatg aacacgatcc gacaggatgt ggcaacactc ggctccggat    360
gggacaacaa ggtcttgctc aactacgcgc tggccatgcg cgagctggac aaaactaccga   420
tcaccaaccg caacagctgg aagttcctcg gcgccatcca cggcttcgat cggcagttgt    480
gggtcgaggt gaatgtcctg ggcgattccg atccggttcc caaggacctg accaacttta    540
cctacgcag ccagtgccag cacggcagct ggtacttcct gtcctggcac gcggttacc     600
tggcggcctt cgaggcgatt gtcgcggcca aggtcaagga actgacgggt gacgactggg    660
cgctgccgta ctggaactac ctcaatagca aaaacccgga tgcgcggcgg gccccggagg    720
cattcctggc ggacacctg cctgacggca gcccaaccc gctgaagaaa taccctcgcc     780
ggcagggctt taccacgctg cggccgaact ccctcgatgc cttcagcctg gcggcaatgc    840
aggagaacga tttccaggtc ggcaatgacg gcagcatcgg cttcggcggc ggggtcaccg    900
gcaatttcgc ccagttcgcc cgctggaccg gcgacctgga gaacaacccg cacaacaccg    960
tgcatcgtct gatcggcggg ggcgaaggct tcatggccga cccgtacctc gccgccctgg   1020
acccgatctt ctggttgcac cattgcaacg tcgaccggct ctgggaggcc tggatgaaca   1080
ccccgggcaa gaccatggtc cgcgatccgc gctggctcga cggtccggcc gaccgccgtt   1140
tcatcatgcc gacggtcggt ggcagtgacc ctggcatgaa attcaccggc cgcgacacat   1200
tgaaggatgg caaattgcat ccgcgctatg ccgacttgag catcggcacg ggcgtgaaac   1260
caggagtaga ggccgtgaca cgggtcaaga tgggtgcgcc ggaacaacag aacatcgaac   1320
cgatcggtgc caaccgttcg gtggtcacgg tcggcggcgc gccggtgcgc acccaggtcg   1380
acctcgaccg ccaggccacc agcaccggga tcgccgcgat gggcgcgacg gacctgggcc   1440
agccggtgac ccggctctac ctggcgctgg aatcggtgcg cggctccgcg ccctcgccgc   1500
agcttacggt gtacatcaac ctgccgaaag acagcgaccc gcagcagcat cccgagtgcc   1560
atgccggcag cctgacgctg ttcgggctga acgtcgcctc gcggccagac ggtggccatg   1620
gcggccacgg gctcggctat acgatcgaca tcaccgacct ggcccagcgg ctgaccgatg   1680
ccggcgattt cgatcccgac tatctgcggg tgaccctggt cccaggcgag caggtatcgg   1740
cggataaacc ggtgaccgtg gagcggatca gcgtgctcaa gcgcagtggt atcgtcagct   1800
gagtaacgcc tcatgcaacc cggaccggtc ttgctcagct tcaccggggc gccctggccg   1860
ttgctgttcg cgacggcggg gctgggcctg gccctgtgtc tctacaccgc cgggcacagc   1920
accctgcccg ccttctgcgg ttccgcgcta tccatcgttg ccagttggcc c            1971
```

```
<210> SEQ ID NO 46
<211> LENGTH: 1482
<212> TYPE: DNA
<213> ORGANISM: Pseudomonas aurantiaca

<400> SEQUENCE: 46
atgaacacga tccgacagga tgtggcaaca ctcggctccg gatgggacaa caaggtcttg      60
ctcaactacg cgctggccat gcgcgagctg gacaaactac cgatcaccaa ccgcaacagc     120
tggaagttcc tcggcgccat ccacggcttc gatcggcagt tgtgggtcga ggtgaatgtc     180
ctgggcgatt ccgatccggt tcccaaggac ctgaccaact ttacctacgg cagccagtgc     240
cagcacggca gctggtactt cctgtcctgg caccgcggtt acctggcggc cttcgaggcg     300
attgtcgcgg ccaaggtcaa ggaactgacg ggtgacgact gggcgctgcc gtactggaac     360
tacctcaata gcaaaaaccc ggatgcgcgg cgggccccgg aggcattcct ggcggacacc     420
ctgcctgacg gcagccccaa cccgctgaag aaatacccta gccggcaggg ctttaccacg     480
ctgcggccga actccctcga tgccttcagc ctggcggcaa tgcaggagaa cgatttccag     540
gtcggcaatg acggcagcat cggcttcggc ggcggggtca ccggcaattt cgcccagttc     600
gcccgctgga ccggcgacct ggagaacaac ccgcacaaca ccgtgcatcg tctgatcggc     660
gggggcgaag gcttcatggc cgacccgtac ctcgccgccc tggacccgat cttctggttg     720
caccattgca acgtcgaccg gctctgggag gcctggatga acaccccggg caagaccatg     780
gtccgcgatc cgcgctggct cgacggtccg gccgaccgcc gtttcatcat gccgacggtc     840
ggtggcagtg accctggcat gaaattcacc ggccgcgaca cattgaagga tgcaaaattg     900
catccgcgct atgccgactt gagcatcggc acgggcgtga accaggagt agaggccgtg      960 acacgggtca agatgggtgc gccggaacaa cagaacatcg aaccgatcgg tgccaaccgt    1020
tcggtggtca cggtcggcgg cgcgccggtg cgcacccagg tcgacctcga ccgccaggcc    1080
accagcaccg ggatcgccgc gatgggcgcg acggacctgg ccagccggt gacccggctc     1140 tacctggcgc tggaatcggt gcgcggctcc gcgccctcgc cgcagcttac ggtgtacatc    1200
aacctgccga agacagcga cccgcagcag catcccgagt gccatgccgg cagcctgacg     1260
ctgttcgggc tgaacgtcgc ctcgcggcca gacggtggcc atggcggcca cgggctcggc    1320
tatacgatcg acatcaccga cctggcccag cggctgaccg atgccggcga tttcgatccc    1380
gactatctgc gggtgaccct ggtcccaggc gagcaggtat cggcggataa accggtgacc    1440
gtggagcgga tcagcgtgct caagcgcagt ggtatcgtca gc                       1482

<210> SEQ ID NO 47
<211> LENGTH: 494
<212> TYPE: PRT
<213> ORGANISM: Pseudomonas aurantiaca

<400> SEQUENCE: 47

Met Asn Thr Ile Arg Gln Asp Val Ala Thr Leu Gly Ser Gly Trp Asp
 1               5                  10                  15

Asn Lys Val Leu Leu Asn Tyr Ala Leu Ala Met Arg Glu Leu Asp Lys
            20                  25                  30

Leu Pro Ile Thr Asn Arg Asn Ser Trp Lys Phe Leu Gly Ala Ile His
        35                  40                  45

Gly Phe Asp Arg Gln Leu Trp Val Glu Val Asn Val Leu Gly Asp Ser
    50                  55                  60

Asp Pro Val Pro Lys Asp Leu Thr Asn Phe Thr Tyr Gly Ser Gln Cys
65                  70                  75                  80
```

```
Gln His Gly Ser Trp Tyr Phe Leu Ser Trp His Arg Gly Tyr Leu Ala
                 85                  90                  95

Ala Phe Glu Ala Ile Val Ala Ala Lys Val Lys Glu Leu Thr Gly Asp
            100                 105                 110

Asp Trp Ala Leu Pro Tyr Trp Asn Tyr Leu Asn Ser Lys Asn Pro Asp
            115                 120                 125

Ala Arg Arg Ala Pro Glu Ala Phe Leu Ala Asp Thr Leu Pro Asp Gly
            130                 135                 140

Ser Pro Asn Pro Leu Lys Lys Tyr Pro Arg Arg Gln Gly Phe Thr Thr
145                 150                 155                 160

Leu Arg Pro Asn Ser Leu Asp Ala Phe Ser Leu Ala Ala Met Gln Glu
                165                 170                 175

Asn Asp Phe Gln Val Gly Asn Asp Gly Ser Ile Gly Phe Gly Gly Gly
            180                 185                 190

Val Thr Gly Asn Phe Ala Gln Phe Ala Arg Trp Thr Gly Asp Leu Glu
            195                 200                 205

Asn Asn Pro His Asn Thr Val His Arg Leu Ile Gly Gly Glu Gly
210                 215                 220

Phe Met Ala Asp Pro Tyr Leu Ala Ala Leu Asp Pro Ile Phe Trp Leu
225                 230                 235                 240

His His Cys Asn Val Asp Arg Leu Trp Glu Ala Trp Met Asn Thr Pro
                245                 250                 255

Gly Lys Thr Met Val Arg Asp Pro Arg Trp Leu Asp Gly Pro Ala Asp
                260                 265                 270

Arg Arg Phe Ile Met Pro Thr Val Gly Ser Asp Pro Gly Met Lys
                275                 280                 285

Phe Thr Gly Arg Asp Thr Leu Lys Asp Gly Lys Leu His Pro Arg Tyr
290                 295                 300

Ala Asp Leu Ser Ile Gly Thr Gly Val Lys Pro Gly Val Glu Ala Val
305                 310                 315                 320

Thr Arg Val Lys Met Gly Ala Pro Glu Gln Gln Asn Ile Glu Pro Ile
                325                 330                 335

Gly Ala Asn Arg Ser Val Val Thr Val Gly Gly Ala Pro Val Arg Thr
                340                 345                 350

Gln Val Asp Leu Asp Arg Gln Ala Thr Ser Thr Gly Ile Ala Ala Met
                355                 360                 365

Gly Ala Thr Asp Leu Gly Gln Pro Val Thr Arg Leu Tyr Leu Ala Leu
            370                 375                 380

Glu Ser Val Arg Gly Ser Ala Pro Ser Pro Gln Leu Thr Val Tyr Ile
385                 390                 395                 400

Asn Leu Pro Lys Asp Ser Asp Pro Gln Gln His Pro Glu Cys His Ala
                405                 410                 415

Gly Ser Leu Thr Leu Phe Gly Leu Asn Val Ala Ser Arg Pro Asp Gly
                420                 425                 430

Gly His Gly Gly His Gly Leu Gly Tyr Thr Ile Asp Ile Thr Asp Leu
            435                 440                 445

Ala Gln Arg Leu Thr Asp Ala Gly Asp Phe Asp Pro Asp Tyr Leu Arg
            450                 455                 460

Val Thr Leu Val Pro Gly Glu Gln Val Ser Ala Asp Lys Pro Val Thr
465                 470                 475                 480

Val Glu Arg Ile Ser Val Leu Lys Arg Ser Gly Ile Val Ser
                485                 490
```

<210> SEQ ID NO 48

```
<211> LENGTH: 487
<212> TYPE: PRT
<213> ORGANISM: Pseudomonas aurantiaca

<400> SEQUENCE: 48

Met Ala Thr Leu Gly Ser Gly Trp Asp Asn Lys Val Leu Leu Asn Tyr
1               5                   10                  15

Ala Leu Ala Met Arg Glu Leu Asp Lys Leu Pro Ile Thr Asn Arg Asn
            20                  25                  30

Ser Trp Lys Phe Leu Gly Ala Ile His Gly Phe Asp Arg Gln Leu Trp
        35                  40                  45

Val Glu Val Asn Val Leu Gly Asp Ser Asp Pro Val Pro Lys Asp Leu
    50                  55                  60

Thr Asn Phe Thr Tyr Gly Ser Gln Cys Gln His Gly Ser Trp Tyr Phe
65                  70                  75                  80

Leu Ser Trp His Arg Gly Tyr Leu Ala Ala Phe Glu Ala Ile Val Ala
                85                  90                  95

Ala Lys Val Lys Glu Leu Thr Gly Asp Asp Trp Ala Leu Pro Tyr Trp
            100                 105                 110

Asn Tyr Leu Asn Ser Lys Asn Pro Asp Ala Arg Arg Ala Pro Glu Ala
        115                 120                 125

Phe Leu Ala Asp Thr Leu Pro Asp Gly Ser Pro Asn Pro Leu Lys Lys
    130                 135                 140

Tyr Pro Arg Arg Gln Gly Phe Thr Thr Leu Arg Pro Asn Ser Leu Asp
145                 150                 155                 160

Ala Phe Ser Leu Ala Ala Met Gln Glu Asn Asp Phe Gln Val Gly Asn
                165                 170                 175

Asp Gly Ser Ile Gly Phe Gly Gly Val Thr Gly Asn Phe Ala Gln
            180                 185                 190

Phe Ala Arg Trp Thr Gly Asp Leu Glu Asn Asn Pro His Asn Thr Val
    195                 200                 205

His Arg Leu Ile Gly Gly Gly Glu Gly Phe Met Ala Asp Pro Tyr Leu
210                 215                 220

Ala Ala Leu Asp Pro Ile Phe Trp Leu His His Cys Asn Val Asp Arg
225                 230                 235                 240

Leu Trp Glu Ala Trp Met Asn Thr Pro Gly Lys Thr Met Val Arg Asp
                245                 250                 255

Pro Arg Trp Leu Asp Gly Pro Ala Asp Arg Arg Phe Ile Met Pro Thr
            260                 265                 270

Val Gly Gly Ser Asp Pro Gly Met Lys Phe Thr Gly Arg Asp Thr Leu
        275                 280                 285

Lys Asp Gly Lys Leu His Pro Arg Tyr Ala Asp Leu Ser Ile Gly Thr
    290                 295                 300

Gly Val Lys Pro Gly Val Glu Ala Val Thr Arg Val Lys Met Gly Ala
305                 310                 315                 320

Pro Glu Gln Gln Asn Ile Glu Pro Ile Gly Ala Asn Arg Ser Val Val
                325                 330                 335

Thr Val Gly Gly Ala Pro Val Arg Thr Gln Val Asp Leu Asp Arg Gln
            340                 345                 350

Ala Thr Ser Thr Gly Ile Ala Ala Met Gly Ala Thr Asp Leu Gly Gln
        355                 360                 365

Pro Val Thr Arg Leu Tyr Leu Ala Leu Glu Ser Val Arg Gly Ser Ala
    370                 375                 380

Pro Ser Pro Gln Leu Thr Val Tyr Ile Asn Leu Pro Lys Asp Ser Asp
385                 390                 395                 400
```

```
-continued

Pro Gln Gln His Pro Glu Cys His Ala Gly Ser Leu Thr Leu Phe Gly
            405                 410                 415

Leu Asn Val Ala Ser Arg Pro Asp Gly His Gly Gly His Gly Leu
            420                 425                 430

Gly Tyr Thr Ile Asp Ile Thr Asp Leu Ala Gln Arg Leu Thr Asp Ala
            435                 440                 445

Gly Asp Phe Asp Pro Asp Tyr Leu Arg Val Thr Leu Val Pro Gly Glu
        450                 455                 460

Gln Val Ser Ala Asp Lys Pro Val Thr Val Glu Arg Ile Ser Val Leu
465                 470                 475                 480

Lys Arg Ser Gly Ile Val Ser
                485
```

GENES ENCODING NEMATODE TOXINS

CROSS REFERENCE TO RELATED APPLICATION

This application claims the benefit of U.S. Provisional Application Ser. No. 61/122,674, filed Dec. 15, 2008 and U.S. Provisional Application Ser. No. 61/224,811, filed Jul. 10, 2009, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "382973_SequenceListing.txt", created on Dec. 15, 2009, and having a size of 165 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode nematicidal proteins. These proteins and the nucleic acid sequences that encode them are useful in preparing nematicidal formulations and in the production of transgenic pest-resistant plants.

BACKGROUND OF THE INVENTION

Nematodes (derived from the Greek word for thread) are active, flexible, elongate, organisms that live on moist surfaces or in liquid environments, including films of water within soil and moist tissues within other organisms. While only 20,000 species of nematode have been identified, it is estimated that 40,000 to 10 million actually exist. Some species of nematodes have evolved to be very successful parasites of both plants and animals and are responsible for significant economic losses in agriculture and livestock and for morbidity and mortality in humans (Whitehead (1998) Plant Nematode Control. CAB International, New York).

It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al. (1994) Plant and Soil Nematodes: Societal Impact and Focus for the Future. The Committee on National Needs and Priorities in Nematology. Cooperative State Research Service, US Department of Agriculture and Society of Nematologists).

There are a very small array of chemicals available to control nematodes (Becker (1999) Agricultural Research Magazine 47(3):22-24; U.S. Pat. No. 6,048,714). Nevertheless, the application of chemical nematicides remains the major means of nematode control. In general, chemical nematicides are highly toxic compounds known to cause substantial environmental impact and are increasingly restricted in the amounts and locations in which then can be used.

The macrocyclic lactones (e.g., avermectins and milbemycins) are chemicals that in principle provide excellent specificity and efficacy and should allow environmentally safe control of plant parasitic nematodes. Unfortunately, in practice, these two nematicidal agents have proven less effective in agricultural applications against root pathogens. Although certain avermectins show exquisite activity against plant parasitic nematodes these chemicals are hampered by poor bioavailability due to their light sensitivity, degradation by soil microorganisms and tight binding to soil particles (Lasota & Dybas (1990) Acta Leiden 59(1-2):217-225; Wright & Perry (1998) Musculature and Neurobiology. In: The Physiology and Biochemistry of Free-Living and Plant-parasitic Nematodes (eds R. N. Perry & D. J. Wright), CAB International 1998). Consequently despite years of research and extensive use against animal parasitic nematodes, mites and insects (plant and animal applications), macrocyclic lactones (e.g., avermectins and milbemycins) have never been commercially developed to control plant parasitic nematodes in the soil.

SUMMARY OF INVENTION

Compositions and methods for conferring nematode tolerance activity to plants, plant cells, tissues and seeds are provided. Compositions include nucleic acid molecules encoding sequences for nematicidal polypeptides, vectors comprising those nucleic acid molecules, and host cells comprising the vectors. Compositions also include the nematicidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules are provided that encode nematicidal proteins. Additionally, amino acid sequences corresponding to the nematicidal protein are encompassed. In particular, the present invention provides for an isolated nucleic acid molecule comprising a nucleotide sequence encoding the amino acid sequence shown in SEQ ID NO:4, 5, 8, 9, 13, 14, 47, 48, or 49, the nucleotide sequence set forth in SEQ ID NO:1, 2, 3, 6, 7, 10, 11, 12, 15, 45, or 46, as well as variants and fragments thereof. Nucleotide sequences that are complementary to a nucleotide sequence of the invention, or that hybridize to a sequence of the invention are also encompassed.

Methods are provided for producing the polypeptides of the invention, and for using those polypeptides for controlling or killing a nematode pest. Methods and kits for detecting the nucleic acids and polypeptides of the invention in a sample are also included.

The compositions and methods of the invention are useful for the production of organisms with enhanced nematode resistance or tolerance. These organisms and compositions comprising the organisms are desirable for agricultural purposes. The compositions of the invention are useful for identifying and generating plant populations having improved nematode resistance, as well as in the identification of Quantitative Trait Loci (QTLs) useful in marker-assisted breeding of plants having nematode resistance or tolerance.

DESCRIPTION OF FIGURES

FIG. 1 shows the enzymatic action of polyphenol oxidases.
FIG. 2 shows the AXN-1 precursor protein (SEQ ID NO:13) with the mass spectroscopy peaks mapped.
FIGS. 3A and 3B show an alignment of AXN-1 (SEQ ID NO:4) with polyphenol oxidases from *Neurospora crassa*

Figure 6:
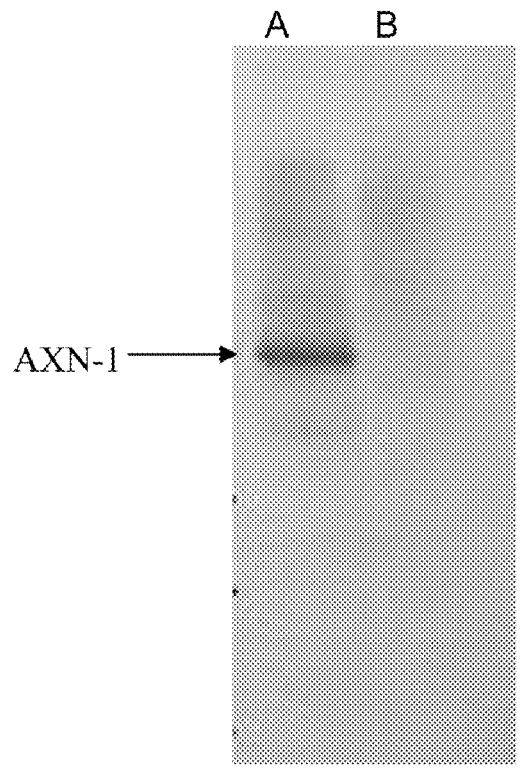

(SEQ ID NO:31), *Pyrenophora triticirepentis* (SEQ ID NO:32), *Podospora anserina* (SEQ ID NO:33), *Lentinula edodes* (SEQ ID NO:34), *Pycnoporus sanguineus* (SEQ ID NO:35), *Pholio nameko* (SEQ ID NO:36), *Tuber melanosporum* (SEQ ID NO:37), and *Aspergillus fumigatus* (SEQ ID NO:38).

FIG. 4 shows an alignment of AXN-8 (SEQ ID NO:13) with polyphenol oxidases from *Agaricus bisporus* (SEQ ID NO:39), *Neurospora crassa* (SEQ ID NO:31), and *Streptomyces castaneglobisporus* (SEQ ID NO:40). Putative copper binding histidines are found at amino acid positions 47, 81, 90, 208, 212, and 235 of SEQ ID NO:13. The protease activation site is located at position 377 of SEQ ID NO:39 and position 403 of SEQ ID NO:31. Copper binding histidines are located at amino acid position 58 of SEQ ID NO:39, position 67 of SEQ ID NO:31, and positions 38, 54, 63, 190, 194, and 216 of SEQ ID NO:40.

FIG. 5 shows an alignment of AXN-9 (SEQ ID NO:48) with AXN-8 (SEQ ID NO:13).

FIG. 6 shows a Western blot of soybean hairy root tissue incubated with anti-AXN-1 antibody. Lane A is root tissue from transgenic root tissue containing the AXN-1 gene, and Lane B is from a control line lacking the AXN-1 gene.

DETAILED DESCRIPTION

Overview

Nematodes cause a substantial loss in agricultural products including food and industrial crops and have primarily been combated with chemical compounds having nematicidal activity. Nematodes are microscopic wormlike animals that feed on roots, leaves, and stems of more than 2,000 vegetables, fruits, and ornamental plants. One common type of nematode is the root-knot nematode, whose feeding causes the characteristic galls on roots. Other root-feeding nematodes are the cyst- and lesion-type, which are more host specific. Soybean cyst nematode (SCN) can decrease the number of nitrogen-fixing nodules on the roots, and may make the roots more susceptible to attacks by other soil-borne plant pathogens. Due to the toxicity (and in many cases, poor efficacy) of existing nematode control methods, it would be desirable to develop safe and effective alternatives for nematode control.

The present invention is drawn to compositions and methods for regulating nematode resistance or tolerance in organisms, particularly plants or plant cells. By "resistance" is intended that the nematode is killed upon ingestion or other contact with the polypeptides of the invention. By "tolerance" is intended an impairment or reduction in the movement, feeding, reproduction, or other functions of the nematode. The methods involve transforming organisms with a nucleotide sequence encoding a nematicidal protein of the invention. In particular, the nucleotide sequences of the invention are useful for preparing plants and microorganisms that possess nematicidal activity. Thus, transformed bacteria, plants, plant cells, plant tissues and seeds are provided.

Compositions include nematicidal nucleic acids and proteins of bacterial, fungal, or plant origin. The nematicidal nucleic acid sequences described herein encode polyphenol oxidase enzymes. Polyphenol oxidases are believed to play key physiological roles both in preventing insects and microorganisms from attacking plants and as part of the wound response of plants and plant products to insects, microorganisms and bruising (reviewed in Marshall et al. (2000) "Enzymatic Browning in Fruits, Vegetables and Seafoods" *Food and Agricultural Organization of the United Nations* at www.fao.org). As fruits and vegetables ripen, their susceptibility to disease and infestation is increased due to a decline in their phenolic content. Phenoloxidase enzymes endogenous to fruits and vegetables catalyze the production of quinones from their phenolic constituents. Once formed, these quinones undergo polymerization reactions, leading to the production of melanins, which exhibit both antibacterial and antifungal activity and assist in keeping the fruit and/or vegetable physiologically wholesome. However, the use of polyphenol oxidase activity for nematode control has not previously been discovered.

The polyphenol oxidase enzymes encompassed herein include novel sequences as well as polyphenol oxidase sequences known in the art. The sequences find use in the construction of expression vectors for subsequent transformation into organisms of interest, as probes for the isolation of other homologous (or partially homologous) genes, and for the generation of altered nematicidal proteins by methods known in the art, such as domain swapping or DNA shuffling. The proteins find use in controlling or killing nematode pest populations and for producing compositions with nematicidal activity.

By "nematicidal toxin" or "nematicidal protein" is intended a toxin that has toxic activity against one or more nematode pests, including, but not limited to, the nematicidal toxins set forth in SEQ ID NO:4, 5, 8, 9, 13, 14, 18, 20, 22, 47, 48, or 49, or a protein that has homology to such a protein. Nematicidal proteins include amino acid sequences deduced from the full-length nucleotide sequences disclosed herein, and amino acid sequences that are shorter than the full-length sequences, either due to the use of an alternate downstream start site, or due to processing (e.g., proteolytic cleavage, alternative splicing, and the like) that produces a shorter protein having nematicidal activity. Processing may occur in the organism the protein is expressed in, or in the pest after ingestion of the protein.

Nematode Pests

The compositions and methods of the present invention are useful for developing transgenic plants that are tolerant to nematode pests, particularly plant-parasitic nematodes. Nematode parasites of plants can inhabit all parts of plants, including roots, developing flower buds, leaves, and stems. Plant parasites are classified on the basis of their feeding habits into the broad categories: migratory ectoparasites, migratory endoparasites, and sedentary endoparasites. Sedentary endoparasites, which include the root knot nematodes (Meloidogyne) and cyst nematodes (Globodera and Heterodera) induce feeding sites and establish long-term infections within roots that are often very damaging to crops (Whitehead (1998) Plant Nematode Control. CAB International, New York). Exemplary plant-parasitic nematodes include, but are not limited to, *Aphelenchoides* spp. (Foliar nematodes), *Belonolaimus* spp. (The Sting nematode), *Bursaphelenchus xylophilus* (Pine wilt nematode), *Criconemoides* species (Ring Nematode), *Ditylenchus destructor* (Potato Rot Nematode), *Ditylenchus dipsaci* (Stem and bulb nematode), *Globodera pallida* (Pale Potato Cyst Nematode), *Globodera rostochiensis* (Golden Nematode), *Helicotylenchus* (Spiral Nematodes), *Heterodera glycines* (Soybean cyst nematode, *Heterodera schachtii* (Sugar beet cyst nematode), *Heterodera zeae* (The Corn Cyst Nematode), *Heterodera avenae* (cereal cyst nematode), *Hoplolaimus* (The Lance Nematode), *Meloidogyne* spp. (Root-knot nematodes), *Mesocriconema xenoplax* (Ring nematode), *Nacobbus aberrans* (False root-knot nematode), *Paratrichodorus* (Stubby-Root Nematodes), *Pratylenchus* spp (Lesion nematode), *Radopholus similis* (Burrowing nematode), *Rotylenchulus* spp. (Reniform nematode), *Tylenchorhynchus* spp.

(Stunt nematodes), *Tylenchulus semipenetrans* (The Citrus nematode), and *Xiphinema* (The Dagger Nematode).

Polyphenol Oxidases

The nematicidal compositions disclosed herein comprise polyphenol oxidase nucleic acid and amino acid sequences, as well as variants and fragments thereof. In various embodiments, the compositions comprise transgenic plants or pesticidal formulations expressing or comprising a polyphenol oxidase. The compositions are useful for controlling or killing plant-parasitic nematodes in an area susceptible to nematode infestation, particularly plant-parasitic nematode infestation.

For the purposes of the present invention, a "polyphenol oxidase" refers to a class of copper-containing oxidase enzymes that includes, for example, monophenol monooxidases such as tyrosinase, diphenol oxidases such as catechol oxidase and laccase, hemocyanins, and the like. In various embodiments, the polyphenol oxidase enzymes encompassed herein are members of the type 3 copper protein family.

Polyphenol oxidases are enzymes with a dinuclear copper center, with the copper ions serving to bind a molecular oxygen atom within the active site of the enzyme to allow catalysis. The oxidation state of each copper atom influences oxygen binding and thus oxidase activity at each step. In the case of a monophenol monooxidase, copper ions in the +2 oxidation state guide the addition of a hydroxyl group in the ortho-position on an existing phenol ring. Subsequently, a diphenol oxidase can bind this diphenol product and oxidize both hydroxyl moieties to generate the corresponding quinone. The diphenol oxidase activity takes place by reduction of the copper ions to the +1 state and binding to a molecular oxygen atom. While some organisms possess only a single polyphenol oxidase activity (notably plants, which carry out the diphenol oxidase step), other enzymes perform both the monooxidase and diphenol oxidase reactions. Several x-ray structures have been solved for type 3 copper enzymes, and distinct structural motifs are conserved among the enzymes. Notable is the active site of these enzymes, in which copper is bound by six or seven histidine residues and a single cysteine residue is highly conserved. The structural data also suggests most polyphenol oxidase enzymes have somewhat relaxed specificity for their substrates, and that the active site of the enzymes is flexible during catalysis.

The enzyme seems to be of almost universal distribution in animals, plants, fungi and bacteria. Primary protein sequences of polyphenol oxidases from *Streptomyces glaucescens* (Huber et al. 1985), *Streptomyces antibioticus* (Bernan et al. 1985) and *Neurospora crassa* (Lerch, 1982), tomato (Shahar et al. 1992; Newman et al. 1993), broad bean (Cary et al. 1992) potato (Hunt et al. 1993), mice (Shibahara et al. 1986) and humans (Kwon et al. 1987; Giebel et al. 1991) have been determined using cDNA sequencing techniques. Polyphenol oxidases of closely related plants, such as tomato and potato, show approximately 91 percent sequence homology, while those of tomato and fava bean show only 40 percent exact homology (Wong, 1995).

Despite low sequence identity amongst polyphenol oxidase enzymes derived from different species, they all have at their active site a dinuclear copper center, in which type 3 copper is bound to histidine residues, and this structure is highly conserved. Marusek et al. show that a number of important structural features are conserved in the N-terminal domains of polyphenol oxidases from various plants and fungi, including a tyrosine motif which can be considered a landmark indicating the beginning of the linker region connecting the N- and C-terminal domains. Sequence alignments and secondary structure predictions indicate that the C-terminal domains of polyphenol oxidases are likely to be similar in tertiary structure to that of hemocyanin (Marusek et al. (2006) *J Inorg Biochem.* 100(1):108-23, herein incorporated by reference in its entirety, particularly with respect to the description of conserved structural features of polyphenol oxidases).

The amino acid sequence of a considerable number of PPOs, on plants, fungi and other organisms derived from cloning of the enzyme, has now been published and many of the reports and reviews give such comparative information, e.g. van Gelder et al. (1997) Phytochemistry 45:1309-1323; Wichers et al. (2003) Appl. Microbiol. Biotechnol. 61:336-341; Cho et al. (2003) Proc. Nat. Acad. Sci. USA 100:10641-10646; Marusek et al. (2006) J Inorg Biochem. 100(1):108-23; Halaouili et al. (2006) J. Appl. Microbiol. 100:219-232; Hernandez-Romero et al. (2006) FEBS J. 273:257-270; Nakamura et al. (2000) Biochem. J. 350:537-545; and, Matoba et al. (2006) J. Biol. Chem. 281:8981-8990, each of which is herein incorporated by reference in its entirety. Polyphenol oxidase enzymes have been isolated from mammals, birds, fish, insects, reptiles, amphibians, fungi and bacteria.

Polyphenol oxidase exists in certain species as a zymogen or propolyphenol oxidase form, and proteases are also believed to be involved in the activation of the propolyphenol oxidase form. These proteases are thought to be induced by microbial activity, and also suggests that these enzymes can be activated by a host protease following an infection or invasion event. Secondary metabolites, such as glucans, glycoproteins, laminarins, lipopolysaccharides, etc., produced by organisms may also induce the activation of propolyphenol oxidase by proteases. These metabolites are also capable of activating the propolyphenol oxidase even in the absence of proteolytic activity.

In various plant species, polyphenol oxidase genes are encoded within the nucleus and undergo translation within the cytoplasm. Once formed, propolyphenol oxidase is transported to the chloroplast where it undergoes proteolytic cleavage, to produce the active polyphenol oxidase form (Vaughn et al., 1988, *Physiol. Plant.*, 72: 659-665).

Monophenol Monooxygenases

Monophenol monooxygenase (EC 1.14.18.1; CAS number: 9002-10-2) catalyses the hydroxylation of monophenols to o-diphenols. The enzyme is referred to as tyrosinase in animals, since L-tyrosine is the major monophenolic substrate. Tyrosine, on the other hand, which is a monohydroxy phenol, is an important amino acid. Hydroxylation of tyrosine leads to the formation of dihydroxyphenylalanine (DOPA).

In plants, the enzyme is sometimes referred to as cresolase owing to the ability of the enzyme to utilize the monophenolic substrate, cresol. Monophenol monooxygenase is also known as monophenol monooxidase, dopa oxidase, phenol oxidase, phenoloxidase, phenoloxidase A, phenoloxidase B, and tyrosinase.

Crystallographic structure of a *Streptomyces* derived tyrosinase in complex with a so called "caddie protein" is described in Matoba et al (2006) J. Biol. Chem. 281(13): 8981-8990, which is herein incorporated by reference in its entirety.

Diphenol Oxidases

Diphenol oxidase (EC 1.10.3.1; CAS number: 9002-10-2) is an enzyme that catalyses the oxidation of phenols such as catechol. Diphenol oxidases are also known as catechol oxidase, polyphenol oxidase, and polyphenoloxidase. Diphenol oxidase carries out the oxidation of phenols such as catechol, using dioxygen ($O_2$). In the presence of catechol, benzoquinone is formed. Hydrogens removed from catechol combine with oxygen to form water.

Catechol oxidase is a copper-containing enzyme whose activity is similar to that of tyrosinase, a related class of copper oxidases.

Laccase (p-diphenol oxidase, E.C. 1.10.3.2) (DPO) is a type of copper-containing polyphenol oxidase. It has the unique ability of oxidizing p-diphenols, thus allowing it to be distinguished from o-diphenol oxidases such as catechol oxidase. Several phenolic substrates, including polyphenols, methoxy-substituted phenols, diamines and a considerable range of other compounds serve as substrates for laccase (Thurston, 1994, *Microbiology*, 140: 19-26). Laccases occur in many phytopathogenic fungi and in certain higher plants (Mayer and Harel, 1991, Phenoloxidase and their significance in fruit and vegetables. In P.F. Fx, ed. *Food Enzymology*, p. 373. London, Elsevier).

Isolated Nucleic Acid Molecules, and Variants and Fragments Thereof

One aspect of the invention pertains to isolated or recombinant nucleic acid molecules comprising nucleotide sequences encoding nematicidal proteins and polypeptides or biologically active portions thereof, as well as nucleic acid molecules sufficient for use as hybridization probes to identify nucleic acid molecules encoding proteins with regions of sequence homology. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated nucleic acid molecule encoding a nematicidal protein can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A nematicidal protein that is substantially free of cellular material includes preparations of protein having less than about 30%, 20%, 10%, or 5% (by dry weight) of non-nematicidal protein (also referred to herein as a "contaminating protein").

Nucleotide sequences encoding the proteins of the present invention include the sequence set forth in SEQ ID NO:1, 2, 3, 6, 7, 10, 11, 12, 15, 16, 17, 19, 21, 45, or 46, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the nematicidal protein encoded by this nucleotide sequence are set forth in SEQ ID NO:4, 5, 8, 9, 13, 14, 18, 20, 22, 47, 48, or 49.

Nucleic acid molecules that are fragments of these nucleotide sequences encoding nematicidal proteins are also encompassed by the present invention. By "fragment" is intended a portion of the nucleotide sequence encoding a nematicidal protein. A fragment of a nucleotide sequence may encode a biologically active portion of a nematicidal protein, or it may be a fragment that can be used as a hybridization probe or PCR primer using methods disclosed below. Nucleic acid molecules that are fragments of a nucleotide sequence encoding a nematicidal protein comprise at least about 50, 100, 200, 300, 400, 500, 600, 700, 800, 900, 1000, 1100, 1200, 1300, 1350, 1400 contiguous nucleotides, or up to the number of nucleotides present in a full-length nucleotide sequence encoding a nematicidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the nematicidal protein and, hence, retain nematicidal and polyphenol oxidase activity. By "retains activity" is intended that the fragment will have at least about 30%, at least about 50%, at least about 70%, 80%, 90%, 95% or higher of the nematicidal and/or polyphenol oxidase activity of the reference protein.

Methods for measuring nematode resistance or nematicidal activity are described in, for example, U.S. Patent Publication Nos. 20050191714 and 20080153102, as well as in the Experimental Examples provided herein. Methods for measuring polyphenol oxidase activity include, for example, detecting the presence of o-quinone produced in an enzymatic reaction of the polyphenol oxidase on tyrosine. Polyphenol oxidase oxidizes tyrosine which, in turn, is oxidized to o-quinone. The latter is accompanied by an increase in absorbance at 280 nm. The rate of increase is proportional to enzyme concentration and is linear during a period of 5-10 minutes after an initial lag. One unit causes a change in absorbance at 280 nm of 0.001 per minute at 25° C., pH 6.5 under the specified conditions.

A fragment of a nucleotide sequence encoding a nematicidal protein that encodes a biologically active portion of a protein of the invention will encode at least about 15, 25, 30, 50, 75, 100, 125, 150, 175, 200, 250, 300, 350, 400, 450 contiguous amino acids, or up to the total number of amino acids present in a full-length nematicidal protein of the invention.

Preferred nematicidal proteins of the present invention are encoded by a nucleotide sequence sufficiently identical to the nucleotide sequence of SEQ ID NO:1, 2, 3, 6, 7, 10, 11, 12, 15, 16, 17, 19, 21, 45, or 46, or a nucleotide sequence encoding an amino acid sufficiently identical to SEQ ID NO:4, 5, 8, 9, 13, 14, 18, 20, 22, 47, 48, or 49. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (i.e., the sequence disclosed herein as any of SEQ ID NO:1-22, and 45-49). The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to the nucleic acid molecules of the invention. BLAST protein searches can be performed with the BLASTX program, score=50, wordlength=3, to obtain amino acid sequences homologous to protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A nonlimiting example of a software program useful for analysis of ClustalW alignments is GENEDOC™. GENEDOC™ (Karl Nicholas) allows assessment of amino acid (or DNA) similarity and identity between multiple proteins. Another nonlimiting example of a mathematical algorithm utilized for the comparison of sequences is the algorithm of Myers and Miller (1988)*CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the nematicidal protein encoding nucleotide sequences include those sequences that encode the nematicidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the nematicidal proteins disclosed in the present invention as discussed below. Variant proteins encompassed by the present invention are biologically active, that is they continue to possess the desired biological activity of the native protein, that is, polyphenol oxidase and/or nematicidal activity. By "retains activity" is intended that the variant will have at least about 30%, at least about 50%, at least about 70%, or at least about 80% of the nematicidal activity and/or the polyphenol oxidase activity of the reference protein. One of skill in the art will recognize that variants may have an increase or decrease in one activity (e.g., nematicidal or polyphenol oxidase) without affecting, or only minimally affecting, the other activity. For example, variants proteins may show improved nematicidal activity relative to the native protein without concomitant improvements in polyphenol oxidase activity and vice versa. Unless otherwise specified, variants proteins will have at least 30% of each activity relative to the native protein. Methods for measuring these activities are described elsewhere herein.

The skilled artisan will further appreciate that changes can be introduced by mutation of the nucleotide sequences of the invention thereby leading to changes in the amino acid sequence of the encoded nematicidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a nematicidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical between all proteins contained in the alignment in FIGS. 3 and 4). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment in FIGS. 3, 4, and 5). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer nematicidal activity to identify mutants that retain activity. Following mutagenesis, the encoded protein can be expressed recombinantly, and the activity of the protein can be determined using standard assay techniques.

Using methods such as PCR, hybridization, and the like corresponding nematicidal sequences can be identified, such sequences having substantial identity to the sequences of the invention. See, for example, Sambrook and Russell (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY). Alternatively, polyphenol oxidase sequences can be identified using any number of polyphenol oxidase sequences known in the art.

In a hybridization method, all or part of the nematicidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known nematicidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a nematicidal protein of the invention or a fragment or variant thereof. Methods for the preparation of probes for hybridization are generally known in the art and are disclosed in Sambrook and Russell, 2001, supra herein incorporated by reference.

For example, an entire nematicidal protein sequence disclosed herein, or one or more portions thereof, may be used as a probe capable of specifically hybridizing to corresponding nematicidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding nematicidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Nematicidal proteins are also encompassed within the present invention. By "nematicidal protein" is intended a protein having the amino acid sequence set forth in SEQ ID NO:5, 8, 14, 18, 20, 22, or 48. Fragments, biologically active portions, and variants thereof are also provided, and may be used to practice the methods of the present invention.

"Fragments" or "biologically active portions" include polypeptide fragments comprising amino acid sequences sufficiently identical to the amino acid sequence set forth in SEQ ID NO:4, 5, 8, 13, 14, 18, 20, 22, 47, 48, or 49, and that exhibit polyphenol oxidase and/or nematicidal activity. In some embodiments, the biologically active fragments exhibit both polyphenol oxidase and nematicidal activity. A biologically active portion of a nematicidal protein can be a polypeptide that is, for example, 10, 25, 50, 100, 150, 200, 250 or more amino acids in length. Such biologically active portions can be prepared by recombinant techniques and evaluated for nematicidal and/or polyphenol oxidase activity. Methods for measuring nematicidal activity and polyphenol oxidase activity are described elsewhere herein. As used herein, a fragment comprises at least 8 contiguous amino acids of SEQ ID NO:4, 5, 8, 13, 14, 18, 20, 22, 47, 48, or 49. The invention encompasses other fragments, however, such as any fragment in the protein greater than about 10, 20, 30, 50, 100, 150, 200, 250, or 300 contiguous amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of SEQ ID NO: 4, 5, 8, 13, 14, 18, 20, 22, 47, 48, or 49. Variants also include polypeptides encoded by a nucleic acid molecule that hybridizes to the nucleic acid molecule of SEQ ID NO:1, 2, 3, 6, 7, 10, 12, 15, 16, 17, 19, 21, 45, or 46, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining nematicidal activity and/or polyphenol oxidase activity. In some embodiments, the variants exhibit both polyphenol oxidase and nematicidal activity.

Bacterial genes, such as the some of the novel genes disclosed herein, quite often possess multiple methionine initiation codons in proximity to the start of the open reading frame. Often, translation initiation at one or more of these start codons will lead to generation of a functional protein. These start codons can include ATG codons. However, some bacteria also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may also lead to generation of nematicidal proteins. These nematicidal proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a nematicidal protein may be altered by various methods, and that these alterations may result in DNA sequences encoding proteins with amino acid sequences different than that encoded by a nematicidal protein of the present invention. This protein may be altered in various ways including amino acid substitutions, deletions, truncations, and insertions of one or more amino acids of SEQ ID NO:4, 5, 8, 9, 13, 14, 18, 20, 22, 47, 48, or 49, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a nematicidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired nematicidal activity. However, it is understood that the ability of a nematicidal protein to confer nematicidal activity may be improved by the use of such techniques upon the compositions of this invention. For example, one may express a nematicidal protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the nematicidal protein mutations in a non-mutagenic strain, and identify mutated genes with nematicidal activity, for example by performing an assay to test for nematicidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different nematicidal protein coding regions can be used to create a new nematicidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a nematicidal gene of the invention and other known nematicidal genes to obtain a new gene coding for a protein with an improved property of interest, such as an increased insecticidal activity. Strategies for such DNA shuffling are known in the art.

See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered nematicidal proteins. Domains may be swapped between nematicidal proteins, resulting in hybrid or chimeric toxins with improved nematicidal activity or target spectrum. Methods for generating recombinant proteins and testing them for nematicidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265: 20923-20930; Rang et al. 91999) *Appl. Environ. Microbiol.* 65:2918-2925).

Protease Cleavage Site Manipulation

In various embodiments of the present invention, a nucleotide sequence encoding a cleavage fragment of the full-length polyphenol oxidase is expressed in the host cell of interest. In other embodiments, the nucleotide sequences encoding the polyphenol oxidase sequences are modified to add or remove sequences encoding proteolytic cleavage sites. For example, some full-length polyphenol oxidases, such as AXN-1 and AXN-8, are inactive precursors, which require proteolytic truncation to yield a toxin that is activate against SCN. For instance, full-length AXN-8 expressed in *E. coli* is not active against SCN, but when it is treated with trypsin, a C-terminal portion of the protein is removed, yielding an active truncated protein. When AXN-8 was expressed in *E. coli* in the truncated form, SCN activity was not seen, suggesting that the entire sequence may be needed in order for the protein to fold properly when it is synthesized. Furthermore, while not being bound by any particular theory or mechanism, it is also possible that an active polyphenol oxidase may catalyze the production of compounds that could be toxic to the plant or to animals (other than the pest of interest, e.g., nematodes) that feed on the plant. Expression of a full-length inactive protein would prevent this from occurring until the enzyme is activated by proteolytic truncation. This activation would only occur when a nematode infects the plant, and only in the area where the nematode is located. Once the nematode is killed by the toxin, no further active polyphenol oxidase will be produced because no more proteases are being produced by the nematode.

If an inactive full-length protein is expressed in a plant for either of the reasons described above, then it must be proteolytically truncated in order to show toxicity against SCN or other plant-parasitic nematodes. It is possible that plant proteases will carry out the activation to at least some extent, but more complete activation could be achieved if proteases produced by the nematode are capable of truncating the protein. If it is desirable to have the polyphenol oxidase remain inactive until a nematode infects the plant (for example, as a way of preventing the catalysis of chemical reactions that might produce compounds toxic to the plant or to non-target organisms), then any truncation site naturally occurring in the protein that is capable of being cleaved by plant proteases can be mutated so that it will no longer be cleaved. In either case, the sequence of the polyphenol oxidase can be modified (or further modified) such that it contains a recognition site for nematode proteases at the appropriate truncation location. This location can be determined by sequence analysis of active toxin isolated from its natural source, or by sequence analysis of active toxin produced by treating the full-length protein with proteases capable of carrying out the truncation, such as trypsin in the case of AXN-8. The choice of the protease recognition site will depend on the proteases that are secreted by the nematode into the plant, or that are present within the nematode digestive system. This site can be determined by isolating proteases and determining their substrate specificity, or by sequencing genes from the nematode or from a cDNA library prepared from mRNA extracted from the nematode, and determining to which protease families the genes belong. A secreted protease will activate the toxin in the plant, while a protease in the nematode's digestive system would activate the toxin after it is ingested.

Esophageal gland cells from soybean cyst nematode have been shown to express a putative cysteine proteinase (Genbank accession AF345792). This proteinase falls into the Peptidase C13 family, which consists of asparaginyl cysteine endopeptidases (proteases that cleave specifically after asparagines residues). In one example of this invention, a polyphenol oxidase expressed in a transgenic plant could be rendered activatable by SCN by altering the sequence of the polyphenol oxidase such that it contains an asparagine residue at the truncation site that results in an active enzyme. While not bound by any particular theory or mechanism, this version of the polyphenol oxidase might give greater activity than the wild-type enzyme because it would be fully activated in the presence of SCN. Furthermore, it might remain inactive in the absence of SCN, thereby avoiding the accumulation of chemical products of reactions catalyzed by the enzyme. If a recognition site for plant proteases is present in the protein, it can be mutated so that only the nematode proteases are capable of carrying out the truncation. A similar approach can be taken for any target pest. The truncation site of the polyphenol oxidase can be modified so that it will be susceptible to truncation by proteases produced by the target pest.

Vectors

A polyphenol oxidase sequence of the invention (or any other polyphenol oxidase sequences known in the art) may be provided in an expression cassette for expression in a plant of interest. In various embodiments, the polyphenol oxidase sequence is selected from any polyphenol oxidase known in the art. In another embodiment, the polyphenol oxidase is selected from the polyphenol oxidase derived from *Trichoderma reesei, Bacillus thuringiensis, Glycine Max, Zea maize, Streptomyces castaneoglobisporus, Neurospora crassa* species.

By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Pesticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed with the organism. Alternatively, the additional gene(s) can be provided on multiple expression cassettes. In various embodiments, the invention encompasses host cells comprising the insert of the vectors. By "insert of the vectors" is intended the DNA sequence comprising the gene(s) of the invention that is integrated into the host cell genome.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest. The promoters may be constitutive or inducible, or may be functional only in certain plant parts. In various embodiments, the promoter is a root-specific promoter (e.g., FaRB7, Vaughan (2006) *J. Exp. Bot.* 57:3901-3910). In some embodiments, the promoter is a feeding site specific promoter (e.g., TobRB7, Opperman (1994) *Science* 263(5144) 221-223).

Such an expression cassette is provided with a plurality of restriction sites for insertion of the nematicidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the protein is targeted to the chloroplast for expression. In this manner, where the protein is not directly inserted into the chloroplast, the expression cassette will additionally contain a nucleic acid encoding a transit peptide to direct the protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. The methods comprise introducing at least one nucleotide sequence encoding a heterologous polyphenol oxidase enzyme into at least one plant cell. In various embodiments, the polyphenol oxidase is derived from a plant. In other embodiments, the polyphenol oxidase is derived from a non-plant organism (e.g., fungal, algal, bacterial, or other non-plant microorganism). The polyphenol oxidase may be a monophenol oxidase or a diphenol oxidase. In various embodiments, the polyphenol oxidase is selected from any of SEQ ID NO:1-22 or 45-49, or any of the polyphenol oxidases referenced in Table 13.

By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell. "Heterologous" refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. The polyphenol oxidase genes described herein may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the nematicidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (Agrobacterium-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Molecular and biochemical methods can then be used to confirm the presence of the integrated heterologous gene of interest into the genome of the transgenic plant. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for nematicidal activity. In another embodiment, the presence of the transgene is detected by testing for polyphenol oxidase activity.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}$P target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the nematicidal gene is then tested by hybridizing the filter to a radioactive probe derived from a nematicidal gene, by methods known in the art (Sambrook and Russell, 2001, supra).

Western blot, biochemical assays and the like may be carried out on the transgenic plants to confirm the presence of protein encoded by the nematicidal gene by standard procedures (Sambrook and Russell, 2001, supra) using antibodies that bind to one or more epitopes present on the nematicidal protein.

Methods for Screening for and Developing Plants with Polyphenol Oxidase Activity Various plant species are known to express polyphenol oxidase. In some instances, expression of polyphenol oxidase has been shown to be associated with improved agronomic performance. For example, plants which exhibit comparably high resistance to climatic stress have been shown to posses relatively higher polyphenol oxidase levels than susceptible varieties (Thipyapong et al. (2007) *Molecules* 12(8):1569-95). However, prior to the present invention, resistance to nematode infestation has not been demonstrated in plants having polyphenol oxidase activity. Identification of plants having optimal polyphenol oxidase levels provides a hitherto unrecognized opportunity for developing plants suitable for cultivation in an area susceptible to nematode infestation. By "optimal polyphenol oxidase activity" is intended a level of activity sufficient to bring about death to at least one pest, or to noticeably reduce pest growth, feeding, or normal physiological development when the plant expressing the polyphenol oxidase is exposed to a nematode pest.

Thus, provided herein are methods for screening a plant or plant variety for polyphenol oxidase activity. For example, root extracts from different plants (for example, different inbred lines, or different progeny of a cross) can be tested for polyphenol oxidase activity using assays known in the art and described elsewhere herein. Plants expressing polyphenol oxidase may be tested for nematicidal activity, and the plants showing optimal activity selected for use in a field susceptible to nematode infestation, or used for further breeding for introgression of the nematode-resistance trait into a plant population. Identification of a polyphenol oxidase having optimal activity may be associated with the presence of a polyphenol oxidase, the relative level of expression or activity of a polyphenol oxidase, or the presence of a particular polymorphism associated with improved polyphenol oxidase activity and/or nematode resistance. The polymorphism may be within the polyphenol oxidase gene itself, or may be within a genetic marker identified as being associated with or linked to polyphenol oxidase expression (i.e., within a Quantitative Trait Loci (QTL) associated with polyphenol oxidase expression).

The methods of the invention further contemplate screening of existing QTLs for nematode resistance for the presence of a polyphenol oxidase gene or polymorphism. Previous studies have identified large genetic regions linked as QTLs involved in nematode resistance, and these regions may contain certain polyphenol oxidases or tyrosinases. QTLs typically contain many hundreds if not thousands of genes, yet identification of the causal gene for the associated trait often remains elusive. Thus, the invention anticipates screening for polyphenol oxidase genes (or particular polymorphisms thereof) from such regions. These genetic elements, or genetic markers closely linked to these polyphenol oxidase genetic elements, can be used in marker-assisted breeding protocols to develop plants more resistant to nematode infestation. Methods for screening a genetic region for a gene of interest are routine in the art, as are methods for marker-assisted breeding.

Germplasm Mutagenesis

Further provided are methods for developing plants with nematode resistance using germplasm mutagenesis. Mutagenesis is means of creating genetic diversity that does not exist or has not been found in existing germplasm. Treating somatic embryos, embryos derived from culturing portions of immature seeds, with mutagenic agents can be an efficient method of creating mutations because they are easier to regenerate into whole plants than cell cultures and easier to handle in large numbers than seeds. Thus, the methods encompassed herein comprise mutagenizing a plant germplasm and screening a component of the plant derived therefrom (for example, root extracts) for polyphenol oxidase activity. Isolates having optimal polyphenol oxidase activity can be used to develop a plant population suitable for cultivation in an area susceptible to nematode infestation.

Methods for germplasm mutagenesis are generally known in the art. Gamma rays are the most frequently used mutagen, but new agents including ion beams and space condition have also been used in mutation induction and breeding (Chen et al. (2006) *Plant Mutation Reports* Volume 1 Number 1 at www-naweb.iaea.org/nafa/pbg/public/pmr-01-01.pdf). Use of in vitro cultures for mutation induction, or use of another culture to rapidly produce homozygous lines from irradiated progenies, has proven to be very useful in several laboratories.

Methods for Controlling Nematodes in a Field

Provided herein are methods for controlling nematodes in a field susceptible to infestation by one or more plant-parasitic nematode pests. The methods comprise cultivating a plant in an area susceptible to plant-parasitic nematode infestation, wherein the plant expresses a heterologous polyphenol oxidase. An "area" or a "field" susceptible to infestation includes a geographic region or planting area that has a detectable level of one or more species of plant-parasitic nematodes. A "detectable level" includes any level of plant-parasitic nematodes sufficiently high enough to cause damage in a susceptible plant. Signs of nematode damage include stunting and yellowing of leaves, and wilting of the plants during hot periods. However, some nematodes, including soybean cyst nematode (SCN), can cause significant yield loss without obvious above-ground symptoms. In this instance, roots infected with plant-parasitic nematodes will be dwarfed or stunted compared to the roots of a plant not infected with nematodes. Various other macroscopic and microscopic detection methods of different types of nematodes are known in the art, and are typically available via local agricultural extension services. An area susceptible to nematode infestation may also include an area that has a detectable level of plant-parasitic nematodes in the soil.

Use in Pesticidal Control

General methods for employing strains comprising a nucleotide sequence of the present invention, or a variant thereof, in pest control or in engineering other organisms as pesticidal agents are known in the art. See, for example U.S. Pat. No. 5,039,523 and EP 0480762A2.

The bacterial or fungal strains containing the nucleotide sequence(s) of the present invention, or a variant thereof, or the microorganisms that have been genetically altered to contain a nematicidal gene and protein may be used for protecting agricultural crops and products from pests. In one aspect of the invention, whole, i.e., unlysed, cells of a toxin-producing organism are treated with reagents that prolong the activity of the toxin produced in the cell when the cell is applied to the environment of target pest(s).

Alternatively, the pesticide is produced by introducing a nematicidal gene into a cellular host. Expression of the nematicidal gene results, directly or indirectly, in the intracellular production and maintenance of the nematode toxin. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, root, seed and/or foliage of plants. See, for example EPA 0192319, and the references cited therein. In various embodiments, the polyphenol oxidase may be expressed in a bacterial cell and used as a probiotic to treat the seed of the plant. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. The compounds can be cofactors or other molecules that enhance the activity of the polyphenol oxidase enzyme. For example, the compound can be methyl jasmonate, which has been shown to increase the expression of polyphenol oxidase genes (see, for example, Constable and Ryan (1998) *Plant Mol. Biol.* 36(1):55-62), a phenol such as L-DOPA or tyrosine, or a substrate capable of participating in polyphenol oxidase-mediated crosslinking (e.g., tyrosine). These compounds can be provided to the plants before, during, or after (or any combination thereof) application of the pesticidal composition. Where the compound is a polypeptide capable of expression in a plant, the susceptible plant may be transgenic for this polypeptide.

These compounds can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the nematicidal formulation.

Methods of applying an active ingredient of the present invention or an agrochemical composition of the present invention that contains at least one of the nematicidal proteins of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such nematicidal polypeptide, the polypeptide may be present in a concentration of from about 1% to about 99% by weight.

Nematode pests may be killed or reduced in numbers in a given area by the methods of the invention, or may be prophylactically applied to an environmental area to prevent infestation by a susceptible pest (i.e., nematode). Preferably the pest ingests, or is contacted with, a nematicidally-effective amount of the polypeptide. By "nematicidally-effective amount" is intended an amount of the pesticide that is able to bring about death to at least one pest, or to noticeably reduce pest growth, feeding, or normal physiological development. This amount will vary depending on such factors as, for example, the specific nematode species to be controlled, the specific environment, location, plant, crop, or agricultural site to be treated, the environmental conditions, and the method, rate, concentration, stability, and quantity of application of the nematicidally-effective polypeptide composition. The formulations may also vary with respect to climatic conditions, environmental considerations, and/or frequency of application and/or severity of pest infestation.

The nematicidal compositions described may be made by formulating either the microbial cell (or extract thereof) expressing the nematicidal gene of the invention, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the nematicidal composition with suitable adjuvants using conventional formulation techniques. Suitable formulations and application methods are described in U.S. Pat. No. 6,468,523, herein incorporated by reference.

In various embodiments, the polyphenol oxidase can be used to treat or prevent the infestation of plants with insects, fungi, bacteria, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachimidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus* leucopterus, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Frankliniella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus* leucopterus, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus* leucopterus, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Methods for Increasing Plant Yield

Methods for increasing plant yield are provided. The methods comprise introducing into a plant or plant cell a polynucleotide comprising a nematicidal sequence disclosed herein. Expression of the nematicidal sequence results in improved resistance to nematode infestation which, in turn, increases the yield of a transgenic plant compared to the yield of a plant not expressing a polyphenol oxidase (when exposed to plant-parasitic nematodes). As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the nematicidal sequence.

Methods for Identifying Quantitative Trait Loci Associated with Nematode Resistance Also provided herein are methods for identifying or validating markers associated with a quantitative trait loci (QTL) for nematode resistance or tolerance. The methods comprise evaluating genetic markers within the genomic region surrounding one or more polyphenol oxidase genes in a population of plants showing resistance or tolerance to nematode infestation, and detecting an association between one or more genetic marker(s) and the nematode resistance trait. High density genetic maps have been developed for many species of plants susceptible to nematode infestation, including maize and soybean plants. Markers from these maps can be evaluated for the association, and positively-associated markers can be used in downstream applications such as marker-assisted breeding. Methods for evaluating marker:trait associations are known in the art and can be applied to genomic regions encoding genes having homology to polyphenol oxidase genes.

In another embodiment, QTLs that are known or suspected to be associated with nematode resistance can be evaluated to determine whether a polyphenol oxidase gene is within or near the QTL. In this embodiment, regions within or surrounding the QTL can be sequenced and searched for polyphenol oxidase homologs.

The following examples are offered by way of illustration and not by way of limitation.

EXPERIMENTAL

Example 1

Assay for Nematicidal Activity

Use of biogenic amines to induce feeding and/or movement from parasitic nematodes has been demonstrated previously for RNAi uptake experiments (for example, see P. E. Urwin, Catherine J. Lilley, and Howard J. Atkinson, "Ingestion of Double-Stranded RNA by Preparasitic Juvenile Cyst Nematodes Leads to RNA Interference" Molecular Plant Microbe Interaction Vol. 15, No. 8, 2002, pp. 747-752. Also see M J Kimber, S McKinney, S. McMaster T A Day, C C Flemming and A G Maule (2007) "Flp gene disruption in a parasitic nematode reveals motor dysfunction and unusual neuronal sensitivity to RNA interference" The FASEB Journal vol 21 pp 1233-1242)

Assays of SCN activity provided herein are based on use of an SCN bioassay that typically contains ~200 J2 nematodes (hatched within 2 days of assay) per well in a 96-well half-area plate. The nematodes are incubated in 20 mM Tris buffer (pH 8.0) containing 50 mM octopamine, and the following antibiotic and antifungal components: gentamycin (1.5 ug/ul), nystatin (0.05 ug/ul), Sigma antibiotic-antimycotic (cat # A5955) at 1×, Infuse antimycotic (1/1500 dilution from stock) all in 30 ul final volume, including the test strain or protein. The assay plate is incubated at 28 C in a humidified chamber. Scoring of the assay is facilitated by addition of sodium carbonate, which causes living nematodes to curl, while dead nematodes remain straight and rigid. Scoring must be done within ~10 minutes of the carbonate addition. Activity on nematodes is scored on the following scale, and compared with negative control, and positive control samples.

TABLE 1

Scoring Convention for SCN Assays
SCN Scoring Convention

| Score assigned | Mortality on SCN (%) |
|---|---|
| 0 | 0-10% |
| 1 | 11-20% |
| 2 | 21-50% |
| 3 | 51-75% |
| 4 | 76-95% |
| 5 | 96-100% |

Example 2

Enhancement of Steady-State Levels of Nematode Protein Toxins in Microbial Strains A microbial strain of interest (e.g., a bacteria or fungal strain) is grown under media conditions that can partially limit the availability of nutrients to the microbe. For instance, the availability of carbon or nitrogen can be reduced in the minimal growth medium.

The medium is supplemented with components that are useful to stimulate microbial production of nematode toxins. As one example, the addition of gelatin to a growth medium can mimic the gelatinous cuticle found on some nematodes, and thus stimulate the microbial production of nematode protein toxins. As another example, the addition of nematodes to the growth medium (such as $C.$ elegans or soybean cyst nematode) can stimulate the microbial production of protein toxins. As another example, a nematode extract can be prepared and added to a microbial growth medium to stimulate the production of microbial protein toxins. The various components can also be combined.

The growth medium (supplemented with a component to stimulate toxin production) is inoculated with a microbial strain or strains, and then grown under conditions appropriate for strain growth. Whole culture or some fraction of the culture (for example: culture supernatants, protein extracts, solubilized protein extracts, pellet extracts, etc) are then tested to determine if a nematode toxin has been produced by the microbial strain under the growth medium and growth conditions tested.

Example 3

Identification of Nematode Protein Toxin from Arthrobotrys oligospora

It is known in the art that nematicidal fungi can be isolated from soil, in particular from suppressive soils. Several such fungi were obtained and tested for SCN activity, under a variety of growth conditions.

Arthrobotrys oligospora is a nematophagous fungus, and has been observed previously to have nematicidal activity in soil. This activity has been associated with nematophagous trapping in the literature (for example, see Nansen et al., 1988. Vet Parasitol., 26:329-37). There is no description of nematode protein toxins production by Arthrobotrys oligospora or related strains.

To test the ability of an Arthrobotrys oligospora strain to produce protein toxins, an Arthrobotrys oligospora strain (ATX21995) was inoculated into Arthrobotrys medium supplemented as shown below, and incubated at 30° C. with gentle shaking for 7 days. The resulting extracts were tested for ability to kill SCN.

Arthrobotrys medium (per liter):
  1 g glucose
  0.5 g $(NH_4)_2SO_4$
  0.5 g $MgSO_4$
  2 g KH2PO4
  0.005 g $FeSO_4$
  Adjust to pH 6.0 with KOH
Optional:
  0.5 g gelatin
  Add C. elegans harvested from 1 MYOB plate (100 mm plate, first inoculated with E. coli to generate a lawn as diet for C. elegans) per 50 mL of medium

TABLE 2

Activity of ATX 21995 grown in various media

| Media | Description | Activity of ATX 21995 extract |
|---|---|---|
| Media 1 | Potato dextrose broth | No/Low activity |
| Media 2 | *Arthrobotrys* medium | No/Low Activity |
| Media 3 | *Arthrobotrys* medium + gelatin | Inconsistent Activity |
| Media 4 | *Arthrobotrys* medium + gelatin + nematodes | Consistent, Strong Activity |

From each culture medium, a soluble protein extract was prepared following seven days of growth. At that time, the fungal biomass was separated from the growth medium using a disposable 0.4 micron filter unit, and this biomass was then ground in a mortar and pestle in the presence of liquid nitrogen to lyse the cells. This material was then resuspended in buffer A (50 mM Tris (pH 8.0), 1 mM DTT) and submitted for soybean cyst nematode (SCN) bioassays.

Protein extracts were prepared from *Arthrobotrys oligospora* (ATX21995) cultures grown in *Arthrobotrys* medium (+gelatin, +*C. elegans*) for seven days. Extracts were prepared by grinding the fungal biomass in the presence of liquid nitrogen (as described above) and resuspending the lysed cell material in buffer at pH 6.0 (50 mM MES, 1 mM DTT), pH 8.0 (50 mM Tris, 1 mM DTT) or pH 10.4 (50 mM CAPS, 1 mM DTT). Extracts prepared in this manner assayed for SCN activity all showed strong activity on SCN.

Example 4

Purification of AXN-1 from ATX21995

Purifications were carried out using extracts prepared from ATX 21995 grown in *Arthrobotrys* Medium contain gelatin and nematodes. Typically, purifications were carried out at large scale by growing several 250 mL flasks (approximately 30-60 flasks) with 50 mL of medium in each flask to allow sufficient quantities of protein to enter the purifications.

Two different protein purifications were carried out from cultures of strain ATX21995. The total fungal biomass from these cultures was lysed (mortar and pestle with liquid nitrogen), and the protein was fractionated by FPLC using standard purification methods. These purifications resulted in identification of an ~50 kDa protein that correlated with the elution of the SCN activity.

Example 5

Protein Characterization of 50 kDa Protein from ATX21995

To clone the gene encoding the ~50 kDa protein, approximately 10-15 micrograms of this protein was isolated, and a small quantity of the sample was electroblotted to a PVDF membrane by standard methods, stained the membrane with Coomassie dye, and the band corresponding to the 50 kDa protein excised and subjected to N-terminal sequencing as known in the art. This protein was found to yield very small amounts of free amino acids during the sequencing reactions, which suggested that the N-terminus of the protein might be chemically modified.

A gel slice containing the 50 kDa protein was digested in-gel with trypsin, and the fragments were then separated by HPLC. Individual peaks were then analyzed by MALDI to identify fragments suitable for protein sequencing. A total of 5 tryptic fragments were selected, and subjected to Edman degradation for protein sequencing (Table 3). Edman degradation sequencing reactions yielded the following sequences for each of these peaks:

TABLE 3

N-terminal sequence of tryptic fragments

| Peak Name | Primary Sequence Identified by Edman Degradation | SEQ ID NO: |
|---|---|---|
| 20 | G-T-W-S-I-A-A-G-S-R | 23 |
| 24 | D-S-T-G-E-F-N-A-T-L-Y-R | 24 |
| 29 | S-A-P-Y-A-I-T-G-I | 25 |
| 36 | Y-P-D-A-W-F-N-A-Q-S-A-Q-L-R | 26 |
| 42 | F-G-S-S-Y-P-E-L-Q-P | 27 |

Example 6

Cloning of a cDNA that Encodes the 50 kDa Protein from ATX21995

Total RNA was isolated from ATX21995 cultures grown for 2 days, 4 days and 6 days. This RNA was reverse transcribed to generate cDNA; this cDNA was subsequently normalized to decrease the abundance of strongly expressed transcripts. Using this cDNA as a starting template, several PCR products were generated and sequenced.

Degenerate PCR based use of cDNA linker sequence. A number of degenerate oligonucleotides based on the amino acid sequence of 24 (see Table 3) were designed and tested in combination with the oligonucleotides that represent the ends of the cDNA pool. A set of conditions was identified that resulted in amplification of an 1840 nucleotide PCR product. This PCR product, as well as several other candidate PCR products, was cloned into a TOPO vector, and the DNA sequences adjacent to the vector were determined.

Degenerate PCR based solely on amino acid sequence. Degenerate PCR primers were designed based on the amino acid sequences of fragments 20, 24, and 29, 36, and 42 from Table 3. This set of degenerate oligonucleotides utilized inosine in several positions to reduce the degeneracy of the resulting oligonucleotides. Also, when possible, a set of nested degenerate PCR primers was designed for each amino acid sequence in Table 3. This strategy allows use of the "outside" primers (those based on the more N-terminal amino acids of a sequence in Table 3) in the first round of PCR, and a second "nested" set of primers (based on amino acids slightly C-terminal, but overlapping the amino acids utilized for the "outside" primers).

A matrix of PCR reactions using these degenerate oligonucleotides lead to the cloning and sequencing of several amplification products, which showed DNA homology and overlap with the 1840 nucleotide clone isolated previously, and together comprised a complete cDNA open reading frame; suggesting that all of these partial cDNAs originated from a single gene.

Cloning of axn-1 cDNA, and determination of the genomic sequence. Based on the DNA sequences of several partial cDNA sequences, PCR primers were designed to repeatedly amplify and sequence the cDNA coding region. Several independent cDNAs were cloned and completely sequenced. In some cases, individual cDNA clones contained small unspliced introns, consistent with alternate splicing of the hRNA produced from this gene. For example, two variants of the 5' untranslated region (UTR) were recovered. These variants are identical for 42nt upstream of the start site (and including the region encoding the N-terminus of the encoded protein); however they then diverge for another 60-80 nt upstream; this is likely to presence of an alternately spliced or unspliced intron in the 5' UTR of one of the cDNAs.

PCR primers from the cDNA were used to amplify and sequence eight independent genomic clones from the region encoding the cDNA. The sequence from this genomic region matches the cDNA sequence exactly over the length of the cDNA. Thus, the DNA sequence of the multiple genomic and full cDNA clones confirms the structure of the cDNA, and its genomic organization.

This gene encoding the cDNA is designated herein as axn-1, and the encoded full length protein is designated as AXN-1. The sequence of the axn-1 cDNA is set forth in SEQ ID NO:2, and the open reading frame is provided as SEQ ID NO:3; the sequence of the AXN-1 full length protein is provided as SEQ ID NO:4. The full-length chromosomal sequence for axn-1 is set forth in SEQ ID NO:1. The truncated amino acid sequence is set forth in SEQ ID NO:5. A synthetic DNA sequence encoding the full-length AXN-1 amino acid sequence is set forth in SEQ ID NO:6.

In addition to the 5'UTR variants, it is interesting to note that many cDNAs isolated by these experiments have internal modifications relative to the sequences described herein. For example, many clones appear to be internally deleted relative to the full-length sequence, and others clearly contain unspliced introns. So, it is likely that this gene, designated herein as axn-1, is subject to alternate mRNA processing including alternate mRNA splicing. These alternate mRNAs are likely to be minor components of the steady-state axn-1 mRNA, and the cDNA normalization process utilized in the cloning of these cDNA has likely increased the relative proportion of these variants to the fully spliced full-length transcript.

Example 7

AXN-1 is Homologous to Monophenol Oxidases

An alignment of AXN-1 to other polyphenol oxidase sequences is provided in FIG. 3, and the percent sequence identity of AXN-1 to these sequences is provided in Table 4.

Another interesting observation was that a section of the protein encoded by this cDNA contained many repeated amino acids, especially glutamine (Q), and did not show homology to polyphenol oxidases or tyrosinases in databases searches.

TABLE 4

Amino Acid Identity of AXN-1 to other fungal proteins

| Organism/Protein | Percent Identity to AXN-1 |
| --- | --- |
| Neurospora_crassa | 17% |
| Pyrenophora_tritici | 15% |
| Podospora_anserina | 20% |
| Lentinula_edodes | 17% |
| Pycnoporus_sanguineus | 19% |
| Pholio_nameko | 18% |
| Tuber_melanosporum | 16% |
| Asp_fum_tyrosinase | 14% |

Example 8

Nematode Toxin from Strain ATX20514

Bacterial strain ATX20514 was identified from empirical screening of strains, based on strong toxicity of cultures towards soybean cyst nematode (SCN) in the standard bioassay format.

ATX 20514 was grown in C2 medium in 96-well blocks for 3 days at 30° C. Next, the cells in each well were lyzed with a bead beater, and the lysed cell extract was fed to soybean cyst nematodes (J2 stage) in the presence of a feeding stimulant (octopamine). Five days after incubation, the toxicity towards SCN was scored on the scale of 0 to 5 as shown in Table 1.

The soluble fraction prepared from ATX20514 in this manner scored as a "5" when 5 µL of this extract was incorporated into the SCN bioassay.

A protein extract was prepared from strain ATX20514 by growing the strain in 50 mL of C2 medium at 30° C. for 3 days. At that time, cells in the culture were lysed by bead beater treatment, and the crude lysate was centrifuged at 18,000×g for 15 minutes to pellet the cell debris and insoluble proteins. The soluble protein extract was recovered as the supernatant fraction, and then filtered, and this material was then subjected to multiple treatments followed by testing in an SCN bioassay.

Heat. An aliquot of the protein extract (100 µL) was heated at 100° C. for 30 minutes, and tested in an SCN bioassay. A negative control sample was mock treated alongside, and likewise tested in SCN bioassay.

Protease. An aliquot of the protein extract (95 µL) was proteolytically digested with 5 µL of Pronase (1 mg/mL final) (Roche) for 3 hours at 37° C.

Dialysis. An aliquot of the protein extract (100 µL) was dialyzed against either 20 mM Tris, pH 8.0, ("Buffer A") or 50 mM sodium phosphate, 150 mM NaCl, pH 7.0.

Filtration. An aliquot of the protein extract (500 µL) was placed above a spin filter membrane with a 3000 molecular weight cutoff (Millipore) and centrifuged at 12,000×g until approximately 400 µL, of the total volume had passed through the filter unit. Additional protein extract was then added above the spin filter membrane, and the centrifuge step was repeated until approximately 400 µL, of the total volume had again passed through the filter unit.

The results of the SCN bioassays are shown in Table 5. These results support the conclusion that the SCN activity in strain ATX20514 is due to a protein active against SCN.

TABLE 5

Characterization of ATX20514 activity

| Sample | SCN Score |
| --- | --- |
| Heat Treatment | |
| ATX 20514 extract | 5 |
| ATX 20514 extract heat treated | 0 |
| Protease Treatment | |
| Protease Treatment | |
| Protease treated | 0 |
| Control; protease only, no extract | 0 |
| Dialysis | |
| Dialyzed vs 20 mM Tris, pH 8.0 | 5 |
| 20 mM Tris, pH 8.0 | 0 |

TABLE 5-continued

Characterization of ATX20514 activity

| Sample | SCN Score |
|---|---|
| ATX20514 extract dialyzed 50 mM sodium phosphate, 150 mM NaCl, pH 7.0 | 5 |
| 50 mM sodium phosphate, 150 mM NaCl, pH 7.0 Size exclusion filtration | 0 |
| ATX20514 extract retentate from spin dialysis | 5 |
| ATX20514, filtrate from spin dialysis | 0 |

Example 9

Purification of a Nematode Protein Toxin from ATX20514

A four-column purification was carried out, leading to the identification of a 52 kDa protein band that correlated with SCN toxicity.

ATX20514 was grown in 2 liters of C2 medium at 30° C. for 3 days. The culture was centrifuged, and the pellet was resuspended in 100 mL of 50 mM Tris (pH 8.0). The cell pellet was then lysed using a French press, centrifuged at 18,000×g for 15 minutes, and the supernatant fraction (i.e., the soluble protein extract) was forwarded into ammonium sulfate precipitation, dialysis, and column chromatography purification.

After 3 steps of column chromatography, the active fractions were dialyzed against 50 mM Tris (pH 8.0), 1 mM DTT; (“Buffer A”), loaded onto a Mono Q anion exchange column (1 mL; GE Healthcare) and washed with the same buffer. Elution was carried out with a 40 column volume gradient from 0 M to 0.2 M NaCl in Buffer A. Individual fractions were submitted for SCN bioassays, and fractions 21 through 24 were found to possess the strongest SCN toxicity. A protein of approximately 52 kDa correlated well with the SCN toxicity in these fractions.

Example 10

N-terminal Sequence of the 52 kDa Protein from ATX20514

Individual purification fractions enriched for the 52 kDa protein were separated by gel electrophoresis, transferred to PVDF, and stained with Coomassie Blue. The section of the membrane containing the 52 kDa protein was excised and subjected to N-terminal sequencing. The resulting N-terminal sequence was compiled using the amino acid corresponding to the biggest peak at each position on the chromatograms.

Example 11

Purification and N-terminal Sequence of 31 kDa Protein from ATX20514

In addition to the activity that correlated with the 52 kDa protein, a second active peak having SCN activity was eluted from a cation exchange column. These active fractions were subsequently loaded onto an anion exchange column to further purify the activity. Thus, a 31 kDa protein was identified that correlated with this SCN activity:

To further characterize the 31 kDa protein, N-terminal sequencing was performed. This analysis allowed us to compare the N-terminal protein sequence of the 52 kDa protein to that of the 31 kDa protein. We found the two amino acid sequences to be very similar, suggesting that the 31 kDa protein is a truncation of the 52 kDa protein:

TABLE 6

| N-terminal sequences of ATX 20514 toxins | | |
|---|---|---|
| Protein Size | Primary Sequence Identified by Edman Degradation | SEQ ID NO: |
| 52 kDa | STSRQDVAKLGPGWNKVLLNYALAMQALDE | 28 |
| 31 kDa | STSGQDVAKLGPQWNKVLLNYALAMQALDE | 29 |

Example 12

Cloning of axn-8 from ATX20514

Using the N-terminal sequence data from the 52 kDa and 31 kDa toxins, the gene encoding these proteins was cloned in several steps by a degenerate PCR and Tail strategies as known in the art, leading to the amplification of an approximately 5 kb fragment from multiple rounds of TAIL PCR. This region contains an open reading frame encoding an amino acid protein. Herein we designate this gene as axn-8 and the corresponding protein as AXN-8. The N-terminus of the predicted AXN-8 protein matches well to the amino acid sequences of the 52 kDa and 31 kDa proteins. Furthermore, the DNA sequence downstream of axn-8 contains a second open reading frame that is likely to be co-expressed with axn-8 in an operon. The DNA sequence containing regulatory elements is set forth in SEQ ID NO:11. The open reading frame for axn-8 is set forth in SEQ ID NO:12, and encodes SEQ ID NO:13. The predicted truncated protein is set forth in SEQ ID NO:14. The metal binding integral membrane protein encoded by the downstream ORF is set forth in SEQ ID NO:41. It is recognized that the truncation site may be at least about 1, at least about 2, at least about 3, 4, 5, 6, 7, 8, 9, or 10 amino acids in either direction of the arginine at position 295 of SEQ ID NO:13. A synthetic DNA sequence encoding SEQ ID NO:13 is set forth in SEQ ID NO:15.

Example 13

Homology of AXN-8 to Monophenol Oxidases

A BLAST analysis of AXN-8 shows that it shares homology with known bacterial monophenol oxidases. This class of enzymes also includes tyrosinases.

TABLE 7

| Closest homologs of AXN-8 | | | | |
|---|---|---|---|---|
| Enzyme | Source | GENBANK Accession# | % Homology | E Score |
| Tyrosinase | *Delftia acidovorans* | YP_001562639 | 55% | 7e−92 |
| Tyrosinase | *Ruegeria pomeroyi* | YP_166646 | 54% | 6e−86 |
| Tyrosinase | *Burkholderia thailandensis* | ZP_02466656 | 52% | 6e−79 |
| Monophenol oxidase | *Agrobacterium vitis* | YP_002549739 | 50% | 2e−71 |

TABLE 7-continued

Closest homologs of AXN-8

| Enzyme | Source | GENBANK Accession# | % Homology | E Score |
|---|---|---|---|---|
| Tyrosinase | *Rhizobium etli* | ZP_03501998 | 47% | 2e−60 |
| Tyrosinase | *Dyadobacter fermentans* | ZP_03898981 | 44% | 1e−56 |

An alignment of AXN-8 with tyrosinase enzymes (FIG. 4) reveals that it possesses sequence motifs that are consistent with these tyrosinases, including the presence of histidine residues that are likely to be necessary for binding of copper ions by the enzyme.

Example 14

Dose Response of AXN-8 Activity

A sample of AXN-8 protein was used to assess the effect of different protein amounts on SCN. This sample was diluted in nematode assay buffer, and assays were set up to establish final AXN-8 protein concentrations up to 25 µg/ml. Nematodes were incubated, and results scored after five days. Scores are the average of two to four replicates.

TABLE 8

Dose Response of AXN-8

| [AXN-8] in Assay (µg/ml) | SCN Score |
|---|---|
| 25 | 4.7 |
| 12.5 | 4 |
| 6.25 | 2.7 |
| 3.125 | 1.7 |
| 1.6 | 0.75 |
| 0.8 | 1 |
| 0.4 | 1 |
| 0 | 1 |

Example 15

Cloning of AXN-2 from *Bacillus thuringiensis* Strain ATX25028

Independently of the purification of AXN-1 and AXN-8, SCN activity was observed from several *Bacillus* strains. The discovery that both AXN-1 and AXN-8 encode proteins with homology to oxidase/tyrosinase suggested that perhaps the activity in these *Bacillus* strains was also due to oxidase/tyrosinase like activity.

ATX25028 DNA was prepared as described previously, and DNA sequence of plasmid preparations was obtained.

Analysis of the partial DNA sequences obtained from ATX25028 DNA demonstrated existence of a gene encoding an oxidase/tyrosinase-like enzyme in this strain. The DNA sequence was utilized to design PCR primers, and the open reading frame of the full gene was amplified by PCR from genomic DNA or ATX 25028. This gene is referred to herein as axn-2 (SEQ ID NO:7), and its encoded protein as AXN-2 (SEQ ID NO:8). Clone pAX5530 contains axn-2 inserted into a modified pRSF-1b vector (Novagen) as a BamHI-AscI fragment to generate a his-tag containing protein (SEQ ID NO:9). pAX5531 contains axn-2 inserted into a modified pRSF-1b vector as a PstI-AscI fragment such that the expressed protein lacks a His-tag. Lysates derived from *E. coli* cells expressing AXN-2 protein were generated and tested for activity on SCN. Clones both containing and lacking an N-terminal His tag exhibited strong activity on SCN.

A synthetic gene encoding AXN-2 is set forth in SEQ ID NO:10.

TABLE 9

| Activity of AXN-2 clones on SCN | | | |
|---|---|---|---|
| Clone | Protein | Sample description | SCN score |
| Neg control | Neg control | Unlysed culture | 0 |
| Neg control | Neg control | Lysed culture | 0 |
| Neg control | Neg control | Tris extract concentrated 4X | 0 |
| pAX5531 | AXN-2 | Unlysed culture | 5 |
| pAX5531 | AXN-2 | Lysed culture | 4 |
| pAX5531 | AXN-2 | Tris extract concentrated 4X | 5 |
| pAX5530 | AXN-2 5'His tag | Unlysed culture | 5 |
| pAX5530 | AXN-2 5'His tag | Lysed culture | 5 |
| pAX5530 | AXN-2 5'His tag | Tris extract concentrated 4X | 5 |
| — | — | LB kan media control | 0 |
| — | — | Tris Buffer buffer control | 0 |

Example 16

Cloning of a Polyphenol Oxidase from the Nematode Active Strain ATX26455

ATX26455 was identified as a strain exhibiting strong activity in a soybean cyst nematode (SCN) assay. ATX 26455 was grown in a C2 medium in 96-well blocks for 3 days at 30° C. Cells were then lysed, and the lysed cell extract was fed to soybean cyst nematodes (J2 stage) as described herein. Five days after incubation, the toxicity towards SCN was scored as described herein. Such an assay using 5 µL of lysed extract prepared from ATX26455 was assigned a score of "5," denoting 96-100% mortality of this extract on SCN.

Preliminary Biochemical Screening of ATX26455

A protein extract was prepared from strain ATX26455 by growing the strain in C2 medium at 30° C. for 3 days. A soluble protein extract was prepared from the culture and subjected to the following biochemical characterizations, followed by assay for activity on SCN:

- Heat treatment. An aliquot of the protein extract was heat-treated to destroy protein activity, and then tested in an SCN bioassay. A negative control sample was mock treated alongside the heat treated sample, and likewise tested in an SCN bioassay.
- Protease treatment. An aliquot of the protein extract was proteolytically digested with a protease (such as Pronase) and then tested in an SCN bioassay. Negative controls without protease were also tested in an SCN bioassay.
- Dialysis treatment. An aliquot of the protein extract was dialyzed to allow small molecules to be removed from the extract, and then tested in an SCN bioassay.
- Filtration testing. An aliquot of the protein extract was placed above a spin filter membrane with a 3000 molecular weight cutoff and then centrifuged to pass the extract through the filter unit. The retentate and the filtrate were then tested in an SCN bioassay.

The results of the SCN bioassays carried out on each of the preliminary biochemical samples are shown in Table 10. These results suggest that the nematode toxin produced by ATX26455 is conferred by a protein.

TABLE 10

Activity Tests of ATX 26455 Fractions

| Sample | SCN Bioassay Score |
|---|---|
| Heat Treatment | |
| Extract | 5 |
| Extract, heat treated | 0 |
| Protease Treatment | |
| Extract, protease treated | 0 |
| Protease only (negative control) | 0 |
| Dialysis Treatment | |
| Extract, dialyzed | 2 |
| Dialysis control | 0 |
| Filtration Testing | |
| Filter, retained by filter | 4 |
| Filter, flow through | 0 |

Purification of Nematode Protein Toxin from ATX26455

Cells were lysed using a French press, and the lysate was centrifuged, and the supernatant collected, resulting in a clarified lysate. The clarified lysate was highly active in an SCN bioassay. The activity in this clarified lysate was confirmed to be sensitive to protease digestion. The clarified lysate was further enriched by the following ammonium sulfate precipitation steps.

First, the clarified lysate was brought to 13% saturation with ammonium sulfate, centrifuged, and the pellet discarded. This procedure was repeated at 25% saturation with ammonium sulfate. Finally, the supernatant was brought to 50% saturation with ammonium sulfate, and after centrifugation, the pellet was recovered and resuspended in buffer, and subjected to dialysis to remove the residual ammonium sulfate. The resuspended pellet was then fractionated on an anion exchange column, and the fractions that showed activity in SCN bioassay were collected and pooled. The pooled active fractions were further fractionated on a hydrophobic interaction column. This resulted in the identification of a protein band migrating at location corresponding to a protein of approximately 35 kDa. This protein (referred to herein as the "35 kDa protein") correlated well with the SCN toxicity observed during each step of the purification, and that was highly enriched during the purification process.

Characterization of the 35 kDa Protein from ATX26455

The sequence of the N-terminal amino acids of a protein of interest from ATX 26455 was determined by Edman degradation as known in the art. A protein fraction containing the protein of interest was separated by gel electrophoresis, and the proteins in the resulting gel were transferred to a PVDF membrane. The membrane was then stained with Coomassie Blue, and the section of the membrane containing the 35 kDa protein was excised, and subjected to N-terminal sequencing. The N-terminal sequence of this protein was determined by this method to be as follows:

N-Terminal Sequence of Protein from Active Fractions of ATX26455

```
                                           (SEQ ID NO: 42)
M-N-T-I-R-Q-D-V-A-T-L-G-S-G-W-D-N-K-V-L-L-N-Y-A-L-

A-M-R-E-L-D-K-L-P-I-T-N.
```

Interestingly, this protein sequence revealed sequence similarities with the AXN-8 protein described herein, suggesting that the activity of ATX 26455 is in fact, also due to activity of a homologous, but novel, polyphenol oxidase.

Cloning of Nematode Active Toxin Gene from ATX26455

The N-terminal protein sequence of the putative toxin was utilized to a degenerate oligonucleotide primer corresponding to this sequence. The sequence of that primer is shown here (using the nomenclature established by the International Union of Pure and Applied Chemistry):

```
                                           (SEQ ID NO: 43)
5' CAR GAY GTI GCI ACI YTI GGI CCI GGI TGG 3'
```

To generate a degenerate oligonucleotide to amplify the reverse strand of the toxin gene, the DNA sequence of the axn-8 gene was utilized as a template, resulting in generation of a series of degenerate oligonucleotide primers for testing on ATX26455. One PCR primer designed by this approach is shown here:

```
                                           (SEQ ID NO: 44)
5' RTG RTG IAG CCA RAA IAT IGG RTC 3'
```

PCR reactions using the degenerate primers (SEQ ID NO:43 and 44) resulted in amplification and sequencing of a 711 nucleotide PCR product. This 711 nt PCR fragment was confirmed to originate from the DNA region encoding the 35 kDa protein.

The DNA sequence of the 711 nucleotide PCR product was utilized to isolate the entire region coding for the 35 kDa protein by thermal interlaced (TAIL) PCR methods known in the art. This approach allowed assembly of the sequence of the complete open reading frame encoding the 35 kDa protein. The axn-9 open reading frame was amplified by PCR from ATX 26455 and cloned into a modified prsf1b cloning vector. The insert of the resulting clone (pAX5597) was sequenced and found to be identical to the sequence obtained by TAIL.

The sequence of the DNA fragment is provided as SEQ ID NO:45. The open reading frame contained within this DNA region is designated as axn-9 (SEQ ID NO:46), and its corresponding protein as AXN-9 (SEQ ID NO:47). The predicted truncated protein corresponds to residue 314 of SEQ ID NO:47. It is recognized that the truncation site may be at least about 1, at least about 2, at least about 3, 4, 5, 6, 7, 8, 9, or 10 amino acids in either direction of the lysine at position 314 of SEQ ID NO:47.

Inspection of the DNA sequence of the axn-9 open reading frame shows that there is a GTG codon present at nucleotides 22-24 of axn-9. Given the proximity of this codon to the ATG start site, and the tendency for some bacterial open reading frames to tolerate multiple translational start sites, it is possible that translation from this GTG codon occurs in nature, and that the resulting protein has similar properties to the full length AXN-9 protein. Thus, this protein is also provided herein as SEQ ID NO:48 and designated AXN-9 (GTG).

Example 17

Homology of AXN-9 to AXN-8 and Other Polyphenol Oxidase Proteins

ANX-9 is homologous to the AXN-8 protein disclosed herein. AXN-9 is 68% identical to AXN-8. An alignment of AXN-9 with AXN-8 is provided as FIG. 5. Given that AXN-8 is known to be truncated, and also given that most polyphenol oxidases are proteolytically processed, and given the homology between AXN-8 and AXN-9, we can predict that AXN-9 is likely to be similarly truncated by proteolysis.

Example 18

Protease-Activated AXN-9 Protein is Active in SCN Bioassay

The bacterial AXN-9 expression vector described above (pAX5597) was transformed into BL21*DE3 cells (Invitrogen). Following IPTG induction, the whole cell culture was centrifuged. The resulting pellet was resuspended in $\frac{1}{10}^{th}$ volume of buffer (50 mM Tris (pH 8.0), 10 µM CuSO4) and then lysed by sonication. The lysate was split into 2 aliquots, and 1 aliquot was treated with freshly prepared trypsin (0.1 mg/mL of lysate) for 2 hours at 37° C. AXN-9 protein treated with trypsin showed strong activity on SCN, while untreated AXN-9 protein did not show activity on SCN (Table 11).

TABLE 11

Activity of AXN-9 clones on SCN

| Clone | Sample description | SCN score |
|---|---|---|
| Neg control | Buffer (50 mM Tris (pH 8.0), 10 µM CuSO4) | 0 |
| Neg control | Buffer + Trypsin | 0 |
| Pos control | Buffer + Mushroom Tyrosinase | 4 |
| pAX5597 | AXN-9 protein, untreated | 0 |
| pAX5597 | AXN-9 protein, trypsin-treated | 5 |

Example 19

Activity of Mushroom Tyrosinase on SCN

Given the discovery of activity of AXN-1, AXN-8, AXN-9, and AXN-2 on SCN and the homology of AXN-1, AXN-8, AXN-9, and AXN-2 to polyphenol oxidase/tyrosinase enzymes, previously identified tyrosinase enzymes were tested for this property.

Mushroom tyrosinase (Sigma T3824) was resuspended in buffer to yield a concentrated solution. Dilutions of this solution were test on SCN as described above, and the following assay results were obtained. Though not directly stated by the provider of this enzyme, the enzyme contained in this "Mushroom tyrosinase" is likely to have been derived from the white mushroom.

TABLE 12

Titration of mushroom tyrosinase activity

| [protein] in Assay (µg/ml) | Mushroom tyrosinase |
|---|---|
| 50 | 4 |
| 25 | 3.3 |
| 12.5 | 3 |
| 6.25 | 2.7 |
| 3.125 | 2.7 |
| 1.6 | 2 |
| 0.8 | 1 |
| 0 | 1 |

The mushroom tyrosinase preparation obtained is demonstrated to have activity on SCN; at approximately the same relative concentration of enzyme relative to the tested amounts of AXN-1 and AXN-8.

Example 20

Possibilities of Other Polyphenol Oxidases Having SCN Activity

Given the discovery of anti-SCN activity from both fungal and bacterial proteins that have homology to polyphenol oxidases, and the observation of activity from mushroom tyrosinase, it is understood that many known polyphenol oxidases/tyrosinases are likely to have such activity when tested as described herein; for example, in an SCN bioassay containing J2 juveniles, 20 mM Tris, and 50 mM octopamine for 3-7 days at about 20° C., with shaking in a rotary incubator, contained in a plate such as a 96-well plate.

For example, Selinheimo et at describe characterization of fungal and plant tyrosinases, and demonstrate substrate and activity differences between these broad classes of enzymes, including the mushroom tyrosinase (fluka) which is likely the same enzyme described in Example 19 above. Table 2 of Selinheimo et al shows that such enzymes can have different substrate specificities toward mono- and polyphenolic compounds. In general it is understood that the plant enzyme, such as the apple and potato enzymes of the Selinheimo et al. study, have less activity on monophenol substrates such as tyrosine than fungal or bacterial enzymes. Furthermore, FIG. 3 and the text of Selinheimo et al describe that certain enzymes have the ability to cross-link a representative protein (casein). In the cited study, each of the enzymes is capable of crosslinking casein, but the enzymes differ in the amount of enzyme required of crosslinking. Further, all but one of these enzymes seemed to have a strong preference and/or requirement for a monophenol or diphenol in the reaction in order to achieve crosslinking. The notable exception to this requirement is the enzyme from *T. reesei*.

The *T. reesei* enzyme (set forth in SEQ ID NO:21 and 22 herein) exhibits substrate and activity parameters that distinguish it from the other tested enzymes. Notably, the *T. reesei* enzyme showed the most efficient crosslinking of casein at the lower of the two enzyme concentrations tested. Furthermore, and in contrast to the other tested enzymes, *T. reesei* had strong activity in the absence of a monophenol or diphenol in the reaction; although the addition of such compounds appeared to increase the amount of such crosslinking. The other enzymes tested appear to require a monophenol or diphenol for such crosslinking activity. Selinheimo et al provides further evidence for this property of the *T. reesei* enzyme in additional references (Selinheimo et al. (2008) J Agric Food Chem. 56(9):3118-28 and Selinheimo et al. (2007) J Agric Food Chem. 55(15):6357-65), each of which is herein incorporated by reference in its entirety.

For example, the cDNA with GENBANK accession number AK246031 from *Glycine max* (SEQ ID NO:16 and 17, encoding SEQ ID NO:18; Umezawa et al (2008) *DNA Res.* 15(6):333-46) exhibits characteristic homologies of plant phenol oxidases.

By way further of example, the cDNA with GENBANK accession number AM418385 (SEQ ID NO:19) encoding a *T. reesei* enzyme (SEQ ID NO:20) with homology to polyphenol oxidases, (Selinheimo et al. (2006) *FEBS Lett.* 273, 4322-4335) is provided as an example of a polyphenol oxidase that given the inventions herein is likely to exhibit activity upon SCN.

Other sequences (according to GENBANK accession numbers) having homology to the sequences disclosed herein are encompassed by the present invention. An exemplary (but non-limiting) list is set forth in Table 13.

TABLE 13

| GENBANK Accession Numbers of Polyphenol oxidase homologs | | | |
|---|---|---|---|
| AB005228.1 | AB188749.1 | AB277357.1 | AF078789.2 |
| AB010101.1 | AB188750.1 | AB277358.1 | AF136926.2 |
| AB011827.1 | AB188751.1 | AB277359.1 | AF183578.1 |
| AB011828.1 | AB188752.1 | AB280948.1 | AF183583.1 |
| AB011829.1 | AB188753.1 | AB280949.1 | AF183588.1 |
| AB011830.1 | AB188754.1 | AB280950.1 | AF183593.1 |
| AB011831.1 | AB188755.1 | AB353113.1 | AF183599.1 |
| AB018244.1 | AB188756.1 | AB430855.1 | AF183604.1 |
| AB022095.1 | AB188757.1 | AB430856.1 | AF183609.1 |
| AB023291.1 | AB188758.1 | AC007607.6 | AF183614.1 |
| AB024278.1 | AB188759.1 | AC007861.5 | AF183619.1 |
| AB024279.1 | AB188760.1 | AC025271.7 | AF183624.1 |
| AB024280.1 | AB188761.1 | AC084064.6 | AF183629.1 |
| AB024281.1 | AB188762.1 | AC084197.1 | AF183634.1 |
| AB027512.1 | AB188763.1 | AC084321.37 | AF183639.1 |
| AB032694.1 | AB188764.1 | AC084628.1 | AF183644.1 |
| AB032695.1 | AB188765.1 | AC090416.1 | AF183649.1 |
| AB032696.1 | AB188766.1 | AC115007.6 | AF183654.1 |
| AB032697.1 | AB188767.1 | AC116734.14 | AF183659.1 |
| AB033993.1 | AB188768.1 | AC119816.5 | AF183664.1 |
| AB038994.1 | AB188769.1 | AC122194.4 | AF183669.1 |
| AB044884.1 | AB207236.1 | AC122517.2 | AF183674.1 |
| AB052940.1 | AB207237.1 | AC138173.2 | AF183679.1 |
| AB056680.1 | AB214954.1 | AC138230.5 | AF183684.1 |
| AB060689.1 | AB215107.1 | AC157507.2 | AF187155.1 |
| AB070938.1 | AB215108.1 | AC157710.2 | AF216388.1 |
| AB070939.1 | AB223612.1 | AC163891.2 | AF237792.1 |
| AB081466.1 | AB224151.1 | AC166548.2 | AF237794.1 |
| AB107880.1 | AB225958.1 | AC182653.2 | AF237797.1 |
| AB107881.1 | AB238605.1 | AC185364.2 | AF237799.1 |
| AB108529.1 | AB254132.1 | AC208369.1 | AF237802.1 |
| AB108530.1 | AB254133.1 | AC210555.1 | AF237804.1 |
| AB108531.1 | AB259663.1 | AC214595.1 | AF237807.1 |
| AB120567.1 | AB275646.1 | AC215650.1 | AF237809.1 |
| AB178936.1 | AB275647.1 | AC216911.1 | AF249161.1 |
| AB178937.1 | AB277347.1 | AC217034.1 | AF249162.1 |
| AB178938.1 | AB277348.1 | AC232778.1 | AF249163.1 |
| AB178939.1 | AB277349.1 | AE016825.1 | AF249164.1 |
| AB178940.1 | AB277350.1 | AE017195.1 | AF249165.1 |
| AB188743.1 | AB277351.1 | AF001295.1 | AF249166.1 |
| AB188744.1 | AB277352.1 | AF020548.1 | AF249167.1 |
| AB188745.1 | AB277353.1 | AF020786.1 | AF249168.1 |
| AB188746.1 | AB277354.1 | AF039165.1 | AF249169.1 |
| AB188747.1 | AB277355.1 | AF064803.1 | AF249170.1 |
| AB188748.1 | AB277356.1 | AF076781.1 | AF249171.2 |
| AF249172.1 | AJ006097.1 | AK191107.1 | AK209365.1 |
| AF249173.1 | AJ012048.1 | AK191149.1 | AK209447.1 |
| AF249174.1 | AJ223816.1 | AK191393.1 | AK209840.1 |
| AF249175.1 | AJ245880.1 | AK192283.1 | AK209886.1 |
| AF249176.1 | AJ248285.1 | AK192618.1 | AK209941.1 |
| AF249177.1 | AJ250302.1 | AK192643.1 | AK210502.1 |
| AF249178.1 | AJ252741.1 | AK192803.1 | AK210623.1 |
| AF249179.1 | AJ293806.1 | AK192857.1 | AK212036.1 |
| AF249180.1 | AJ297474.1 | AK193779.1 | AK212309.1 |
| AF249181.1 | AJ297475.1 | AK193825.1 | AK212393.1 |
| AF249182.1 | AJ309175.1 | AK195046.1 | AK212795.1 |
| AF249183.1 | AJ309176.1 | AK195075.1 | AK213314.1 |
| AF249184.1 | AJ334488.1 | AK195088.1 | AK213631.1 |
| AF249185.1 | AJ547813.1 | AK195144.1 | AK213730.1 |
| AF249186.1 | AJ556169.1 | AK195566.1 | AK214235.1 |
| AF249187.1 | AJ564729.1 | AK195805.1 | AK215621.1 |
| AF249188.1 | AJ574915.1 | AK196684.1 | AK216615.1 |
| AF249189.1 | AJ619741.1 | AK197855.1 | AK216621.1 |
| AF249190.1 | AJ635323.1 | AK198477.1 | AK216757.1 |
| AF249191.1 | AJ697805.1 | AK198785.1 | AK217145.1 |
| AF252540.1 | AJ698339.1 | AK199363.1 | AK217194.1 |
| AF255610.1 | AJ698340.1 | AK199676.1 | AK217421.1 |
| AF261957.1 | AJ698341.1 | AK201739.1 | AK217687.1 |
| AF261958.1 | AJ698342.1 | AK201880.1 | AK217984.1 |
| AF263611.1 | AJ786639.1 | AK201909.1 | AK218840.1 |
| AF269192.1 | AJ786640.1 | AK202339.1 | AK219113.1 |
| AF280808.1 | AJ845083.2 | AK202954.1 | AK219854.1 |
| AF338426.3 | AK014619.1 | AK202956.1 | AK219958.1 |
| AF343911.2 | AK027025.1 | AK204044.1 | AK219983.1 |
| AF350261.1 | AK027863.1 | AK204101.1 | AK220030.1 |
| AF359360.3 | AK033040.1 | AK204148.1 | AK241303.1 |
| AF359361.3 | AK108237.1 | AK205161.1 | AK246031.1 |
| AF363027.1 | AK115853.1 | AK205196.1 | AK247107.1 |

TABLE 13-continued

GENBANK Accession Numbers of Polyphenol oxidase homologs

| | | | |
|---|---|---|---|
| AF368291.1 | AK115906.1 | AK205614.1 | AK247126.1 |
| AF380300.1 | AK116290.1 | AK206598.1 | AK247410.1 |
| AF391288.1 | AK148172.1 | AK206970.1 | AK293115.1 |
| AF395447.2 | AK148332.1 | AK207020.1 | AK297887.1 |
| AF397401.1 | AK148341.1 | AK207203.1 | AL138753.8 |
| AF397402.1 | AK148357.1 | AK207218.1 | AL139318.9 |
| AF400250.1 | AK148370.1 | AK207451.1 | AL591688.1 |
| AF401231.1 | AK148432.1 | AK207965.1 | AL606526.10 |
| AF445638.2 | AK148441.1 | AK208194.1 | AL606645.2 |
| AF473807.2 | AK177534.1 | AK208432.1 | AL646052.1 |
| AF507945.1 | AK190354.1 | AK208651.1 | AL670884.7 |
| AJ000503.1 | AK191069.1 | AK208819.1 | AL731611.2 |
| AL731637.2 | AY149460.1 | AY333979.1 | AY812904.1 |
| AL939108.1 | AY149880.1 | AY333982.1 | AY815264.1 |
| AL939113.1 | AY149881.1 | AY333984.1 | AY822711.1 |
| AL954747.1 | AY149882.1 | AY333985.1 | AY837842.1 |
| AM418385.1 | AY162287.1 | AY338251.1 | AY842859.1 |
| AM420293.1 | AY236224.1 | AY341747.1 | AY844019.1 |
| AM424232.2 | AY254101.1 | AY341748.1 | AY844020.1 |
| AM440949.2 | AY266330.1 | AY341749.1 | AY844021.1 |
| AM442013.1 | AY274808.1 | AY341750.1 | AY844022.1 |
| AM448108.2 | AY279540.1 | AY341751.1 | AY844023.1 |
| AM451548.2 | AY283062.1 | AY341752.1 | AY844024.1 |
| AM467012.2 | AY322334.1 | AY341753.1 | AY844025.1 |
| AM478512.2 | AY322335.1 | AY341754.1 | AY844026.1 |
| AM502246.1 | AY322336.1 | AY341755.1 | AY844027.1 |
| AM746676.1 | AY322337.1 | AY341756.1 | AY844028.1 |
| AM774403.1 | AY322338.1 | AY341757.1 | AY844029.1 |
| AM920430.1 | AY322339.1 | AY341758.1 | AY844030.1 |
| AM920435.1 | AY322340.1 | AY341759.1 | AY844031.1 |
| AM920436.1 | AY322341.1 | AY341760.1 | AY844032.1 |
| AM920437.1 | AY322342.1 | AY341761.1 | AY844033.1 |
| AM949571.1 | AY322343.1 | AY341762.1 | AY844034.1 |
| AM949572.1 | AY322344.1 | AY341763.1 | AY844035.1 |
| AM949573.1 | AY322345.1 | AY341764.1 | AY844036.1 |
| AM949574.1 | AY322346.1 | AY341765.1 | AY844037.1 |
| AM949575.1 | AY322347.1 | AY370019.1 | AY844038.1 |
| AM949576.1 | AY322348.1 | AY451324.1 | AY844039.1 |
| AP000720.4 | AY322349.1 | AY515506.1 | AY844040.1 |
| AP003280.2 | AY322350.1 | AY526904.1 | AY844041.1 |
| AP003290.2 | AY322351.1 | AY596266.1 | AY844042.1 |
| AP008207.1 | AY322352.1 | AY596267.1 | AY844043.1 |
| AP008210.1 | AY322353.1 | AY596268.1 | AY844044.1 |
| AP009294.1 | AY322354.1 | AY596269.1 | AY844045.1 |
| AP009493.1 | AY322355.1 | AY596270.1 | AY844046.1 |
| AP009632.1 | AY322356.1 | AY659975.1 | AY844047.1 |
| AY017302.1 | AY322357.1 | AY665681.1 | AY844048.1 |
| AY017303.1 | AY322358.1 | AY665682.1 | AY844049.1 |
| AY017304.1 | AY322359.1 | AY675348.1 | AY844050.1 |
| AY046527.2 | AY322360.1 | AY743343.1 | AY844051.1 |
| AY052751.3 | AY322361.1 | AY743344.1 | AY844052.1 |
| AY052787.2 | AY322362.1 | AY743345.1 | AY844053.1 |
| AY072037.1 | AY322363.1 | AY751301.1 | AY844054.1 |
| AY072038.1 | AY327520.1 | AY787659.1 | AY844055.1 |
| AY075039.1 | AY333967.1 | AY804220.1 | AY844056.1 |
| AY103683.1 | AY333970.1 | AY804228.1 | AY844057.1 |
| AY123973.1 | AY333975.1 | AY804236.1 | AY844058.1 |
| AY844059.1 | AY844104.1 | AY844149.1 | AY849378.1 |
| AY844060.1 | AY844105.1 | AY844150.1 | AY865623.2 |
| AY844061.1 | AY844106.1 | AY844151.1 | AY865624.1 |
| AY844062.1 | AY844107.1 | AY844152.1 | AY866432.1 |
| AY844063.1 | AY844108.1 | AY844153.1 | AY874457.1 |
| AY844064.1 | AY844109.1 | AY844154.1 | AY874458.1 |
| AY844065.1 | AY844110.1 | AY844155.1 | AY874460.1 |
| AY844066.1 | AY844111.1 | AY844156.1 | AY874462.1 |
| AY844067.1 | AY844112.1 | AY844157.1 | AY874465.1 |
| AY844068.1 | AY844113.1 | AY844158.1 | AY874467.1 |
| AY844069.1 | AY844114.1 | AY844159.1 | AY904721.1 |
| AY844070.1 | AY844115.1 | AY844160.1 | AY959314.1 |
| AY844071.1 | AY844116.1 | AY844161.1 | AY959316.1 |
| AY844072.1 | AY844117.1 | AY844162.1 | AY965743.1 |
| AY844073.1 | AY844118.1 | AY844163.1 | AY965744.1 |
| AY844074.1 | AY844119.1 | AY844164.1 | AY965745.1 |
| AY844075.1 | AY844120.1 | AY844165.1 | AY965746.1 |
| AY844076.1 | AY844121.1 | AY844166.1 | AY971012.1 |
| AY844077.1 | AY844122.1 | AY844167.1 | BA000030.3 |
| AY844078.1 | AY844123.1 | AY844168.1 | BA000035.2 |
| AY844079.1 | AY844124.1 | AY844169.1 | BC021799.1 |

TABLE 13-continued

GENBANK Accession Numbers of Polyphenol oxidase homologs

| | | | |
|---|---|---|---|
| AY844080.1 | AY844125.1 | AY844170.1 | BC027179.1 |
| AY844081.1 | AY844126.1 | AY844171.1 | BC028311.1 |
| AY844082.1 | AY844127.1 | AY844172.1 | BC052608.1 |
| AY844083.1 | AY844128.1 | AY844173.1 | BC067064.1 |
| AY844084.1 | AY844129.1 | AY844174.1 | BC073623.1 |
| AY844085.1 | AY844130.1 | AY844175.1 | BC076406.1 |
| AY844086.1 | AY844131.1 | AY844176.1 | BC079678.1 |
| AY844087.1 | AY844132.1 | AY844177.1 | BC082330.1 |
| AY844088.1 | AY844133.1 | AY844178.1 | BC097647.1 |
| AY844089.1 | AY844134.1 | AY844179.1 | BC106678.1 |
| AY844090.1 | AY844135.1 | AY844180.1 | BC118918.1 |
| AY844091.1 | AY844136.1 | AY844181.1 | BC118919.1 |
| AY844092.1 | AY844137.1 | AY844182.1 | BC129260.1 |
| AY844093.1 | AY844138.1 | AY844183.1 | BC135907.1 |
| AY844094.1 | AY844139.1 | AY844184.1 | BC155086.1 |
| AY844095.1 | AY844140.1 | AY844185.1 | BC160742.1 |
| AY844096.1 | AY844141.1 | AY844186.1 | BC164222.1 |
| AY844097.1 | AY844142.1 | AY844187.1 | BT009357.1 |
| AY844098.1 | AY844143.1 | AY844188.1 | BT013158.1 |
| AY844099.1 | AY844144.1 | AY844189.1 | BT027443.1 |
| AY844100.1 | AY844145.1 | AY844190.1 | BT031730.1 |
| AY844101.1 | AY844146.1 | AY844191.1 | BT031775.1 |
| AY844102.1 | AY844147.1 | AY844192.1 | BX295539.1 |
| AY844103.1 | AY844148.1 | AY844193.1 | BX571966.1 |
| BX842680.1 | CR555306.1 | DQ058416.1 | DQ282930.1 |
| BX901913.8 | CR788249.6 | DQ060504.1 | DQ282931.1 |
| BX950229.1 | CR931725.6 | DQ060505.1 | DQ282932.1 |
| CP000031.1 | CR931761.6 | DQ060506.1 | DQ282933.1 |
| CP000085.1 | CT025512.2 | DQ060507.1 | DQ282934.1 |
| CP000094.1 | CT573213.2 | DQ060508.1 | DQ282935.1 |
| CP000103.1 | CU222605.1 | DQ060509.1 | DQ282936.1 |
| CP000112.1 | CU223051.1 | DQ060510.1 | DQ282937.1 |
| CP000115.1 | CU223259.1 | DQ100014.1 | DQ282938.1 |
| CP000125.1 | CU231766.1 | DQ100027.1 | DQ282939.1 |
| CP000150.1 | CU233197.1 | DQ112679.1 | DQ282941.1 |
| CP000155.1 | CU329671.1 | DQ123805.1 | DQ282942.1 |
| CP000249.1 | CU349019.1 | DQ123806.1 | DQ282943.1 |
| CP000250.1 | CU354092.1 | DQ217371.1 | DQ282944.1 |
| CP000282.1 | CU356179.1 | DQ282898.1 | DQ282945.1 |
| CP000319.1 | CU357691.1 | DQ282899.1 | DQ282946.1 |
| CP000325.1 | CU358302.1 | DQ282900.1 | DQ282947.1 |
| CP000386.1 | CU359628.1 | DQ282901.1 | DQ282948.1 |
| CP000388.1 | CU360132.1 | DQ282902.1 | DQ282949.1 |
| CP000472.1 | CU360325.1 | DQ282903.1 | DQ282950.1 |
| CP000491.1 | CU360391.1 | DQ282904.1 | DQ282951.1 |
| CP000502.1 | CU364068.1 | DQ282905.1 | DQ282952.1 |
| CP000542.1 | CU364414.1 | DQ282906.1 | DQ282953.1 |
| CP000571.1 | CU365186.1 | DQ282907.1 | DQ282954.1 |
| CP000573.1 | CU366348.1 | DQ282908.1 | DQ282955.1 |
| CP000593.1 | CU366591.1 | DQ282910.1 | DQ282956.1 |
| CP000673.1 | CU633872.1 | DQ282911.1 | DQ282957.1 |
| CP000678.1 | CU688450.1 | DQ282912.1 | DQ282958.1 |
| CP000740.1 | CU688451.1 | DQ282913.1 | DQ282959.1 |
| CP000741.1 | CU694472.5 | DQ282914.1 | DQ282960.1 |
| CP000820.1 | D00131.1 | DQ282915.1 | DQ282961.1 |
| CP000839.1 | D00439.1 | DQ282916.1 | DQ282962.1 |
| CP000854.1 | D00440.1 | DQ282917.1 | DQ282963.1 |
| CP000884.1 | D12514.1 | DQ282918.1 | DQ282964.1 |
| CP000926.1 | D17547.1 | DQ282919.1 | DQ282965.1 |
| CP000930.2 | D29686.1 | DQ282920.1 | DQ282966.1 |
| CP000937.1 | D37779.1 | DQ282921.1 | DQ282967.1 |
| CP000943.1 | D37929.1 | DQ282922.1 | DQ282968.1 |
| CP001037.1 | D45385.1 | DQ282923.1 | DQ282969.1 |
| CP001044.1 | D45386.1 | DQ282924.1 | DQ282970.1 |
| CP001191.1 | D63948.1 | DQ282925.1 | DQ282971.1 |
| CR293496.1 | D63949.1 | DQ282926.1 | DQ282972.1 |
| CR387935.16 | D63950.1 | DQ282927.1 | DQ282973.1 |
| CR388132.9 | D87669.1 | DQ282928.1 | DQ282974.1 |
| CR407683.1 | D87670.1 | DQ282929.1 | DQ282975.1 |
| DQ282976.1 | DQ283021.1 | DQ347167.1 | DQ360052.1 |
| DQ282977.1 | DQ283022.1 | DQ347168.1 | DQ360053.1 |
| DQ282978.1 | DQ283023.1 | DQ347169.1 | DQ360054.1 |
| DQ282979.1 | DQ283024.1 | DQ347170.1 | DQ360055.1 |
| DQ282980.1 | DQ283025.1 | DQ347171.1 | DQ360056.1 |
| DQ282981.1 | DQ283026.1 | DQ347172.1 | DQ360057.1 |
| DQ282982.1 | DQ283027.1 | DQ347173.1 | DQ360058.1 |
| DQ282983.1 | DQ283028.1 | DQ347174.1 | DQ360059.1 |
| DQ282984.1 | DQ283029.1 | DQ347175.1 | DQ360060.1 |

TABLE 13-continued

GENBANK Accession Numbers of Polyphenol oxidase homologs

| | | | |
|---|---|---|---|
| DQ282985.1 | DQ307747.1 | DQ347176.1 | DQ360061.1 |
| DQ282986.1 | DQ307748.1 | DQ347177.1 | DQ360062.1 |
| DQ282987.1 | DQ307749.1 | DQ347178.1 | DQ360063.1 |
| DQ282988.1 | DQ347130.1 | DQ347179.1 | DQ360064.1 |
| DQ282989.1 | DQ347131.1 | DQ347180.1 | DQ360065.1 |
| DQ282990.1 | DQ347132.1 | DQ347181.1 | DQ360066.1 |
| DQ282991.1 | DQ347133.1 | DQ347182.1 | DQ360067.1 |
| DQ282992.1 | DQ347134.1 | DQ347183.1 | DQ360068.1 |
| DQ282993.1 | DQ347138.1 | DQ347184.1 | DQ388569.1 |
| DQ282994.1 | DQ347139.1 | DQ347185.1 | DQ388570.1 |
| DQ282995.1 | DQ347140.1 | DQ347187.1 | DQ408547.1 |
| DQ282996.1 | DQ347141.1 | DQ347189.1 | DQ408550.1 |
| DQ282997.1 | DQ347142.1 | DQ347190.1 | DQ408551.1 |
| DQ282998.1 | DQ347144.1 | DQ347191.1 | DQ458272.1 |
| DQ282999.1 | DQ347145.1 | DQ347192.1 | DQ458273.1 |
| DQ283000.1 | DQ347146.1 | DQ347193.1 | DQ458274.1 |
| DQ283001.1 | DQ347147.1 | DQ347194.1 | DQ458275.1 |
| DQ283002.1 | DQ347148.1 | DQ347195.1 | DQ458276.1 |
| DQ283003.1 | DQ347149.1 | DQ347196.1 | DQ458277.1 |
| DQ283004.1 | DQ347150.1 | DQ347197.1 | DQ458278.1 |
| DQ283005.1 | DQ347151.1 | DQ347198.1 | DQ458279.1 |
| DQ283006.1 | DQ347152.1 | DQ356947.1 | DQ458280.1 |
| DQ283007.1 | DQ347153.1 | DQ360038.1 | DQ458281.1 |
| DQ283008.1 | DQ347154.1 | DQ360039.1 | DQ458283.1 |
| DQ283009.1 | DQ347155.1 | DQ360040.1 | DQ458284.1 |
| DQ283010.1 | DQ347156.1 | DQ360041.1 | DQ458285.1 |
| DQ283011.1 | DQ347157.1 | DQ360042.1 | DQ458286.1 |
| DQ283012.1 | DQ347158.1 | DQ360043.1 | DQ503140.1 |
| DQ283013.1 | DQ347159.1 | DQ360044.1 | DQ503141.1 |
| DQ283014.1 | DQ347160.1 | DQ360045.1 | DQ503142.1 |
| DQ283015.1 | DQ347161.1 | DQ360046.1 | DQ503143.1 |
| DQ283016.1 | DQ347162.1 | DQ360047.1 | DQ503144.1 |
| DQ283017.1 | DQ347163.1 | DQ360048.1 | DQ503145.1 |
| DQ283018.1 | DQ347164.1 | DQ360049.1 | DQ503146.1 |
| DQ283019.1 | DQ347165.1 | DQ360050.1 | DQ503147.1 |
| DQ283020.1 | DQ347166.1 | DQ360051.1 | DQ503148.1 |
| DQ503149.1 | DQ532390.1 | DQ851196.1 | DQ889705.1 |
| DQ503150.1 | DQ532391.1 | DQ851197.1 | DQ889706.1 |
| DQ503151.1 | DQ532392.1 | DQ851198.1 | DQ889707.1 |
| DQ503152.1 | DQ532393.1 | DQ851199.1 | DQ889708.1 |
| DQ503153.1 | DQ532394.1 | DQ851200.1 | DQ889709.1 |
| DQ503154.1 | DQ532395.1 | DQ851201.1 | DQ889710.1 |
| DQ503155.1 | DQ532396.1 | DQ851202.1 | DQ891466.2 |
| DQ503156.1 | DQ532397.1 | DQ851203.1 | DQ894649.2 |
| DQ503157.1 | DQ532398.1 | DQ851204.1 | DQ902581.1 |
| DQ503158.1 | DQ532399.1 | DQ851205.1 | DQ990911.1 |
| DQ503159.1 | DQ532400.1 | DQ851206.1 | DQ992481.1 |
| DQ503160.1 | DQ532401.1 | DQ851207.1 | DQ992482.1 |
| DQ503161.1 | DQ532402.1 | DQ851208.1 | DQ992483.1 |
| DQ503162.1 | DQ532403.1 | DQ851209.1 | EF070147.1 |
| DQ503163.1 | DQ532404.1 | DQ851210.1 | EF070148.1 |
| DQ503164.1 | DQ532405.1 | DQ851211.1 | EF070149.1 |
| DQ503165.1 | DQ532406.1 | DQ851212.1 | EF070150.1 |
| DQ503166.1 | DQ532407.1 | DQ851213.1 | EF102109.1 |
| DQ503167.1 | DQ532408.1 | DQ851214.1 | EF102110.1 |
| DQ503168.1 | DQ532409.1 | DQ851215.1 | EF102111.1 |
| DQ503169.1 | DQ532410.1 | DQ851216.1 | EF102112.1 |
| DQ503170.1 | DQ532411.1 | DQ851217.1 | EF158427.1 |
| DQ503171.1 | DQ532412.1 | DQ851218.1 | EF158428.1 |
| DQ503172.1 | DQ532413.1 | DQ851219.1 | EF183483.1 |
| DQ503173.1 | DQ532414.1 | DQ851220.1 | EF183484.1 |
| DQ503174.1 | DQ532415.1 | DQ851221.1 | EF363553.1 |
| DQ513312.1 | DQ532416.1 | DQ851222.1 | EF364134.1 |
| DQ513313.1 | DQ532417.1 | DQ851223.1 | EF364135.1 |
| DQ530058.1 | DQ532418.1 | DQ889677.1 | EF364136.1 |
| DQ530059.1 | DQ532419.1 | DQ889678.1 | EF364137.1 |
| DQ532375.1 | DQ532420.1 | DQ889690.1 | EF364138.1 |
| DQ532376.1 | DQ532421.1 | DQ889691.1 | EF364139.1 |
| DQ532377.1 | DQ532422.1 | DQ889692.1 | EF364140.1 |
| DQ532378.1 | DQ532423.1 | DQ889693.1 | EF364141.1 |
| DQ532379.1 | DQ532424.1 | DQ889694.1 | EF364142.1 |
| DQ532380.1 | DQ532425.1 | DQ889695.1 | EF364143.1 |
| DQ532381.1 | DQ532426.1 | DQ889696.1 | EF364144.1 |
| DQ532382.1 | DQ532427.1 | DQ889697.1 | EF364145.1 |
| DQ532383.1 | DQ532428.1 | DQ889698.1 | EF364146.1 |
| DQ532384.1 | DQ532429.1 | DQ889699.1 | EF364147.1 |
| DQ532385.1 | DQ532430.1 | DQ889700.1 | EF364148.1 |
| DQ532386.1 | DQ532431.1 | DQ889701.1 | EF364149.1 |

TABLE 13-continued

GENBANK Accession Numbers of Polyphenol oxidase homologs

| | | | |
|---|---|---|---|
| DQ532387.1 | DQ532432.1 | DQ889702.1 | EF364150.1 |
| DQ532388.1 | DQ838002.1 | DQ889703.1 | EF364151.1 |
| DQ532389.1 | DQ841551.1 | DQ889704.1 | EF364152.1 |
| EF364153.1 | EF364198.1 | EF364329.1 | EF376135.1 |
| EF364154.1 | EF364199.1 | EF364330.1 | EF376136.1 |
| EF364155.1 | EF364200.1 | EF364331.1 | EF376137.1 |
| EF364156.1 | EF364201.1 | EF364332.1 | EF376138.1 |
| EF364157.1 | EF364202.1 | EF364333.1 | EF376139.1 |
| EF364158.1 | EF364203.1 | EF364334.1 | EF376140.1 |
| EF364159.1 | EF364204.1 | EF364335.1 | EF376141.1 |
| EF364160.1 | EF364205.1 | EF364336.1 | EF376142.1 |
| EF364161.1 | EF364206.1 | EF364337.1 | EF376143.1 |
| EF364162.1 | EF364207.1 | EF364338.1 | EF376145.1 |
| EF364163.1 | EF364208.1 | EF364339.1 | EF376146.1 |
| EF364164.1 | EF364209.1 | EF364340.1 | EF376148.1 |
| EF364165.1 | EF364210.1 | EF364341.1 | EF376149.1 |
| EF364166.1 | EF364211.1 | EF364342.1 | EF376150.1 |
| EF364167.1 | EF364212.1 | EF364343.1 | EF376151.1 |
| EF364168.1 | EF364213.1 | EF364344.1 | EF376152.1 |
| EF364169.1 | EF364214.1 | EF364345.1 | EF376153.1 |
| EF364170.1 | EF364215.1 | EF364346.1 | EF376154.1 |
| EF364171.1 | EF364216.1 | EF364347.1 | EF376155.1 |
| EF364172.1 | EF364217.1 | EF364348.1 | EF376156.1 |
| EF364173.1 | EF364218.1 | EF364349.1 | EF376157.1 |
| EF364174.1 | EF364219.1 | EF364350.1 | EF376158.1 |
| EF364175.1 | EF364220.1 | EF364351.1 | EF376159.1 |
| EF364176.1 | EF364221.1 | EF364352.1 | EF395959.1 |
| EF364177.1 | EF364222.1 | EF364353.1 | EF395960.1 |
| EF364178.1 | EF364223.1 | EF364354.1 | EF395961.1 |
| EF364179.1 | EF364224.1 | EF364355.1 | EF395962.1 |
| EF364180.1 | EF364311.1 | EF364356.1 | EF395963.1 |
| EF364181.1 | EF364312.1 | EF364357.1 | EF395964.1 |
| EF364182.1 | EF364313.1 | EF364358.1 | EF395965.1 |
| EF364183.1 | EF364314.1 | EF364359.1 | EF395966.1 |
| EF364184.1 | EF364315.1 | EF364360.1 | EF395967.1 |
| EF364185.1 | EF364316.1 | EF364361.1 | EF395968.1 |
| EF364186.1 | EF364317.1 | EF364362.1 | EF395969.1 |
| EF364187.1 | EF364318.1 | EF376122.1 | EF395970.1 |
| EF364188.1 | EF364319.1 | EF376123.1 | EF395971.1 |
| EF364189.1 | EF364320.1 | EF376125.1 | EF395972.1 |
| EF364190.1 | EF364321.1 | EF376126.1 | EF395973.1 |
| EF364191.1 | EF364322.1 | EF376128.1 | EF395974.1 |
| EF364192.1 | EF364323.1 | EF376129.1 | EF395975.1 |
| EF364193.1 | EF364324.1 | EF376130.1 | EF395976.1 |
| EF364194.1 | EF364325.1 | EF376131.1 | EF395977.1 |
| EF364195.1 | EF364326.1 | EF376132.1 | EF395978.1 |
| EF364196.1 | EF364327.1 | EF376133.1 | EF395979.1 |
| EF364197.1 | EF364328.1 | EF376134.1 | EF395980.1 |
| EF395981.1 | EF493477.1 | EF571127.1 | EF646495.1 |
| EF395982.1 | EF493478.1 | EF571128.1 | EF646497.1 |
| EF395983.1 | EF493479.1 | EF571129.1 | EF646498.1 |
| EF395984.1 | EF493480.1 | EF571130.1 | EF646499.1 |
| EF395985.1 | EF493481.1 | EF571131.1 | EF646500.1 |
| EF395986.1 | EF493482.1 | EF571132.1 | EF646501.1 |
| EF395987.1 | EF493483.1 | EF571133.1 | EF646502.1 |
| EF395988.1 | EF493484.1 | EF571134.1 | EF646503.1 |
| EF395989.1 | EF493485.1 | EF571135.1 | EF646504.1 |
| EF395990.1 | EF493486.1 | EF571136.1 | EF646506.1 |
| EF395991.1 | EF493487.1 | EF571137.1 | EF646507.1 |
| EF395992.1 | EF493488.1 | EF571138.1 | EF646508.1 |
| EF395993.1 | EF493489.1 | EF571139.1 | EF650014.1 |
| EF405957.1 | EF493490.1 | EF571140.1 | EF650016.1 |
| EF407506.1 | EF493491.1 | EF571141.1 | EF650017.1 |
| EF432113.1 | EF493492.1 | EF571142.1 | EF675246.1 |
| EF445968.1 | EF493493.1 | EF571143.1 | EF675247.1 |
| EF445969.1 | EF493494.1 | EF571144.1 | EF675248.1 |
| EF445970.1 | EF493495.1 | EF571145.1 | EF675249.1 |
| EF445971.1 | EF493496.1 | EF571146.1 | EF675250.1 |
| EF445972.1 | EF493497.1 | EF571147.1 | EF675251.1 |
| EF445973.1 | EF493498.1 | EF571148.1 | EF675252.1 |
| EF445974.1 | EF493500.1 | EF623826.1 | EF675253.1 |
| EF493455.1 | EF493501.1 | EF635860.1 | EF675254.1 |
| EF493456.1 | EF493502.1 | EF646474.1 | EF675255.1 |
| EF493457.1 | EF493503.1 | EF646475.1 | EF675256.1 |
| EF493458.1 | EF493504.1 | EF646476.1 | EF675257.1 |
| EF493459.1 | EF493505.1 | EF646477.1 | EF675258.1 |
| EF493460.1 | EF493506.1 | EF646478.1 | EF675259.1 |
| EF493461.1 | EF493507.1 | EF646479.1 | EF675260.1 |

TABLE 13-continued

GENBANK Accession Numbers of Polyphenol oxidase homologs

| | | | |
|---|---|---|---|
| EF493462.1 | EF493509.1 | EF646480.1 | EF675261.1 |
| EF493463.1 | EF493510.1 | EF646481.1 | EF675262.1 |
| EF493464.1 | EF571114.1 | EF646482.1 | EF675263.1 |
| EF493465.1 | EF571115.1 | EF646483.1 | EF675264.1 |
| EF493466.1 | EF571116.1 | EF646484.1 | EF675265.1 |
| EF493467.1 | EF571117.1 | EF646485.1 | EF675266.1 |
| EF493468.1 | EF571118.1 | EF646486.1 | EF675267.1 |
| EF493469.1 | EF571119.1 | EF646487.1 | EF675268.1 |
| EF493470.1 | EF571120.1 | EF646488.1 | EF675269.1 |
| EF493471.1 | EF571121.1 | EF646489.1 | EF675270.1 |
| EF493472.1 | EF571122.1 | EF646490.1 | EF675271.1 |
| EF493473.1 | EF571123.1 | EF646491.1 | EF675272.1 |
| EF493474.1 | EF571124.1 | EF646492.1 | EF675273.1 |
| EF493475.1 | EF571125.1 | EF646493.1 | EF675274.1 |
| EF493476.1 | EF571126.1 | EF646494.1 | EF675275.1 |
| EF675276.1 | EF675321.1 | EF988277.1 | EF988327.1 |
| EF675277.1 | EF675322.1 | EF988278.1 | EF988328.1 |
| EF675278.1 | EF675323.1 | EF988279.1 | EF988329.1 |
| EF675279.1 | EF675324.1 | EF988280.1 | EF988330.1 |
| EF675280.1 | EF675325.1 | EF988281.1 | EF988331.1 |
| EF675281.1 | EF675326.1 | EF988282.1 | EF988332.1 |
| EF675282.1 | EF675327.1 | EF988283.1 | EU022001.1 |
| EF675283.1 | EF675328.1 | EF988284.1 | EU028313.1 |
| EF675284.1 | EF675329.1 | EF988285.1 | EU037991.1 |
| EF675285.1 | EF675330.1 | EF988286.1 | EU046599.1 |
| EF675286.1 | EF675331.1 | EF988287.1 | EU046600.1 |
| EF675287.1 | EF675332.1 | EF988288.1 | EU048225.1 |
| EF675288.1 | EF675333.1 | EF988289.1 | EU076756.1 |
| EF675289.1 | EF675334.1 | EF988290.1 | EU076757.1 |
| EF675290.1 | EF675335.1 | EF988291.1 | EU076758.1 |
| EF675291.1 | EF675336.1 | EF988292.1 | EU076759.1 |
| EF675292.1 | EF675337.1 | EF988293.1 | EU076760.1 |
| EF675293.1 | EF675338.1 | EF988294.1 | EU076761.1 |
| EF675294.1 | EF675339.1 | EF988295.1 | EU076762.1 |
| EF675295.1 | EF675340.1 | EF988296.1 | EU076763.1 |
| EF675296.1 | EF675341.1 | EF988297.1 | EU076764.1 |
| EF675297.1 | EF675342.1 | EF988298.1 | EU076765.1 |
| EF675298.1 | EF675343.1 | EF988299.1 | EU076766.1 |
| EF675299.1 | EF675344.1 | EF988300.1 | EU076767.1 |
| EF675300.1 | EF675345.1 | EF988301.1 | EU076768.1 |
| EF675301.1 | EF675346.1 | EF988302.1 | EU076769.1 |
| EF675302.1 | EF675347.1 | EF988303.1 | EU076770.1 |
| EF675303.1 | EF675348.1 | EF988304.1 | EU076771.1 |
| EF675304.1 | EF675349.1 | EF988305.1 | EU076772.1 |
| EF675305.1 | EF675350.1 | EF988306.1 | EU076773.1 |
| EF675306.1 | EF675351.1 | EF988308.1 | EU076774.1 |
| EF675307.1 | EF675352.1 | EF988309.1 | EU076775.1 |
| EF675308.1 | EF675353.1 | EF988310.1 | EU076776.1 |
| EF675309.1 | EF675354.1 | EF988311.1 | EU076777.1 |
| EF675310.1 | EF675355.1 | EF988312.1 | EU076778.1 |
| EF675311.1 | EF675356.1 | EF988313.1 | EU076779.1 |
| EF675312.1 | EF675357.1 | EF988314.1 | EU076780.1 |
| EF675313.1 | EF675358.1 | EF988315.1 | EU076781.1 |
| EF675314.1 | EF675359.1 | EF988316.1 | EU076782.1 |
| EF675315.1 | EF675360.1 | EF988317.1 | EU076783.1 |
| EF675316.1 | EF675361.1 | EF988318.1 | EU076784.1 |
| EF675317.1 | EF988271.1 | EF988320.1 | EU076785.1 |
| EF675318.1 | EF988273.1 | EF988322.1 | EU076786.1 |
| EF675319.1 | EF988274.1 | EF988325.1 | EU076787.1 |
| EF675320.1 | EF988276.1 | EF988326.1 | EU076788.1 |
| EU076789.1 | EU215590.1 | EU769531.1 | M11302.1 |
| EU076790.1 | EU215591.1 | EU769532.1 | M11582.1 |
| EU076791.1 | EU215592.1 | EU769533.1 | M20234.1 |
| EU076792.1 | EU215593.1 | EU769534.1 | M24560.1 |
| EU076793.1 | EU215594.1 | EU769535.1 | M26729.1 |
| EU076794.1 | EU215595.1 | EU769536.1 | M27160.1 |
| EU076795.1 | EU215596.1 | EU769537.1 | M32843.1 |
| EU076796.1 | EU215597.1 | EU769538.1 | M33271.1 |
| EU076797.1 | EU215598.1 | EU769539.1 | M57288.1 |
| EU076798.1 | EU215599.1 | EU769540.1 | M63235.1 |
| EU076799.1 | EU215600.1 | EU769541.1 | M63237.1 |
| EU076800.1 | EU215601.1 | EU769542.1 | M74314.1 |
| EU076801.1 | EU215602.1 | EU769543.1 | M95196.1 |
| EU076802.1 | EU215603.1 | EU769544.1 | M95197.1 |
| EU076803.1 | EU215604.1 | EU769545.1 | NG_008748.1 |
| EU076804.1 | EU215605.1 | EU769546.1 | NM_000372.4 |
| EU076805.1 | EU215606.1 | EU769547.1 | NM_000550.2 |
| EU076806.1 | EU215607.1 | EU769548.1 | NM_001002749.1 |

TABLE 13-continued

GENBANK Accession Numbers of Polyphenol oxidase homologs

| | | | |
|---|---|---|---|
| EU126854.1 | EU215608.1 | EU769549.1 | NM_001002941.1 |
| EU139474.1 | EU215609.1 | EU769550.1 | NM_001012666.1 |
| EU147298.1 | EU215610.1 | EU769551.1 | NM_001016476.2 |
| EU154993.1 | EU215611.1 | EU787433.1 | NM_001017161.2 |
| EU186763.1 | EU215612.1 | EU939720.1 | NM_001022594.1 |
| EU186764.1 | EU215613.1 | EU939721.1 | NM_001025212.1 |
| EU186765.1 | EU275350.1 | EU939722.1 | NM_001025226.1 |
| EU186766.1 | EU330225.1 | EU939723.1 | NM_001025227.1 |
| EU186768.1 | EU371651.1 | EU955868.1 | NM_001033837.1 |
| EU186769.1 | EU371652.1 | EU956830.1 | NM_001039975.1 |
| EU186770.1 | EU371653.1 | EU963699.1 | NM_001042560.2 |
| EU186771.1 | EU371654.1 | EU966440.1 | NM_001051031.1 |
| EU186772.1 | EU371656.1 | FJ184078.1 | NM_001060465.1 |
| EU186773.1 | EU371657.1 | FJ210643.1 | NM_001060466.1 |
| EU186774.1 | EU522120.1 | FJ210644.1 | NM_001060467.1 |
| EU186775.1 | EU523113.1 | FJ210645.1 | NM_001076816.1 |
| EU186776.1 | EU554632.1 | FM178478.1 | NM_001081840.1 |
| EU186777.1 | EU555188.1 | FM864217.1 | NM_001082077.1 |
| EU186778.1 | EU627590.1 | FM877576.1 | NM_001087023.1 |
| EU186779.1 | EU627691.1 | FM877577.1 | NM_001103048.1 |
| EU186780.1 | EU760771.1 | J02835.1 | NM_001104802.1 |
| EU215584.1 | EU760773.1 | J03581.1 | NM_001106664.1 |
| EU215585.1 | EU769526.1 | L18967.1 | NM_001107535.1 |
| EU215586.1 | EU769527.1 | L23649.2 | NM_001123643.1 |
| EU215587.1 | EU769528.1 | L29450.1 | NM_001123688.1 |
| EU215588.1 | EU769529.1 | L46685.1 | NM_001124219.1 |
| EU215589.1 | EU769530.1 | L46805.1 | NM_001124222.1 |
| NM_001128295.1 | NW_001914846.1 | XM_001083014.1 | XM_001344111.2 |
| NM_001129889.1 | NW_001914848.1 | XM_001083129.1 | XM_001372445.1 |
| NM_001130023.1 | NW_001914849.1 | XM_001104954.1 | XM_001377599.1 |
| NM_001130024.1 | NW_001914850.1 | XM_001105033.1 | XM_001386428.1 |
| NM_001130027.1 | NW_001914851.1 | XM_001111475.1 | XM_001389305.1 |
| NM_001922.3 | NW_001914853.1 | XM_001118455.1 | XM_001389898.1 |
| NM_010024.3 | NW_001914855.1 | XM_001136041.1 | XM_001393577.1 |
| NM_011661.4 | NW_001914856.1 | XM_001195948.1 | XM_001393787.1 |
| NM_031202.2 | NW_001914857.1 | XM_001208556.1 | XM_001395217.1 |
| NM_032866.3 | NW_001914859.1 | XM_001209390.1 | XM_001397251.1 |
| NM_058730.2 | NW_002196562.1 | XM_001212742.1 | XM_001402482.1 |
| NM_059308.5 | NW_002196563.1 | XM_001218713.1 | XM_001403959.1 |
| NM_059654.3 | NW_002196567.1 | XM_001219433.1 | XM_001405108.1 |
| NM_066310.3 | NW_002196569.1 | XM_001220372.1 | XM_001410762.1 |
| NM_067435.3 | S40548.1 | XM_001220433.1 | XM_001410969.1 |
| NM_068586.5 | S56788.1 | XM_001220654.1 | XM_001413345.1 |
| NM_077759.3 | S56789.1 | XM_001221472.1 | XM_001470114.1 |
| NM_077760.3 | S69231.1 | XM_001221522.1 | XM_001474717.1 |
| NM_131013.1 | S71755.1 | XM_001222188.1 | XM_001491619.2 |
| NM_131555.1 | S81675.1 | XM_001222231.1 | XM_001492560.2 |
| NM_174480.3 | U01873.1 | XM_001223254.1 | XM_001499964.1 |
| NM_181001.2 | U19270.1 | XM_001224265.1 | XM_001507059.1 |
| NM_204160.1 | U22921.1 | XM_001224529.1 | XM_001511967.1 |
| NM_204935.1 | U22922.1 | XM_001226375.1 | XM_001512063.1 |
| NM_205045.1 | U42219.1 | XM_001227018.1 | XM_001521874.1 |
| NW_001263857.1 | U46014.1 | XM_001227695.1 | XM_001521941.1 |
| NW_001594031.1 | U66807.1 | XM_001227852.1 | XM_001521969.1 |
| NW_001594096.1 | U66808.1 | XM_001228418.1 | XM_001537500.1 |
| NW_001594210.1 | U80928.5 | XM_001228654.1 | XM_001538844.1 |
| NW_001594218.1 | U83274.1 | XM_001229971.1 | XM_001539679.1 |
| NW_001594271.1 | U97407.2 | XM_001238383.1 | XM_001540372.1 |
| NW_001594359.1 | X03687.1 | XM_001239849.1 | XM_001540446.1 |
| NW_001594360.1 | X12782.1 | XM_001240419.1 | XM_001541520.1 |
| NW_001594468.1 | X16073.1 | XM_001243417.1 | XM_001543595.1 |
| NW_001849580.1 | X51420.1 | XM_001258740.1 | XM_001545601.1 |
| NW_001884663.1 | X51455.1 | XM_001264009.1 | XM_001546170.1 |
| NW_001884666.1 | X63349.1 | XM_001266670.1 | XM_001546443.1 |
| NW_001884668.1 | X69526.1 | XM_001267633.1 | XM_001555260.1 |
| NW_001884670.1 | X85113.1 | XM_001272229.1 | XM_001556657.1 |
| NW_001884672.1 | X89382.1 | XM_001273481.1 | XM_001559424.1 |
| NW_001884674.1 | X90869.1 | XM_001273821.1 | XM_001560118.1 |
| NW_001884677.1 | X95703.1 | XM_001276415.1 | XM_001560753.1 |
| NW_001884682.1 | X95705.1 | XM_001276725.1 | XM_001560913.1 |
| NW_001914832.1 | XM_001078239.1 | XM_001328999.1 | XM_001584514.1 |
| NW_001914843.1 | XM_001082890.1 | XM_001341424.2 | XM_001585797.1 |
| NW_001594867.1 | XM_001794545.1 | XM_001892395.1 | XM_002125300.1 |
| XM_001597332.1 | XM_001794653.1 | XM_001892420.1 | XM_002128389.1 |
| XM_001625411.1 | XM_001794931.1 | XM_001893247.1 | XM_002128413.1 |
| XM_001635746.1 | XM_001796832.1 | XM_001895139.1 | XM_002129643.1 |
| XM_001636194.1 | XM_001798236.1 | XM_001901072.1 | XM_002130461.1 |
| XM_001638262.1 | XM_001798742.1 | XM_001901073.1 | XM_002143212.1 |

TABLE 13-continued

GENBANK Accession Numbers of Polyphenol oxidase homologs

| | | | |
|---|---|---|---|
| XM_001638766.1 | XM_001800083.1 | XM_001903268.1 | XM_002146447.1 |
| XM_001638830.1 | XM_001801793.1 | XM_001904803.1 | XM_002149565.1 |
| XM_001640169.1 | XM_001802391.1 | XM_001905139.1 | XM_002153381.1 |
| XM_001645672.1 | XM_001802709.1 | XM_001905238.1 | XM_224517.4 |
| XM_001649753.1 | XM_001803635.1 | XM_001905452.1 | XM_361488.1 |
| XM_001665827.1 | XM_001803854.1 | XM_001905547.1 | XM_362982.1 |
| XM_001666225.1 | XM_001804507.1 | XM_001906049.1 | XM_363645.2 |
| XM_001666226.1 | XM_001805205.1 | XM_001906413.1 | XM_364769.1 |
| XM_001667828.1 | XM_001818619.1 | XM_001906450.1 | XM_365447.2 |
| XM_001668104.1 | XM_001818856.1 | XM_001906989.1 | XM_366343.2 |
| XM_001670594.1 | XM_001820921.1 | XM_001907225.1 | XM_366367.1 |
| XM_001678316.1 | XM_001821589.1 | XM_001909833.1 | XM_367508.1 |
| XM_001693100.1 | XM_001823590.1 | XM_001910225.1 | XM_367674.1 |
| XM_001697086.1 | XM_001824175.1 | XM_001912748.1 | XM_369295.2 |
| XM_001701312.1 | XM_001824991.1 | XM_001912994.1 | XM_369550.1 |
| XM_001727078.1 | XM_001827481.1 | XM_001916811.1 | XM_369602.2 |
| XM_001727530.1 | XM_001828111.1 | XM_001919765.1 | XM_382164.1 |
| XM_001728018.1 | XM_001828125.1 | XM_001930339.1 | XM_383524.1 |
| XM_001728211.1 | XM_001829397.1 | XM_001931225.1 | XM_383707.1 |
| XM_001743609.1 | XM_001829411.1 | XM_001931717.1 | XM_383794.1 |
| XM_001750461.1 | XM_001829654.1 | XM_001931950.1 | XM_383977.1 |
| XM_001752106.1 | XM_001829655.1 | XM_001931983.1 | XM_384686.1 |
| XM_001752310.1 | XM_001829755.1 | XM_001932641.1 | XM_385045.1 |
| XM_001755025.1 | XM_001829756.1 | XM_001932672.1 | XM_385804.1 |
| XM_001760085.1 | XM_001830172.1 | XM_001933667.1 | XM_388183.1 |
| XM_001766207.1 | XM_001831367.1 | XM_001935114.1 | XM_389698.1 |
| XM_001766285.1 | XM_001831834.1 | XM_001938308.1 | XM_391282.1 |
| XM_001766501.1 | XM_001832157.1 | XM_001939194.1 | XM_391596.1 |
| XM_001767122.1 | XM_001832731.1 | XM_001939588.1 | XM_391626.1 |
| XM_001770057.1 | XM_001832740.1 | XM_001941106.1 | XM_391693.1 |
| XM_001772163.1 | XM_001834494.1 | XM_002119109.1 | XM_391704.1 |
| XM_001773718.1 | XM_001834544.1 | XM_002119565.1 | XM_396715.2 |
| XM_001777448.1 | XM_001835487.1 | XM_002119639.1 | XM_508687.2 |
| XM_001785193.1 | XM_001835984.1 | XM_002122507.1 | XM_520488.2 |
| XM_001785572.1 | XM_001838066.1 | XM_002122831.1 | XM_531934.2 |
| XM_001785897.1 | XM_001838103.1 | XM_002123004.1 | XM_542639.2 |
| XM_001791723.1 | XM_001885099.1 | XM_002124302.1 | XM_633156.1 |
| XM_001794065.1 | XM_001885343.1 | XM_002124333.1 | XM_633850.1 |
| XM_001794296.1 | XM_001885517.1 | XM_002125243.1 | XM_633851.1 |
| XM_652743.1 | XM_746360.1 | XM_954050.1 | Z12833.1 |
| XM_653830.1 | XM_748017.1 | XM_954644.1 | Z12834.1 |
| XM_655311.1 | XM_752184.1 | XM_959730.1 | Z12835.1 |
| XM_657823.1 | XM_756546.1 | XM_959839.2 | Z12836.1 |
| XM_658954.1 | XM_787355.2 | XM_969232.2 | Z12837.1 |
| XM_658998.1 | XM_859433.1 | XR_022754.1 | Z12838.1 |
| XM_659572.1 | XM_859450.1 | Y00819.1 | Z27411.1 |
| XM_676089.1 | XM_870599.3 | Y12501.1 | Z66559.1 |
| XM_676612.1 | XM_952931.2 | Y13219.2 | Z71261.1 |
| XM_677565.1 | XM_953538.2 | Z11702.1 | Z81568.1 |
| XM_743335.1 | | | |

Example 21

Additional Monophenol Oxidases

Given the demonstration of strong SCN activity by enzyme from bacteria and fungi with homology to monophenol oxidase/tyrosinases, it is now apparent that many previously identified enzymes of this class will exhibit activity on SCN.

Example 22

Assays for Nematicidal Activity

The nucleotide sequences of the invention can be tested for their ability to produce nematicidal proteins. The ability of a protein to act as a pesticide upon a nematode pest is often assessed in a number of ways. One way well known in the art is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods*, CRC, Boca Raton, Fla. Alternatively, assays are commonly described in the journals *Arthropod Management Tests and*

*Journal of Economic Entomology* or by discussion with members of the Entomological Society of America (ESA).

Example 23

Synthetic Gene Sequences

The following genes were designed that encode either the AXN-1, AXN-2, AXN-8, or AXN-9 amino acid sequences, but utilizing a different nucleotide sequence.

SEQ ID NO:6 describes a novel AXN-1 encoding nucleotide sequence

SEQ ID NO:10 describes a novel AXN-2 encoding nucleotide sequence

SEQ ID NO:15 describes a novel AXN-8 encoding nucleotide sequence

SEQ ID NO:17 describes a novel nucleotide sequence encoding the protein predicted from GENBANK accession number AK246031 from *Glycine max*.

SEQ ID NO:21 describes a novel nucleotide sequence encoding the protein predicted from genbank accession number the cDNA with GENBANK accession number AM418385 encoding a *T. reesei* enzyme.

Example 24

Vectoring of Genes for Plant Expression

The coding regions of the invention are connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter-gene-terminator constructs also are well known in the art.

In one aspect of the invention, synthetic DNA sequences are designed and generated. These synthetic sequences have altered nucleotide sequence relative to the parent sequence, but encode proteins that are essentially identical to the parent amino acid sequence.

In another aspect of the invention, modified versions of the synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENBANK®ID GI:14276838, Miller et al. (2001) *Plant Physiology* 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (i.e., the "KDEL" motif, SEQ ID NO:30) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, this gene encodes a fusion protein that contains the N-terminal thirty-one amino acids of the acid phosphatase gene from the White Lupin *Lupinus albus* (GENBANK® ID GI:14276838, Miller et al., 2001, supra) fused to the N-terminus of the sequence of the invention, as well as the KDEL sequence at the C-terminus. Thus, the resulting protein is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vectors from *Agrobacterium*-mediated transformation or simple plasmid vectors for aerosol or biolistic transformation.

Example 25

Vectoring Genes for Plant Expression

The coding region DNA of the genes encompassed herein are operably connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter-gene-terminator constructs also are well known in the art.

The plant expression cassettes described above are combined with an appropriate plant selectable marker to aid in the selections of transformed cells and tissues, and ligated into plant transformation vectors. These may include binary vectors from *Agrobacterium*-mediated transformation or simple plasmid vectors for aerosol or biolistic transformation.

Example 26

AXN-1 Protein Expression in Soybean Root Tissue

Vector Construction

Vector pAG6004 was prepared to guide overexpression of the AXN-1 protein in soybean hairy root tissues. pAG6004 contains the full-length AXN-1 gene, organized 3' to the UBQ10 promoter (*Arabidopsis thaliana*) and 5' to the 35S terminator (cauliflower mosaic virus), in a manner likely to lead to transcription of the axn-1 gene from the UBQ10 promoter, and termination of such transcription by the 35S terminator. Also present in the vector is a visual marker (yellow fluorescent protein (YFP), under control of UBQ3 promoter), a replication origin functional in *Agrobacterium* species, and a gentamicin resistance gene. The organization of the vector was confirmed by DNA sequencing of the entire vector, and then introduced into *Agrobacterium rhizogenes* strain K599 and propagated by growth on gentamicin.

Soybean Transformation

Soybean hairy root cultures were prepared as follows. Soybean seeds (cultivar Williams 82) were germinated in a growth chamber (25° C.) for 1 week, at which time the cotyledons were excised (after removing seed coats). The cotyledons were then wounded with a scalpel that had been dipped in an overnight *A. rhizogenes* culture transformed with pAG6004. The infected cotyledons were placed abaxial side up on the top of a Whatman filter paper, submerged in sterile water in a Petri dish and incubated in a dark growth chamber at 25° C. for 3 to 5 days. Next, individual cotyledons were transferred to and cultured abaxial side up on MB carb medium (MS salts, B5 vitamins, 3% sucrose, 500 mg/L of carbenicillin, and solidified with 3 g/L of Gelrite). Cotyledons were sub-cultured every two weeks on the same MB carb medium to regenerate hairy roots. Roots expressing yellow fluorescent protein (YFP) gene associated with AXN-1 gene derived from pAG6004 were detected under a ZEISS stereo dissecting microscope (KL 1500 LCD) with filter set (exciting filter 508 nm; emission filter 524 nm). YFP roots were sub-cultured on the same MB carb medium every two weeks or as needed.

Detection of AXN-1 Protein in Root Tissue

Western blot analysis was utilized to identify AXN-1 protein expression in hairy root tissues. One gram of transgenic and control tissues that had been grown for approximately 6 weeks were suspended 2×LDS loading dye (Invitrogen) with 2.5 mM β-mercaptoethanol, and then homogenized using stainless beads in a bead beater instrument. The homogenized extracts were separated on a 4-20% Big-Tris gel, transferred to nitrocellulose, and then incubated with rabbit serum from rabbits immunized with purified AXN-1 protein. Following a series of wash steps and incubation with a secondary antibody (donkey anti-rabbit, conjugated with horseradish peroxidase, Pierce), the presence of AXN-1 was visualized by ECL (Pierce). Interestingly, this analysis revealed that the soybean roots generated a truncated form of the protein (approximately 50 kDa) rather than the full-length protein (103 kDa). This observation is consistent with post-translational processing of the AXN-1 protein, and matches the size of the AXN-1 protein that was purified from the host bacterial strain, ATX21995.

Detection of AXN-8 Protein in Root Tissue

Western blot analysis was utilized to identify AXN-8 protein expression in hairy root tissues. One gram of transgenic and control tissues that had been grown for approximately 6 weeks were suspended 2×LDS loading dye (Invitrogen) with 2.5 mM β-mercaptoethanol, and then homogenized using stainless beads in a bead beater instrument. The homogenized extracts were separated on a 4-20% Big-Tris gel, transferred to nitrocellulose, and then incubated with rabbit serum from rabbits immunized with purified AXN-8 protein. Following a series of wash steps and incubation with a secondary antibody (donkey anti-rabbit, conjugated with horseradish peroxidase, Pierce), the presence of AXN-8 was visualized by ECL (Pierce). This analysis revealed that the soybean roots generated a full-length AXN-8 protein (approximately 50 kDa in size) that matches the size of the AXN-8 protein that was purified from the host bacterial strain, ATX20514, as well as additional truncated forms of the protein.

Detection of Phenol Oxidase Enzymatic Activity in Root Tissue

Several phenol oxidases, including AXN-1, can utilize tyrosine as a substrate to produce melanin. To determine if the AXN-1 protein expressed in soybean hairy roots was enzymatically active, we carried out enzymatic assays with protein extracts from AXN-1 (pAG6004) and control (pAG5385) root tissues. Each tissue (approximately 1 gram) was homogenized in liquid nitrogen, and 10 mg of each was suspended in 0.4 mL of buffer (20 mM Tris, pH 8.0). Each tissue suspension was then added at $1/10^{th}$ final volume to enzyme assays containing the same buffer and 1 mM tyrosine. Assay reactions were incubated overnight, and a commercial tyrosinase preparation (Sigma-Aldrich) was used as a positive control for enzymatic activity. Both the AXN-1 root tissue and commercial tyrosinase enzyme generated a brown color in the assay that is consistent with melanin, while control root tissue was negative. Color formation was dependent on the presence of the substrate tyrosine. Thus, axn-1 is effectively expressed in soybean tissue, resulting in active polyphenol oxidase activity.

Example 27

Transformation of Maize Cells with the Nematicidal Genes Described Herein

Maize ears are best collected 8-12 days after pollination. Embryos are isolated from the ears, and those embryos 0.8- 1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

| Materials DN62A5S Media | | |
|---|---|---|
| Components | Per Liter | Source |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 28

Transformation of the Genes of the Invention in Plant Cells by *Agrobacterium*-Mediated Transformation Ears are best collected 8-12 days after pollination. Embryos are isolated from the ears, and those embryos 0.8-

1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

Example 29

AXN-8 Protein Expression in Maize Leaf Tissue

Vector Construction

Vector pAG4146 was prepared to guide overexpression of the AXN-8 protein in maize tissues. pAG4146 contains the full-length AXN-8 gene, organized 3' to the sugarcane Ubi4 ubiquitin promoter (*Saccharum* sp.) and 5' to the 35S terminator (cauliflower mosaic virus), in a manner likely to lead to transcription of the axn-8 gene from the Ubi promoter, and termination of such transcription by the 35S terminator. Also present in the vector is a selectable marker that confers resistance to glyphosate (GRG23ace5, under control of sugarcane Ubi4 promoter), a replication origin functional in *Agrobacterium* species, and a spectinomycin resistance gene. The organization of the vector was confirmed by DNA sequencing of the entire vector.

Detection of AXN-8 Protein in Maize Leaf Tissues

Western blot analysis was utilized to identify AXN-8 protein expression in both leaf and root tissues. One gram of transgenic and control tissues were suspended 2×LDS loading dye (Invitrogen) with 2.5 mM β-mercaptoethanol, and then homogenized using stainless beads in a bead beater instrument. The homogenized extracts were separated on a 4-20% Big-Tris gel, transferred to nitrocellulose, and then incubated with rabbit serum from rabbits immunized with purified AXN-8 protein. Following a series of wash steps and incubation with a secondary antibody (donkey anti-rabbit, conjugated with horseradish peroxidase, Pierce), the presence of AXN-8 was visualized by ECL (Pierce). The size of the protein detected by Western blot was very similar for the leaf and root tissue, and is similar to that expected for the full-length AXN-8 protein (approximately 50 kDa), and matches the size of the AXN-8 protein that was purified from the host bacterial strain, ATX20514.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a nucleotide sequence encoding an amino acid sequence having nematicidal activity, wherein said nucleotide sequence is selected from the group consisting of:
   a) a nucleotide sequence that encodes a polypeptide comprising the amino acid sequence of SEQ ID NO:8 or 9;
   b) a nucleotide sequence encoding a proteolytic cleavage fragment of SEQ ID NO:8, or 9, wherein said fragment has nematicidal activity;
   c) a nucleotide sequence that encodes a polypeptide comprising an amino acid sequence having at least 95% sequence identity to the amino acid sequence of SEQ ID NO:8 or 9; and
   d) the nucleotide sequence set forth in SEQ ID NO: 7.

2. The isolated nucleic acid molecule of claim 1, wherein said nucleotide sequence is a synthetic sequence that has been designed for expression in a plant.

3. The isolated nucleic acid molecule of claim 2, wherein said synthetic sequence comprises SEQ ID NO:10.

4. A vector comprising the nucleic acid molecule of claim 1.

5. The vector of claim 4, further comprising a nucleic acid molecule encoding a heterologous polypeptide.

6. A bacterial host cell that contains the insert of the vector of claim 4.

7. A transgenic plant cell comprising a nucleotide sequence encoding a polypeptide selected from the group consisting of:
   a) a polypeptide comprising the amino acid sequence of SEQ ID NO:8 or 9;
   b) a polypeptide comprising an amino acid sequence having at least 95% sequence identity to the amino acid sequence of SEQ ID NO:8 or 9, wherein said polypeptide has nematicidal activity;
   c) a polypeptide that is a proteolytic cleavage fragment of SEQ ID NO:8 or 9, wherein said fragment has nematicidal activity; and
   d) a polypeptide that is encoded by SEQ ID NO:7.

8. A transgenic plant regenerated from the plant cell of claim 7.

9. The transgenic plant of claim 8, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

10. An isolated polypeptide with nematicidal activity, selected from the group consisting of:
    a) a polypeptide comprising the amino acid sequence of SEQ ID NO: 8 or 9;
    b) a polypeptide comprising an amino acid sequence having at least 95% sequence identity to the amino acid sequence of SEQ ID NO: 8 or 9, wherein said polypeptide has nematicidal activity;
    c) a polypeptide that is a proteolytic cleavage fragment of SEQ ID NO: 8 or 9, wherein said fragment has nematicidal activity; and
    d) a polypeptide that is encoded by SEQ ID NO: 7.

11. The polypeptide of claim 10 further comprising heterologous amino acid sequence.

12. A composition comprising the polypeptide of claim 10.

13. The composition of claim 12, wherein said composition is selected from the group consisting of a powder, dust, pellet, granule, spray, emulsion, colloid, and solution.

14. The composition of claim 12, wherein said composition is prepared by desiccation, lyophilization, homogenization, extraction, filtration, centrifugation, sedimentation, or concentration of a culture of bacterial cells.

15. The composition of claim 12, comprising from about 1% to about 99% by weight of said polypeptide.

16. A method for killing or controlling a nematode pest, comprising contacting said pest with, or feeding to said pest, a nematicidally-effective amount of a composition comprising the polypeptide of claim 10.

17. A method for protecting a plant from a pest, comprising introducing into said plant or cell thereof at least one expression vector comprising a nucleotide sequence that encodes a nematicidal polypeptide, wherein said plant is planted in an area susceptible to nematode infestation, and wherein said nucleotide sequence is selected from the group consisting of:
    a) a nucleotide sequence that encodes a polypeptide comprising the amino acid sequence of SEQ ID NO:8 or 9;
    b) a nucleotide sequence encoding a proteolytic cleavage fragment of SEQ ID NO:8 or 9, wherein said fragment has nematicidal activity;
    c) a nucleotide sequence that encodes a polypeptide comprising an amino acid sequence having at least 95% sequence identity to the amino acid sequence of SEQ ID NO:8 or 9; and
    d) the nucleotide sequence set forth in SEQ ID NO:7.

\* \* \* \* \*